United States Patent [19]

Tojo et al.

[11] Patent Number: 5,847,189

[45] Date of Patent: Dec. 8, 1998

[54] METHOD FOR CONTINUOUSLY PRODUCING A DIALKYL CARBONATE AND A DIOL

[75] Inventors: Masahiro Tojo; Shinsuke Fukuoka, both of Kurashiki; Mamoru Kawamura, Oomiya, all of Japan

[73] Assignee: Asahi Kasei Kogyo Kabushiki Kaisha, Osaka, Japan

[21] Appl. No.: 930,700

[22] PCT Filed: Dec. 20, 1996

[86] PCT No.: PCT/JP96/03746

§ 371 Date: Oct. 16, 1997

§ 102(e) Date: Oct. 16, 1997

[87] PCT Pub. No.: WO97/23445

PCT Pub. Date: Jul. 3, 1997

[30] Foreign Application Priority Data

Dec. 22, 1995 [JP] Japan ................................... 7-334928

[51] Int. Cl.$^6$ ................................................. C07C 68/06
[52] U.S. Cl. ........................................... 558/277; 558/275
[58] Field of Search ................................. 558/275, 277

[56] References Cited

U.S. PATENT DOCUMENTS 4,691,041  9/1987  Duranleau et al. ..................... 558/277
5,231,212  7/1993  Buysch et al. ......................... 558/277
5,359,118  10/1994 Wagner et al. ......................... 558/277

FOREIGN PATENT DOCUMENTS 4198141  7/1992  Japan .

*Primary Examiner*—Michael G. Ambrose
*Attorney, Agent, or Firm*—Birch, Stewart, Kolasch & Birch, LLP

[57] ABSTRACT

Disclosed is a method for continuously producing a dialkyl carbonate and a diol, comprising: (1) feeding a cyclic carbonate and an aliphatic monohydric alcohol to a continuous multi-stage distillation column, and effecting a transesterification in the presence of a catalyst in the multi-stage distillation column and/or at least one transesterification reactor which communicates fluid-tightly with the distillation column, while continuously withdrawing a low boiling point gaseous mixture containing the produced dialkyl carbonate from a upper portion of the distillation column and a high boiling point liquid mixture from a lower portion of the distillation column; and (2) continuously feeding water and the high boiling point mixture to a hydrolysis reactor, to thereby effect a continuous hydrolysis of the unreacted cyclic carbonate contained therein and produce a diol and carbon dioxide. By the method of the present invention, it becomes possible to produce a dialkyl carbonate and a high purity diol, with high productivity, even when the feedstock aliphatic monohydric alcohol contains a concomitant dialkyl carbonate.

16 Claims, 11 Drawing Sheets

METHOD FOR CONTINUOUSLY PRODUCING A DIALKYL CARBONATE AND A DIOL

This application is a 371 of PCT/JP96/03746, filed Dec. 20, 1996.

BACKGROUND OF THE INVENTION

1. Field of The Invention

The present invention relates to a method for continuously producing a dialkyl carbonate and a diol from a cyclic carbonate and an aliphatic monohydric alcohol. More particularly, the present invention is concerned with a method for continuously producing a dialkyl carbonate and a diol, comprising: (1) feeding a cyclic carbonate and an aliphatic monohydric alcohol containing 0 to 40% by weight of a concomitant dialkyl carbonate to a continuous multi-stage distillation column, and effecting a transesterification between the cyclic carbonate and the aliphatic monohydric alcohol in the presence of a catalyst in at least one reaction zone selected from the group consisting of the multi-stage distillation column and at least one transesterification reactor which is disposed outside of the multi-stage distillation column and which communicates fluid-tightly with the multi-stage distillation column so that a liquid flowing-down inside the distillation column can be continuously introduced to the transesterification reactor and the resultant reaction mixture can be continuously recycled to the distillation column, while continuously withdrawing a low boiling point mixture containing the produced dialkyl carbonate in a gaseous form from an upper portion of the distillation column and continuously withdrawing a high boiling point mixture containing the produced diol and unreacted cyclic carbonate in a liquid form from a lower portion of the distillation column; and (2) continuously feeding water and the high boiling point mixture withdrawn from a lower portion of the distillation column to a continuous hydrolysis reactor, to thereby effect a continuous hydrolysis of the unreacted cyclic carbonate and produce a diol and carbon dioxide, while continuously withdrawing the resultant hydrolysis reaction mixture containing the produced diol from the continuous hydrolysis reactor.

By the method of the present invention, it becomes possible to produce a dialkyl carbonate and a high purity diol with high productivity from a cyclic carbonate and an aliphatic monohydric alcohol containing 0 to 40% by weight of a concomitant dialkyl carbonate.

2. Prior Art

With respect to the method for producing a dialkyl carbonate and a diol by reacting a cyclic carbonate with an aliphatic monohydric alcohol, various proposals have been made. Most of those proposals relate to the development of catalysts for the above reaction. Examples of such catalysts include alkali metals or basic compounds containing alkali metals [see U.S. Pat. No. 3,642,858, Unexamined Japanese Patent Application Laid-Open Specification No. 54-48715 (corresponding to U.S. Pat. No. 4,181,676)], tertiary aliphatic amines [see Unexamined Japanese Patent Application Laid-Open Specification No. 51-122025 (corresponding to U.S. Pat. No. 4,062,884)], thallium compounds [see Unexamined Japanese Patent Application Laid-Open Specification No. 54-48716 (corresponding to U.S. Pat. No. 4,307,032)], tin alkoxides (see Unexamined Japanese Patent Application Laid-Open Specification No. 54-63023), alkoxides of zinc, aluminum and titanium (see Unexamined Japanese Patent Application Laid-Open Specification No. 54-148726), a mixture of a Lewis acid with an nitrogen-containing organic base (see Unexamined Japanese Patent Application Laid-Open Specification No. 55-64550), phosphine compounds (see Unexamined Japanese Patent Application Laid-Open Specification No. 55-64551), quaternary phosphonium salts (see Unexamined Japanese Patent Application Laid-Open Specification No. 56-10144), cyclic amidines [see Unexamined Japanese Patent Application Laid-Open Specification No. 59-106436 (corresponding to U.S. Pat. No. 4,681,967, EP-110629B, and DE-3366133G)], compounds of zirconium, titanium and tin [see Unexamined Japanese Patent Application Laid-Open Specification No. 63-41432 (corresponding to U.S. Pat. No. 4,616,609, EP-255252B1 and DE-3781742)], a quaternary ammonium group-containing strongly basic anion-exchange solid material (see Unexamined Japanese Patent Application Laid-Open Specification No. 63-238043), a solid catalyst selected from the group consisting of a tertiary amine- or quaternary ammonium group-containing ion-exchange resin, a strongly acidic or a weakly acidic ion-exchange resin, a mixture of an alkali metal with silica, a silicate of an alkaline earth metal, an ammonium ion-exchange zeolite [see Unexamined Japanese Patent Application Laid-Open Specification No. 64-31737 (corresponding to U.S. Pat. No. 4,691,041)], a homogeneous catalyst selected from the group consisting of tertiary phosphine, tertiary arsine, tertiary stibine, a divalent sulfur compound and a selenium compound (see U.S. Pat. No. 4,734,518).

With respect to the method for conducting the above-mentioned reaction between a cyclic carbonate and a diol, the below-mentioned four types of methods (1) to (4) have conventionally been proposed. Hereinbelow, explanation is made with respect to such methods (1) to (4), taking as an example a reaction between ethylene carbonate and methanol, which is the most representative example of reactions between cyclic carbonates and diols.

(1) A completely batchwise method.

(2) A batchwise method using a reaction vessel provided at an upper portion thereof with a distillation column.

(3) A liquid flow method using a tubular reactor.

(4) A reactive distillation method.

The completely batchwise method (1) is a method in which ethylene carbonate, methanol and a catalyst are fed to an autoclave as a batchwise reaction vessel, and a reaction is performed at a reaction temperature higher than the boiling point of methanol under pressure for a predetermined period of time (see U.S. Pat. No. 3,642,858, Unexamined Japanese Patent Application Laid-Open Specification No. 54-48715 (corresponding to U.S. Pat. No. 4,181,676, EP-1082B and DE-2860078G), Unexamined Japanese Patent Application Laid-Open Specification No. 54-63023, Unexamined Japanese Patent Application Laid-Open Specification No. 54-148726, Unexamined Japanese Patent Application Laid-Open Specification No. 55-64550, Unexamined Japanese Patent Application Laid-Open Specification No. 55-6455 and Unexamined Japanese Patent Application Laid-Open Specification No. 56-10144].

The batchwise method (2), using an apparatus comprising a reaction vessel provided at an upper portion thereof with a distillation column, is a method in which ethylene carbonate, methanol and a catalyst are fed to the reaction vessel, and a reaction is performed by heating the contents of the reaction vessel to a predetermined temperature. In this method, the produced dimethyl carbonate and methanol form a minimum boiling point azeotropic mixture having a boiling point of 63° C./760 mmHg. Methanol alone has a boiling point of 64.6° C./760 mmHg. In this method, the reaction is performed under conditions such that an excess amount of methanol is present in the reaction system, while separating the resultant reaction products into the azeotropic mixture and methanol by means of the distillation column provided at the upper portion of the reaction vessel. Specifically, a gaseous mixture of dimethyl carbonate and methanol, which is formed in the reaction vessel, is transferred to the distillation column and allowed to ascend inside the distillation column, and during the ascending of the gaseous mixture, the gaseous mixture is caused to separate into a gaseous azeotropic mixture and liquid methanol. Then, the gaseous azeotropic mixture is distilled from the top of the distillation column while the liquid methanol flows down to the reaction vessel so as to be recycled to the reaction system in the reaction vessel.

The liquid flow method (3) is a method in which a solution of an ethylene carbonate/methanol mixture is continuously fed to a tubular reactor to perform a reaction at a predetermined reaction temperature in the tubular reactor, and the resultant liquid reaction mixture containing the unreacted materials (i.e., ethylene carbonate and methanol) and the reaction products (i.e., dimethyl carbonate and ethylene glycol) is continuously withdrawn through an outlet of the reactor. This method has conventionally been conducted in two different manners in accordance with the two types of catalyst used. That is, this method is conducted either in a manner such that a mixed solution of the ethylene carbonate/methanol mixture and a homogenous catalyst is passed through a tubular reactor to perform a reaction, thereby obtaining a reaction mixture, and the catalyst is separated from the obtained reaction mixture [see Unexamined Japanese Patent Application Laid-Open Specification No. 63-41432 (corresponding to U.S. Pat. No. 4,661,609, EP-255252B1 and DE-3781742) and U.S. Pat. No. 4,734,518], or a manner such that the reaction is performed in a tubular reactor having a heterogeneous catalyst securely placed therein [see Unexamined Japanese Patent Application Laid-Open Specification No. 63-238043 and Unexamined Japanese Patent Application Laid-Open Specification No. 64-31737 (corresponding to U.S. Pat. No. 4,691,041, EP-298167B1 and DE-3781796G)].

The reactive distillation method (4) is a method in which each of ethylene carbonate and methanol is continuously fed to a multi-stage distillation column to perform a reaction in a plurality of stages of the distillation column in the presence of a catalyst, while continuously separating the produced dimethyl carbonate from the produced ethylene glycol [see Unexamined Japanese Patent Application Laid-Open Specification No. 4-198141, Unexamined Japanese Patent Application Laid-Open Specification No. 4-230243, Unexamined Japanese Patent Application Laid-Open Specification No. 5-213830 (corresponding to DE-4129316A1, U.S. Pat. No. 5,231,212 and EP-530615A3) and Unexamined Japanese Patent Application Laid-Open Specification No. 6-9507 (corresponding to U.S. Pat. No. 5,359,118, EP-569812A1 and DE-4216121A1)].

However, the above-mentioned conventional methods (1) to (4) have their respective problems as described below.

In the case of each of the complete batchwise method (1) and the flow method (3) using a tubular reactor, it is impossible to achieve a higher conversion of ethylene carbonate than the conversion of ethylene carbonate at the equilibrium state of reaction (the latter conversion is dependent on the composition ratio of the feedstocks fed to the reactor and the reaction temperature). For example, in Example 1 of Unexamined Japanese Patent Application Laid-Open Specification No. 63-41432 (corresponding to U.S. Pat. No. 4,661,609, EP-255252B1 and DE-3781742G) which is directed to a continuous flow reaction method using a tubular reactor, the flow reaction is conducted at 130° C. using a feedstock mixture having a methanol/ethylene carbonate molar ratio of 4/1. As a result, the conversion of ethylene carbonate is only 25%. This means that large amounts of unreacted ethylene carbonate and unreacted methanol, which are contained in the reaction mixture, must be separated and recovered, which in turn are recycled to the reactor. Actually, in the method disclosed in Unexamined Japanese Patent Application Laid-Open Specification No. 64-31737 (corresponding to U.S. Pat. No. 4,691,041, EP-298167B1 and DE-3781796G), various equipment is used for the separation, purification, recovery and recycling of the unreacted compounds.

Further, in methods (1) and (3), the presence of an azeotropic mixture of ethylene carbonate and ethylene glycol in the reaction system causes the following problems.

When the conversion of ethylene carbonate is less than 100% in either method (1) or method (3), the resultant liquid reaction mixture inevitably contains both ethylene carbonate and ethylene glycol. In order to obtain high purity ethylene glycol from such a reaction mixture, the produced ethylene glycol is generally separated by distillation. If the distillation is conducted under a pressure of 9,600 Pa or more, the formation of the azeotropic mixture can be avoided, so that the unreacted ethylene carbonate seems to be able to be separated from the mixture containing the unreacted ethylene carbonate and the ethylene glycol by distillation only. However, when this distillation under such a high pressure is conducted at a relatively high temperature, the ethylene glycol unfavorably accelerates the decomposition of ethylene carbonate. Therefore, it is generally required to conduct the distillation at a moderate temperature, i.e., 150° C. or below, under reduced pressure, so that the formation of the azeotropic mixture inevitably occurs (McKetta, "Encyclopedia of Chemical Processing and Design" vol. 20, p. 194, published by Marcel Dekker Co., 1984). Therefore, with the distillation method, it is difficult to constantly and stably recover the unreacted ethylene carbonate from the reaction mixture containing the unreacted ethylene carbonate and the produced ethylene glycol. For developing a new method capable of separating ethylene glycol from the azeotropic mixture without suffering the above-mentioned problems, various proposals have conventionally been made. For example, in the method described in Example 50 of Unexamined Japanese Patent Application Laid-Open Specification No. 64-31737 (corresponding to U.S. Pat. No. 4,691,041, EP-298167B1 and DE-3781796G), the reaction mixture flowing out from the reaction vessel is subjected to distillation in distillation column (B), thereby separating the reaction mixture into a low boiling point mixture comprising methanol and dimethyl carbonate and a column bottom liquid comprising ethylene glycol and ethylene carbonate. The obtained column bottom liquid is subjected to distillation in distillation column (D), thereby separating the previous column bottom liquid into another column bottom liquid comprising ethylene carbonate and an ethylene glycol/ethylene carbonate azeotropic mixture. Then, the obtained column bottom liquid comprising ethylene carbonate is recycled to the reaction vessel, and the ethylene carbonate contained in the ethylene glycol/ethylene carbonate azeotropic mixture is converted to ethylene glycol by hydrolysis. However, in this method, the methanol/ethylene carbonate molar ratio in the reaction system is in the range of 3 to 6 as in the conventional method in the art and, hence, the conversion of the ethylene carbonate is as low as 25 to 60%, and the weight ratio of the unreacted ethylene carbonate recycled to the reaction vessel to the converted ethylene carbonate is as high as 0.6 to 2.9. Therefore, this method is disadvantageous not only in that a large amount of energy is needed for the recycling of the unreacted ethylene carbonate, but also in that a large amount of the ethylene carbonate is consumed by the side reactions, leading to a loss of ethylene carbonate.

As described below in detail, the method (2) using a reaction vessel provided at an upper portion thereof with a distillation column has problems in that the reaction must be conducted for a prolonged period of time and, therefore, a large amount of methanol needs to be used for preventing the lowering of the selectivity for the desired products.

In method (2), in order to compensate for the methanol distilled as an azeotropic mixture of the methanol and the produced dimethyl carbonate, the continuous or batchwise addition of supplemental methanol to the reaction vessel is optionally conducted. However, irrespective of whether or not such an addition of supplemental methanol is conducted, the reaction per se is performed only in a batch-type reaction vessel. That is, in this method, the reaction is batchwise performed under reflux for a prolonged period of time as long as 3 to 20 hours.

In this method, the dimethyl carbonate, which is one of the reaction products, is continuously withdrawn out of the reaction system, whereas the ethylene glycol, which is another reaction product, remains together with the unreacted ethylene carbonate in the reaction system containing the catalyst for a long period of time. This long residence time of the ethylene glycol and the ethylene carbonate in the reaction system causes side reactions to produce polyethylene glycols, such as diethylene glycol and triethylene glycol. For preventing the occurrence of such side reactions and the lowering of the selectivity for the desired products, it is necessary to use a large excess of methanol, relative to the amount of the ethylene carbonate which is batchwise fed to the reaction vessel. In fact, in the conventionally proposed methods, the following examples are noted in which a large excess of methanol is used; that is, use is made of methanol in excess amounts (in terms of the number of moles of methanol per mole of ethylene carbonate or propylene carbonate), such as 14 moles (U.S. Pat. No. 3,803,201), 17 moles (Unexamined Japanese Patent Application Laid-Open Specification No. 1-311054), 22 moles [Unexamined Japanese Patent Application Laid-Open Specification No. 51-122025 (corresponding to U.S. Pat. No. 4,062,884 and DE-2615665B)], and 23 moles [Unexamined Japanese Patent Application Laid-Open Specification No. 54-48716 (corresponding to U.S. Pat. No. 4,307,032, EP-1083B and DE-28601426)].

In the case of the reactive distillation method (4), it is possible to perform a reaction with high conversion, as compared to the methods (1), (2) and (3). In fact, it has been reported that, when the reactive distillation is conducted using a large amount of pure methanol (containing no dimethyl carbonate), relative to the amount of ethylene carbonate, i.e., an amount such that the methanol/ethylene carbonate molar ratio is 9 to 10, the conversion of the ethylene carbonate reaches 100% [see Example 1 of Unexamined Japanese Patent Application Laid-Open Specification No. 4-198141 and Example 11 of Unexamined Japanese Patent Application Laid-Open Specification No. 5-213830 (corresponding to U.S. Pat. No. 5,231,212, EP-530615A3 and DE-4129316A1)]. However, there has conventionally been no report such that, when impure methanol containing dimethyl carbonate is used instead of pure methanol, dimethyl carbonate or ethylene glycol can be produced in a yield higher than 80%.

In the method (4), the produced dimethyl carbonate is distilled from the distillation column as a low boiling point product together with the unreacted methanol. Dimethyl carbonate and methanol form an azeotropic mixture. Therefore, the separation of the produced dimethyl carbonate from the gaseous reaction mixture distilled from the distillation column is conducted by special separation methods, such as distillation method conducted under pressure [Unexamined Japanese Patent Application Laid-Open Specification No. 51-108019 (corresponding to DE-2607003B)]. Generally, by this method, dimethyl carbonate containing no methanol can be obtained, whereas, however, methanol is obtained only in the form of a mixture thereof with dimethyl carbonate. Therefore, it is difficult to obtain pure methanol containing substantially no dimethyl carbonate. For example, in the Examples of the above-mentioned Unexamined Japanese Patent Application Laid-Open Specification No. 51-108019 (corresponding to DE-2607003B), a methanol/dimethyl carbonate mixture (weight ratio: 70/30) is separated by distillation, and pure dimethyl carbonate is obtained as a column bottom product. However, as a product distilled from the column top, only a methanol/dimethyl carbonate mixture (weight ratio: 95/5) is obtained.

As can be seen from the above, for obtaining pure methanol, an additional separation process needs to be conducted. Therefore, from the viewpoint of commercial scale practice of the production of dimethyl carbonate, it has been strongly desired to develop a method in which the methanol/dimethyl carbonate mixture as such can be used as a feedstock instead of pure methanol.

However, heretofore, almost no technique has been known, in which a methanol/dimethyl carbonate mixture alone is used as a feedstock in method (4) except for the method described in Example 5 of Unexamined Japanese Patent Application Laid-Open Specification No. 5-213830 (corresponding to U.S. Pat. No. 5,231,212, EP-530615A3 and DE-4129316A1). However, in Example 5 of this Unexamined Japanese Patent Application Laid-Open Specification No. 5-213830, in which a methanol/dimethyl carbonate mixture (weight ratio: 70/30) is used, the conversion of ethylene carbonate is only 62.8% (calculated from the data of the composition of the product mixture obtained at the column bottom). The reason for such poor conversion resides in that, since the reaction between ethylene carbonate and methanol is an equilibrium reaction, the presence of dimethyl carbonate (which is a reaction product of the above reaction) in the reaction system causes the lowering of the conversion of the ethylene carbonate. Therefore, this method has a problem such that the larger the amount of dimethyl carbonate recycled to the reaction system, the longer the reaction time (residence time) required for achieving a desired conversion and the larger the amount of methanol required for achieving a desired conversion.

For achieving a complete conversion of ethylene carbonate in method (4) in which a methanol/dimethyl carbonate mixture is occasionally used as a feedstock, pure methanol needs to be supplied in addition to the methanol/dimethyl carbonate mixture as in Unexamined Japanese Patent Application Laid-Open Specification No. 6-9507 (corresponding to U.S. Pat. No. 5,359,118).

However, when the methanol/dimethyl carbonate mixture is used in combination with pure methanol, in addition to the main operation for obtaining the desired products, a complicated operation to separate the methanol/dimethyl carbonate azeotropic mixture for obtaining pure methanol containing substantially no dimethyl carbonate needs to be conducted [for example, such an operation needs to be conducted using, in combination, two distillation columns which have different operation pressures (see Unexamined Japanese Patent Application Laid-Open Specification No. 2-212456)]. In fact, in the above-mentioned Unexamined Japanese Patent Application Laid-Open Specification No. 6-9507 (corresponding to U.S. Pat. No. 5,359,118, EP-569812A1 and DE-421621A1), pure methanol is obtained by the above-mentioned additional complicated operation and used.

Further, in method (4), since the dimethyl carbonate and the ethylene glycol are produced by a reversible equilibrium reaction between ethylene carbonate and methanol, even when a 100% conversion of ethylene carbonate is achieved by using pure methanol, the produced ethylene glycol inevitably contains even a small amount of the unreacted ethylene carbonate. Therefore, for obtaining highly purified ethylene glycol, the produced ethylene glycol must be subjected to fractionation.

Further, even when pure methanol is used in method (4), the following problem arises. In method (4), unreacted ethylene carbonate is recovered by subjecting the column bottom liquid containing the produced ethylene glycol and the unreacted ethylene carbonate to distillation. As mentioned above, since the distillation for separating the ethylene carbonate under high temperature conditions should be avoided, the distillation must be carried out under moderate conditions such that an ethylene glycol/ethylene carbonate azeotropic mixture is inevitably formed with disadvantages. The formed ethylene glycol/ethylene carbonate azeotropic mixture is a minimum boiling point azeotropic mixture having a high ethylene glycol content (ethylene carbonate/ ethylene glycol weight ratio: 14/86, under the operation pressure of 10 torr). Therefore, simultaneously with the recycling of the unreacted ethylene carbonate to the reaction system, a large amount of the produced ethylene glycol also is recycled to the reaction system together with the ethylene carbonate. The ethylene glycol recycled to the reaction system unfavorably affects the equilibrium of the reaction, thereby lowering the productivity.

As can be understood from the above, no proposal has heretofore been made with respect to the method for producing a dialkyl carbonate and a high purity diol, each with high productivity, by using as a feedstock an aliphatic monohydric alcohol containing a concomitant dialkyl carbonate.

SUMMARY OF THE INVENTION

The present inventors have made extensive and intensive studies with a view toward developing a method for continuously producing a dialkyl carbonate and a high purity diol with high productivity, in which not only a pure aliphatic monohydric alcohol but also an aliphatic monohydric alcohol containing a concomitant dialkyl carbonate can be used as a feedstock aliphatic monohydric alcohol, and which is free from the above-mentioned problems accompanying the prior art. As a result, it has unexpectedly been found that when a method is continuously conducted which comprises: (1) feeding a cyclic carbonate and an aliphatic monohydric alcohol to a continuous multi-stage distillation column and effecting a transesterification between the cyclic carbonate and the aliphatic monohydric alcohol in the presence of a catalyst in at least one reaction zone selected from the multi-stage distillation column and at least one transesterification reactor which is disposed outside of the multi-stage distillation column and which communicates fluid-tightly with the multi-stage distillation column so that a liquid flowing-down inside the distillation column can be continuously introduced to the transesterification reactor and the resultant reaction mixture can be continuously recycled to the distillation column, while continuously withdrawing a low boiling point mixture containing the produced dialkyl carbonate in a gaseous form from an upper portion of the distillation column and continuously withdrawing a high boiling point mixture containing the produced diol and unreacted cyclic carbonate in a liquid form from a lower portion of the distillation column: and (2) continuously feeding water and the high boiling point mixture withdrawn from a lower portion of the distillation column to a continuous hydrolysis reactor, thereby continuously hydrolyzing the unreacted cyclic carbonate to convert it to a diol and carbon dioxide, it becomes possible to produce a dialkyl carbonate and a high purity diol, each with high productivity, even when an aliphatic monohydric alcohol containing a concomitant dialkyl carbonate in an amount up to 40% by weight is used as a feedstock aliphatic monohydric alcohol. The present invention has been made, based on these novel findings.

Accordingly, it is a primary object of the present invention to provide a novel method for continuously producing a dialkyl carbonate and a high purity diol, each with high productivity, in which a cyclic carbonate and an alcohol selected from a pure aliphatic monohydric alcohol and an aliphatic monohydric alcohol containing a concomitant dialkyl carbonate are used as feedstocks.

The foregoing and other objects, features and advantages of the present invention will be apparent from the following detailed description and appended claims taken in connection with the accompanying drawings.

Figure 1:
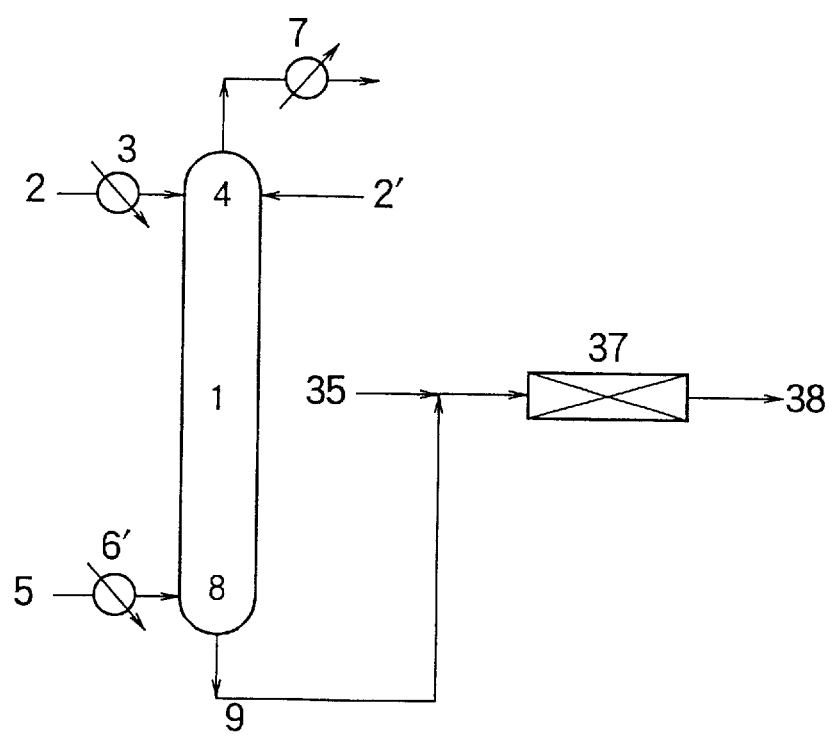
FIG. 1 is a diagram showing the system which was used for practicing Example 1 of the present application.

DESCRIPTION OF REFERENCE NUMERALS 1 continuous multi-stage distillation column

| | |
|---|---|
| 2, 2' | conduit |
| 3 | preheater |
| 4 | upper portion of column |
| 5, 5' | conduit |
| 6 | reboiler |
| 6' | evaporator |
| 7 | condenser |
| 8 | lower portion of column |
| 9 | conduit |
| 10 | low boiling point mixture-separating column |
| 11 | upper portion of column |
| 12 | conduit |
| 13 | condenser |
| 14 | conduit |
| 15 | evaporator |
| 16 | lower portion of column |
| 17 | conduit |
| 18 | reboiler |
| 19 | conduit |
| 20 | conduit |
| 21 | condenser |
| 22 | conduit |
| 23 | diol-separating column |
| 24 | upper portion of column |
| 25 | conduit |
| 26 | condenser |
| 27 | conduit |
| 28 | lower portion of column |
| 29 | conduit |
| 30 | reboiler |
| 31 | conduit |
| 32 | conduit |
| 33 | condenser |
| 34 | conduit |
| 35 | conduit |
| 36 | conduit |
| 37 | continuous hydrolysis reactor |
| 38 | conduit |
| 39 | gas-liquid separator |
| 40 | conduit |
| 41 | conduit |
| 42 | conduit |
| 43 | continuous hydrolysis column |
| 45 | conduit |
| 47 | azeotropic mixture-separating column |
| 50 | distillation column |
| 61 | inlet |
| 62 | withdrawal port provided in side wall |
| 63 | inlet |
| 64 | withdrawal port provided in side wall |
| 65 | inlet |
| 66 | withdrawal port provided in side wall |
| 67 | inlet |
| 68 | withdrawal port provided in side wall |
| A | transesterification reactor |
| B | transesterification reactor |
| C | transesterification reactor |
| D | transesterification reactor |

DETAILED DESCRIPTION OF THE INVENTION

In the present invention, there is provided a method for continuously producing a dialkyl carbonate and a diol from a cyclic carbonate and an aliphatic monohydric alcohol, comprising:

(1) continuously feeding a cyclic carbonate represented by the following formula (A):

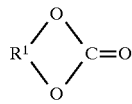

(A)

wherein $R^1$ is a divalent group represented by the formula $-(CH_2)_m-$, wherein m is an integer of from 2 to 6, which is unsubstituted or substituted with at least one substituent selected from the group consisting of a $C_1$–$C_{10}$ alkyl group and a $C_6$–$C_{10}$ aryl group, and an aliphatic monohydric alcohol represented by the following formula (B):

$$R^2OH \qquad (B)$$

wherein $R^2$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group, to a continuous multi-stage distillation column, wherein the aliphatic monohydric alcohol contains a concomitant dialkyl carbonate in an amount of from 0 to 40% by weight, based on the total weight of the aliphatic monohydric alcohol and the concomitant dialkyl carbonate, and continuously effecting a transesterification between the cyclic carbonate and the aliphatic monohydric alcohol in the presence of a transesterification catalyst in at least one reaction zone selected from the group consisting of (a) the multi-stage distillation column, and (b) at least one transesterification reactor which is disposed outside of the multi-stage distillation column and which has an inlet and an outlet, each fluid-tightly communicating with the multi-stage distillation column, thereby continuously producing a dialkyl carbonate and a diol, while continuously withdrawing a low boiling point mixture containing the produced dialkyl carbonate in a gaseous form from an upper portion of the multi-stage distillation column and continuously withdrawing a high boiling point mixture containing the produced diol and unreacted cyclic carbonate in a liquid form from a lower portion of the multi-stage distillation column, wherein when the transesterification is conducted in the transesterification reactor, a liquid flowing-down inside the multi-stage distillation column is continuously withdrawn through at least one withdrawal port provided in a side wall of the multi-stage distillation column at a position or positions thereof corresponding to a stage or stages selected from the group consisting of intermediate stages and a lowermost stage of the multi-stage distillation column, and the withdrawn liquid is continuously introduced to the transesterification reactor through the inlet thereof to thereby contact the cyclic carbonate and aliphatic monohydric alcohol contained in the withdrawn liquid with the transesterification catalyst and effect a transesterification between the cyclic carbonate and the aliphatic monohydric alcohol, whereupon the resultant reaction mixture is continuously withdrawn from the at least one transesterification reactor through the outlet thereof and recycled to the multi-stage distillation column through an introduction port provided in the side wall of the multi-stage distillation column at a position above the or each withdrawal port; and (2) continuously feeding water and the high boiling point mixture withdrawn from the lower portion of the multistage distillation column in step (1) to a continuous hydrolysis reactor, to thereby effect a continuous hydrolysis of the unreacted cyclic carbonate and produce a diol and carbon dioxide, while continuously withdrawing the resultant hydrolysis reaction mixture containing the produced diol from the continuous hydrolysis reactor.

For an easy understanding of the present invention, the essential features and various preferred embodiments of the present invention are enumerated below.

1. A method for continuously producing a dialkyl carbonate and a diol from a cyclic carbonate and an aliphatic monohydric alcohol, comprising:

(1) continuously feeding a cyclic carbonate represented by the following formula (A):

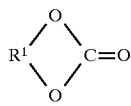
(A)

wherein $R^1$ is a divalent group represented by the formula $-(CH_2)_m-$, wherein m is an integer of from 2 to 6, which is unsubstituted or substituted with at least one substituent selected from the group consisting of a $C_1$–$C_{10}$ alkyl group and a $C_6$–$C_{10}$ aryl group, and an aliphatic monohydric alcohol represented by the following formula (B):

$R^2OH$ (B)

wherein $R^2$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group, to a continuous multi-stage distillation column, wherein the aliphatic monohydric alcohol contains a concomitant dialkyl carbonate in an amount of from 0 to 40% by weight, based on the total weight of the aliphatic monohydric alcohol and the concomitant dialkyl carbonate, and continuously effecting a transesterification between the cyclic carbonate and the aliphatic monohydric alcohol in the presence of a transesterification catalyst in at least one reaction zone selected from the group consisting of (a) the multi-stage distillation column, and (b) at least one transesterification reactor which is disposed outside of the multi-stage distillation column and which has an inlet and an outlet, each fluid-tightly communicating with the multi-stage distillation column, thereby continuously producing a dialkyl carbonate and a diol, while continuously withdrawing a low boiling point mixture containing the produced dialkyl carbonate in a gaseous form from an upper portion of the multi-stage distillation column and continuously withdrawing a high boiling point mixture containing the produced diol and unreacted cyclic carbonate in a liquid form from a lower portion of the multi-stage distillation column, wherein when the transesterification is conducted in the transesterification reactor, a liquid flowing-down inside the multi-stage distillation column is continuously withdrawn through at least one withdrawal port provided in a side wall of the multi-stage distillation column at a position or positions thereof corresponding to a stage or stages selected from the group consisting of intermediate stages and a lowermost stage of the multi-stage distillation column, and the withdrawn liquid is continuously introduced to the transesterification reactor through the inlet thereof to thereby contact the cyclic carbonate and aliphatic monohydric alcohol contained in the withdrawn liquid with the transesterification catalyst and effect a transesterification between the cyclic carbonate and the aliphatic monohydric alcohol, whereupon the resultant reaction mixture is continuously withdrawn from the at least one transesterification reactor through the outlet thereof and recycled to the multi-stage distillation column through an introduction port provided in the side wall of the multi-stage distillation column at a position above the or each withdrawal port; and (2) continuously feeding water and the high boiling point mixture withdrawn from the lower portion of the multi-stage distillation column in step (1) to a continuous hydrolysis reactor, to thereby effect a continuous hydrolysis of the unreacted cyclic carbonate and produce a diol and carbon dioxide, while continuously withdrawing the resultant hydrolysis reaction mixture containing the produced diol from the continuous hydrolysis reactor.

2. The method according to item 1, wherein the conversion of the cyclic carbonate in step (1) is from 80 to 99%.

3. The method according to item 1 or 2, wherein, in step (1), the cyclic carbonate in a liquid form is continuously fed to an upper portion of the continuous multi-stage distillation column, and the aliphatic monohydric alcohol in a gaseous form is continuously fed to a lower portion of the continuous multi-stage distillation column.

4. The method according to any one of items 1 to 3, wherein, in step (2), the continuous hydrolysis of the unreacted cyclic carbonate is conducted in the presence of at least one hydrolysis catalyst selected from the group consisting of a solid catalyst and a homogeneous catalyst.

5. The method according to any one of items 1 to 4, wherein the high boiling point mixture withdrawn from a lower portion of the continuous multi-stage distillation column in step (1) contains the aliphatic monohydric alcohol and the dialkyl carbonate, and wherein the high boiling point mixture is continuously introduced, prior to the feeding thereof to the continuous hydrolysis reactor in step (2), to a low boiling point mixture-separating column which is comprised of a continuous multi-stage distillation column, and wherein a low boiling point mixture containing the aliphatic monohydric alcohol and the dialkyl carbonate which are contained in the high boiling point mixture is continuously withdrawn from an upper portion of the low boiling point mixture-separating column, while continuously withdrawing a high boiling point mixture containing the unreacted cyclic carbonate and the diol from a lower portion of the low boiling point mixture-separating column, wherein the low boiling point mixture withdrawn from the upper portion of the low boiling point mixture-separating column is continuously recycled to the multi-stage distillation column used in step (1), while continuously feeding the high boiling point mixture withdrawn from the low boiling point mixture-separating column to the continuous hydrolysis reactor used in step (2).

6. The method according to any one of items 1 to 5, wherein the continuous hydrolysis reactor is selected from the group consisting of a tube reactor and a vessel reactor, and wherein the produced hydrolysis reaction mixture containing the diol and the carbon dioxide is continuously introduced to a diol-separating column which is comprised of a continuous multi-stage distillation column and wherein the diol is continuously withdrawn from a lower portion of the diol-separating column, while continuously withdrawing a low boiling point mixture containing the carbon dioxide from an upper portion of the diol-separating column.

7. The method according to item 5, wherein the continuous hydrolysis reactor is a hydrolysis column comprised of a continuous multi-stage distillation column, and wherein a high boiling point mixture containing the diol is withdrawn from a lower portion of the continuous hydrolysis column, while continuously withdrawing a low boiling point mixture containing the carbon dioxide from an upper portion of the continuous hydrolysis column.

8. The method according to item 7, wherein the high boiling point mixture withdrawn from the lower portion of the low boiling point mixture-separating column is continuously introduced to the continuous hydrolysis column through an introduction port provided in a side wall of the hydrolysis column at a position above a withdrawal port provided in a side wall of the continuous hydrolysis column for withdrawing the diol.

9. The method according to item 7 or 8, wherein the water is continuously introduced to the continuous hydrolysis column at a position above the withdrawal port for withdrawing the diol.

10. The method according to item 5 or 8, wherein the cyclic carbonate is capable of forming a minimum boiling point azeotropic mixture with the diol, and wherein the high boiling point mixture withdrawn from the lower portion of the low boiling point mixture-separating column is continuously introduced to an azeotropic mixture-separating column prior to the feeding of the high boiling point mixture to the continuous hydrolysis reactor, while continuously withdrawing the diol from a lower portion of the azeotropic mixture-separating column and continuously withdrawing a low boiling point mixture containing the minimum boiling point azeotropic mixture of the cyclic carbonate with the diol from an upper portion of the azeotropic mixture-separating column, and wherein the low boiling point mixture withdrawn from the upper portion of the azeotropic mixture-separating column is introduced to the continuous hydrolysis reactor to effect a hydrolysis reaction and obtain a hydrolysis reaction mixture.

11. The method according to item 10, wherein the hydrolysis reaction mixture is recycled to the azeotropic mixture-separating column.

12. The method according to any one of items 1 to 4, wherein the high boiling point mixture withdrawn from a lower portion of the continuous multi-stage distillation column in step (1) contains the aliphatic monohydric alcohol and the dialkyl carbonate, wherein the continuous hydrolysis reactor is a continuous hydrolysis column comprised of a continuous multi-stage distillation column, and wherein a low boiling point mixture containing the monohydric alcohol, the dialkyl carbonate and the carbon dioxide is continuously withdrawn from an upper portion of the continuous hydrolysis column and recycled to the continuous multi-stage distillation column used in step (1), while continuously withdrawing the diol from a lower portion of the continuous hydrolysis column.

13. The method according to item 12, wherein the carbon dioxide or both of the carbon dioxide and the water are removed from the low boiling point mixture withdrawn from the upper portion of the continuous hydrolysis column prior to the recycling of the low boiling point mixture to the continuous multi-stage distillation column used in step (1).

14. The method according to item 12 or 13, wherein the high boiling point mixture withdrawn from the lower portion of the continuous multi-stage distillation column used in step (1) is fed to the continuous hydrolysis column at a position above a withdrawal port provided in a side wall of the continuous hydrolysis column for withdrawing the diol.

15. The method according to any one of items 1 to 14, wherein the cyclic carbonate is ethylene carbonate and the aliphatic monohydric alcohol is selected from the group consisting of methanol, ethanol, n-propanol, isopropanol, n-butanol, iso-butanol, sec-butanol and tert-butanol.

16. The method according to item 15, wherein the cyclic carbonate is ethylene carbonate and the aliphatic monohydric alcohol is methanol.

The method of the present invention is advantageous not only in that it becomes possible to efficiently perform the reaction to obtain the desired products with high productivity, as compared to the conventional methods, such as a method using a continuous multi-stage distillation column only, but also in that a high purity diol can be obtained. The reason for such advantages is considered to be as follows.

In the present invention, as mentioned above, in the continuous production of a dialkyl carbonate and a diol from a cyclic carbonate and an aliphatic monohydric alcohol, a cyclic carbonate and an aliphatic monohydric alcohol containing 0 to 40% by weight of a concomitant dialkyl carbonate are continuously fed to a continuous multi-stage distillation column, and a transesterification between the cyclic carbonate and the aliphatic monohydric alcohol is continuously effected in the presence of a transesterification catalyst in at least one reaction zone selected from the group consisting of (a) the multi-stage distillation column and (b) at least one transesterification reactor which is disposed outside of the multi-stage distillation column and which has an inlet and an outlet, each fluid-tightly communicating with the multi-stage distillation column. Hereinbelow, for the sake of convenience in explanation, the above-mentioned mode in which multi-stage distillation column (a) is used for the transesterification reaction is frequently referred to simply as "reaction mode (a)", and the above-mentioned mode in which the transesterification reactor which is disposed outside the multistage distillation column is used for the transesterification reaction is frequently referred to simply as "reaction mode (b)".

More specifically, reaction modes (a) and (b) are defined as follows:

Reaction mode (a): a reaction mode in which the aliphatic monohydric alcohol and the cyclic carbonate are brought into contact with the transesterification catalyst in the multi-stage distillation column, to thereby effect a transesterification between the cyclic carbonate and the aliphatic monohydric alcohol in the multi-stage distillation column; and Reaction mode (b): a reaction mode in which a liquid flowing-down inside the multi-stage distillation column is withdrawn through at least one withdrawal port provided in a side wall of the multi-stage distillation column at a position or positions thereof corresponding to a stage or stages selected from the group consisting of intermediate stages and a lowermost stage of the multi-stage distillation column, and the withdrawn liquid is introduced to the transesterification reactor which is disposed outside of the multi-stage distillation column to thereby contact the cyclic carbonate and aliphatic monohydric alcohol contained in the withdrawn liquid with the transesterification catalyst and effect a transesterification between the cyclic carbonate and the aliphatic monohydric alcohol, whereupon the resultant reaction mixture is withdrawn from the transesterification reactor through the outlet thereof and recycled to the multi-stage distillation column through an introduction port provided in the side wall of the multi-stage distillation column at a position above the or each withdrawal port.

In the present invention, as mentioned above, reaction modes (a) and (b) may be used in combination.

In the present invention, when reaction mode (a) is used in step (1), the term "productivity" means a yield per unit volume of the reaction zone in continuous multi-stage distillation column (a) and per unit time in step (1), i.e., a space time yield in a reaction zone of continuous multi-stage distillation column (a) in step (1). When a plurality of continuous multi-stage distillation columns are used, the total volume of the continuous multi-stage distillation columns is used for calculation of the above-mentioned yield. When only reaction mode (b) is used and reaction mode (a) is not used in step (1), the term "productivity" means a yield per unit volume of transesterification reactor (b) used in reaction mode (b) and per unit time in step (1), i.e., a space time yield in transesterification reactor (b) in step (1). When a plurality of transesterification reactors are used, the total volume of the transesterification reactors is used for calculation of the above-mentioned yield. When reaction mode (b) is used in step (1) and the transesterification reaction proceeds in the continuous multi-stage distillation column also in step (1), the term "productivity" means a value obtained by dividing a yield per unit time in step (1) by the total volume of the respective reaction zones of transesterification reactor (b) in step (1) and continuous multi-stage distillation column (a) in step (1).

The reaction performed in the present invention is a reversible, equilibrium transesterification reaction represented by the following formula (I), in which a dialkyl carbonate (C) and a diol (D) are produced from a cyclic carbonate (A) and an aliphatic monohydric alcohol (B):

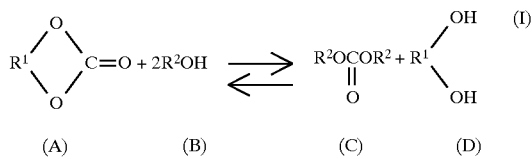

wherein:
- $R^1$ is a divalent group represented by formula —$(CH_2)_m$—, wherein m is an integer of from 2 to 6, which is unsubstituted or substituted with at least one substituent selected from the group consisting of a $C_1$–$C_{10}$ alkyl group and a $C_6$–$C_{10}$ aryl group; and
- $R^2$ represents a monovalent aliphatic $C_1$–$C_{12}$ group which is unsubstituted or substituted with at least one substituent selected from the group consisting of a $C_1$–$C_{10}$ alkyl group and a $C_6$–$C_{10}$ aryl group.

The above-mentioned transesterification reaction generally proceeds in a liquid phase. Therefore, for achieving a high conversion, it is necessary to remove the produced dialkyl carbonate or diol, whichever has a lower boiling point, as much as possible from the liquid reaction mixture.

However, in conventional techniques using reactive distillation which are disclosed in prior art references [see Unexamined Japanese Patent Application Laid-Open Specification No. 5-213830 (corresponding to EP530615A3, U.S. Pat. No. 5,231,212 and DE-4129316A1) and Unexamined Japanese Patent Application Laid-Open Specification No. 6-9507 (corresponding to EP-569812A1, U.S. Pat. No. 5,359,118 and DE-4216121A1)], when it is attempted to achieve a substantially 100% conversion of the cyclic carbonate in one pass, a large amount of aliphatic monohydric alcohol needs to be used, so that the productivity inevitably becomes poor. Illustratively stated, the higher becomes the concentration of a diol in the reaction system with the progress of the reaction, the higher the rate of the reverse reaction becomes. Therefore, the higher the desired conversion of the cyclic carbonate, the larger the amount of aliphatic monohydric alcohol required for shifting the equilibrium of the reaction toward the product system. Further, in the reactive distillation techniques disclosed in the above-mentioned prior art references, for achieving a substantially 100% conversion of the cyclic carbonate, it is necessary to use a pure aliphatic monohydric alcohol as a feedstock. In addition, as mentioned above, even when a pure aliphatic monohydric alcohol is used, the produced diol inevitably contains a small amount of unreacted cyclic carbonate. Therefore, as mentioned above, for obtaining a high purity diol, the produced diol must be subjected to high precision fractionation. On the other hand, when the conversion of a cyclic carbonate in one pass is lowered by adopting the above-mentioned reactive distillation, an additional separation process comprising isolation-recovery and recycling of the unreacted cyclic carbonate becomes necessary. Generally, such a separation process is conducted using distillation columns. For example, in the production of dimethyl carbonate and ethylene glycol from ethylene carbonate and methanol, a reaction mixture is subjected to distillation in a first distillation column, to thereby obtain a methanol/dimethyl carbonate mixture from the top of the distillation column, while obtaining an ethylene glycol/ethylene carbonate mixture from the bottom of the distillation column. The obtained ethylene glycol/ethylene carbonate mixture is further subjected to distillation under reduced pressure in a second distillation column, to thereby obtain a minimum boiling point azeotropic mixture of ethylene glycol and ethylene carbonate from the top of the distillation column. In the above-mentioned process, (i) when the ethylene glycol/ethylene carbonate weight ratio in the liquid reaction mixture obtained by the reactive distillation is larger than the ethylene glycol/ethylene carbonate weight ratio of the azeotropic mixture distilled from the second distillation column, the ethylene glycol is obtained from the bottom of the second distillation column, whereas, (ii) when the ethylene glycol/ethylene carbonate weight ratio in the liquid reaction mixture in the first distillation column is smaller than the ethylene glycol/ethylene carbonate weight ratio of the azeotropic mixture distilled from the second distillation column, the ethylene carbonate is obtained from the bottom of the second distillation column. In the case of (i) above, as mentioned above, a part of the produced ethylene glycol is distilled in the form of a minimum boiling point azeotropic mixture of the ethylene glycol and the unreacted ethylene carbonate. Therefore, when the unreacted ethylene carbonate is recycled to the transesterification reaction system, the produced ethylene glycol is necessarily recycled together with the ethylene carbonate. As a result, the equilibrium of the transesterification reaction is unfavorably affected, thereby lowering the productivity. With respect to this unfavorable recycling of the produced ethylene glycol, the lower the conversion of the ethylene carbonate, the larger the amount of the produced ethylene glycol recycled to the reaction system. For example, when the transesterification reaction is conducted under a pressure of 1,300 Pa (10 torr), the ethylene glycol/ethylene carbonate weight ratio is 86/14. Therefore, in this instance, even when the conversion of ethylene carbonate is as high as 99%, 9% of the produced ethylene glycol forms an azeotropic mixture with the unreacted ethylene carbonate. When the conversion of ethylene carbonate is 96%, 36% of the produced ethylene glycol forms an azeotropic mixture with the unreacted ethylene carbonate. Further, when the conversion of ethylene carbonate is 90%, an extremely large amount as high as 97% of the produced ethylene glycol forms an azeotropic mixture with the unreacted ethylene carbonate to be recycled to the reaction system. In the case of (ii) above, the conversion of ethylene carbonate is as low as 89% or less. Therefore, the produced ethylene glycol is obtained only in the form of a minimum boiling point azeotropic mixture of the ethylene glycol with the unreacted ethylene carbonate. Further, in this instance, when a cyclic carbonate is heated in the absence of a monofunctional aliphatic monohydric alcohol, by-products, such as an aliphatic polycarbonate, an aliphatic polyether and a high boiling point diol, are likely to be formed, so that the selectivity for the desired products is lowered. This problem is serious especially when the cyclic carbonate is heated in the absence of the monofunctional aliphatic monohydric alcohol and in the presence of a transesterification catalyst.

Therefore, in the conventional techniques using reactive distillation, it has been usually attempted to avoid the above-mentioned disadvantages by using a large excess of pure methanol containing no dialkyl carbonate so as to increase the conversion of the cyclic carbonate as much as possible.

On the other hand, by the method of the present invention, in which a transesterification is effected between the cyclic carbonate and the aliphatic monohydric alcohol in at least one reaction zone selected from the group consisting of (a) the multi-stage distillation column and (b) at least one transesterification reactor which is disposed outside of the multistage distillation column and which has an inlet and an outlet, each communicating with the multi-stage distillation column, it becomes possible not only to achieve the reduction of the necessary amount of an aliphatic monohydric alcohol but also use a small-sized reaction apparatus, without desperately attempting to increase the conversion of the cyclic carbonate. Further, in the method of the present invention, the unreacted cyclic carbonate is converted to a diol by hydrolysis, so that complicated operations for separating the cyclic carbonate from the diol/cyclic carbonate mixture are not needed. In addition, by the above-mentioned hydrolysis of the unreacted cyclic carbonate, a high purity diol containing no cyclic carbonate can be obtained.

Generally, ethylene glycol is produced by hydration of ethylene oxide. However, such a hydrolysis reaction is accompanied by side reactions due to the high reactivity of ethylene oxide to ethylene glycol, i.e., the addition reaction of the produced ethylene glycol with the unreacted ethylene oxide, thereby forming by-products, such as diethylene glycol and triethylene glycol. In the above hydration reaction, for example, the selectivity for ethylene glycol is only 89 to 91%, by-products, such as diethylene glycol as a main by-product, and triethylene glycol and tetraethylene glycol as other by-products are formed (see Encyclopedia of Chemical Technology vol. 12, p.700, L.15–19). In the current practice of the industry, ethylene glycol containing by-products, obtained in the manner as mentioned above, are subjected to distillation to obtain purified ethylene glycol. However, complete removal of impurities, such as diethylene glycol, is difficult, and commercially available ethylene glycol generally contains diethylene glycol in an amount as large as several tens to several hundreds of ppm. On the other hand, by the method of the present invention, no ethylene oxide is used and, therefore, almost no by-production of diethylene glycol occurs. As a result, a high purity diol containing no diethylene glycol can be obtained.

Further, for example, when ethylene carbonate is used in the method of the present invention, the recycling of unreacted ethylene carbonate is not conducted. Therefore, the method of the present invention is free from the serious problems accompanying the conventional techniques, such as the lowering of the efficiency of the transesterification reaction caused by the recycling of the produced ethylene glycol in the form of an azeotropic mixture of the ethylene glycol and unreacted ethylene carbonate. The omission of the recycling of the azeotropic mixture of the ethylene glycol and the unreacted ethylene carbonate has for the first time become possible by the method of the present invention, in which a cyclic carbonate/aliphatic monohydric alcohol transesterification reaction using reactive distillation and a subsequent hydrolysis of unreacted cyclic carbonate are performed in combination.

In the present invention, the unreacted cyclic carbonate is converted to a diol. Therefore, the hydrolyzed cyclic carbonate does not contribute to the yield of dialkyl carbonate; however, instead, a high purity diol is produced as a result of the hydrolysis, so that the productivity on the whole including the production of not only a dialkyl carbonate but also a diol is not lowered by the above-mentioned hydrolysis of the cyclic carbonate.

In step (1) of the method of the present invention, the reaction is performed under conditions such that the conversion of cyclic carbonate is less than 100%. Therefore, in the method of the present invention, it is not necessarily needed to use a pure aliphatic monohydric alcohol containing no dialkyl carbonate, the use of which is requisite in the conventional reactive distillation techniques for achieving almost 100% conversion of a cyclic carbonate.

With respect to the continuous multi-stage distillation column to be used in step (1) of the method of the present invention, there is no particular limitation, as long as it is a distillation column which has two or more stages of distillation and which is capable of continuous distillation. In the present invention, the term "stages" means the number of theoretical stages (theoretical plates). In the case of a distillation column having no substantive stages, such as a packed column, the value obtained by dividing the packing height by the height per theoretical stage (plate) (H.E.T.P.) (height equivalent to a theoretical plate) is considered as the number of stages. Examples of such continuous multi-stage distillation columns include plate type columns using a tray, such as a bubble-cap tray, a sieve tray, a valve tray, a counter-flow tray, and packed type columns packed with various packings, such as a Raschig ring, a Lessing ring, a Pall ring, a Berl saddle, an Interlox saddle, a Dixon packing, a McMahon packing, a Heli pack, a Sulzer packing and Mellapak. Any column which is generally used as a continuous multi-stage distillation column can be utilized. Further, a mixed type of plate column and packed column comprising both a plate portion and a portion packed with packings, can also be preferably used. When a solid catalyst which is insoluble in the liquid phase in a distillation column is used, a packed column type distillation column, in which the solid catalyst is used in substitution for part or all of the packings, is preferably employed. As the continuous multi-stage distillation column to be used in step (1) of the method of the present invention, the above-mentioned distillation columns can be used individually or in combination. When used in combination, each of distillation columns may be connected to other distillation columns directly or in parallel.

In the present invention, when the reaction of step (1) is performed in reaction mode (b), at least one withdrawal port is provided in a side wall of the continuous multi-stage distillation column at a position or positions thereof corresponding to a stage or stages selected from the groups consisting of intermediate stages and a lowermost stage of the multi-stage distillation column, and a desired number of withdrawal port or ports can be provided. On the other hand, the introduction port for recycling the liquid withdrawn from the transesterification reactor through its outlet can be provided in the side wall of the multi-stage distillation column at a position above the or each withdrawal port. When a plurality of withdrawal ports are provided, the respective liquids withdrawn from the withdrawal ports can be combined and introduced to the transesterification reactor. Further, when a plurality of transesterification reactors are used, the respective liquid reaction mixtures withdrawn from the transesterification reactors can be combined and introduced to the continuous multi-stage distillation column through an introduction port thereof for recycling. These manners can be used individually or in combination. From the viewpoint of commercial scale practice of the method of the present invention, it is preferred that the number of transesterification reactors provided outside of the continuous multi-stage distillation column be two or more, and that a plurality of withdrawal ports are provided in the side wall of the multi-stage distillation column at respective positions corresponding to different stages. It is more preferred that the number of transesterification reactors provided outside of the continuous multi-stage distillation column be two or more, that a plurality of withdrawal ports are provided in the side wall of the multi-stage distillation column at respective positions corresponding to different stages, and that a plurality of introduction ports are provided in the side wall of the multi-stage distillation column at respective positions corresponding to respective different stages.

In the present invention, when the reaction of step (1) is performed in reaction mode (b), the transesterification reactor is provided at a position between the withdrawal port and the introduction port for recycling. There is no particular limitation with respect to the transesterification reactor to be used in reaction mode (b), as long as the reactor is a flow type reactor. Examples of transesterification reactors include a tubular reactor and a vessel type reactor.

A cyclic carbonate to be used as a feedstock in the present invention is represented by (A) in the above formula (I). Examples of cyclic carbonates include alkylene carbonates, such as ethylene carbonate and propylene carbonate, 1,3-dioxacyclohexa-2-one, 1,3-dioxacyclohepta-2-one, and the like. Of these cyclic carbonates, ethylene carbonate and propylene carbonate are preferably used because of their good availability. Ethylene carbonate is most preferably used.

An aliphatic monohydric alcohol used as another feedstock in the present invention is a compound which is represented by (B) in the above formula (I) and has a boiling point lower than that of the produced diol. The type of an aliphatic monohydric alcohol which can be used in the present invention varies depending on the type of the cyclic carbonate used. Examples of aliphatic monohydric alcohols include methanol, ethanol, propanol (isomers; n-propanol and iso-propanol), allyl alcohol, butanol (isomers; n-butanol, iso-butanol, sec-butanol and tert-butanol), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers) and the like. The above-mentioned aliphatic monohydric alcohol may be substituted with at least one substituent, such as a halogen atom, a lower alkoxy group, a cyano group, an alkoxycarbonyl group, an aryloxycarbonyl group, an acyloxy group, a nitro group or the like.

Of these aliphatic monohydric alcohols, an alcohol having 1 to 6 carbon atoms is preferably used. When ethylene carbonate is used as a cyclic carbonate, an alcohol having 1 to 4 carbon atoms, i.e., methanol, ethanol, propanol (isomers) or butanol (isomers) is preferably used. The method of the present invention can be employed advantageously especially when methanol and ethylene carbonate are used as feedstocks.

When the reaction of step (1) is performed in reaction mode (a), a transesterification catalyst is placed only in the continuous multi-stage distillation column and, when the reaction of step (1) is performed in reaction mode (b), a transesterification catalyst is placed in the transesterification reactor. When the reaction of step (1) is performed in combination of reaction modes (a) and (b), a transesterification catalyst is placed in each of the continuous multi-stage distillation column and the transesterification reactor.

The method for causing a catalyst to be present in the reaction zone is not particularly limited. For example, when the reaction of step (1) is performed in reaction mode (a), a homogeneous transesterification catalyst which is soluble in a reaction mixture under the reaction conditions can be caused to be present in the reaction zone by continuously feeding the homogeneous transesterification catalyst to the continuous multi-stage distillation column, or a heterogeneous transesterification catalyst (solid catalyst) which is insoluble in the reaction mixture under the reaction conditions, can be caused to be present in the reaction zone by packing the solid catalyst in the continuous multi-stage distillation column. The above-mentioned homogeneous and heterogeneous catalysts can be used in combination.

When a homogeneous catalyst is continuously fed to the continuous multi-stage distillation column, it may be fed to the distillation column together with a feedstock cyclic carbonate and/or a feedstock aliphatic monohydric alcohol. Alternatively, the homogeneous catalyst may be fed to the distillation column at a position different from that at which the feedstock is fed. Further, the homogeneous transesterification catalyst can be fed to the distillation column at any position as long as the position is at least one theoretical stage (plate) above the column bottom. However, since the region where the reaction actually takes place in the continuous multi-stage distillation column is generally below the position at which the homogeneous transesterification catalyst is fed, it is preferred that the homogeneous catalyst be fed to the distillation column at a position between the top of the column and the position at which the feedstock is fed.

When a heterogeneous solid catalyst is used as a transesterification catalyst, the catalyst can be packed in a desired amount at a desired position of the continuous multi-stage distillation column, as long as the catalyst layer is present at a position which is at least one theoretical stage (plate) above the column bottom. It is preferred that the catalyst layer is present at a position which is above the column bottom by two or more theoretical stages (plates). A catalyst which serves also as a packing for the continuous multi-stage distillation column can also be used.

When the reaction of step (1) is performed in reaction mode (b), for example, a homogeneous transesterification catalyst, which is soluble in the reaction mixture under the reaction conditions, can be caused to be present in the reaction zone by continuously feeding the homogeneous transesterification catalyst to the transesterification reactor and/or the continuous multi-stage distillation column, or a heterogeneous solid transesterification catalyst, which is insoluble in the reaction mixture under the reaction conditions employed, can be caused to be present in the reaction zone by packing the solid catalyst in the transesterification reactor or in both of the transesterification reactor and the continuous multi-stage distillation column. The above-mentioned homogeneous and heterogeneous catalysts can be used in combination. For example, a solid transesterification catalyst is packed in the transesterification reactor and/or the continuous multi-stage distillation column and a homogeneous transesterification catalyst is also fed to the transesterification reactor and/or the distillation column.

When a homogeneous catalyst is continuously fed to the transesterification reactor and/or the continuous multi-stage distillation column, it may be fed together with the feedstock cyclic carbonate and/or the feedstock aliphatic monohydric alcohol. Alternatively, the homogeneous catalyst may be fed to the transesterification reactor and/or the distillation column at a position thereof different from the position of the distillation column at which the feedstock is fed.

When a heterogeneous solid catalyst is used, a solid catalyst which also serves as a packing for the continuous multi-stage distillation column can be used.

As a transesterification catalyst used in the present invention, various types of known transesterification catalysts can be used. Examples of such catalysts include alkali metals or alkaline earth metals, such as lithium, sodium, potassium, rubidium, cesium, magnesium, calcium, strontium, barium and the like; basic compounds such as hydrides, hydroxides, alkoxides, aryloxides and amides of alkali metals or alkaline earth metals and the like; basic compounds, such as carbonates and hydrogencarbonates of alkali metals or alkaline earth metals, alkali metal or alkaline earth metal salts of organic acids and the like; tertiary amines such as triethylamine, tributylamine, trihexylamine, benzyldiethylamine and the like; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine, alkyltriazine and the like; cyclic amidines, such as diazabicycloundecene (DBU), diazabicyclononene (DBN) and the like; thallium compounds, such as thallium oxide, thallium halides, thallium hydroxide, thallium carbonate, thallium nitrate, thallium sulfate, thallium salts of organic acids and the like; tin compounds, such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, tin 2-ethylhexanoate and the like; zinc compounds, such as dimethoxyzinc, diethoxyzinc, ethylenedioxyzinc, dibutoxyzinc and the like; aluminum compounds, such as aluminum trimethoxide, aluminum triisopropoxide, aluminum tributoxide and the like; titanium compounds, such as tetramethoxytitanium, tetraethoxytitanium, tetrabutoxytitanium, dichlorodimethoxytitanium, tetraisopropoxytitanium, titanium acetate, titanium acetylacetonate and the like; phosphorus compounds, such as trimethylphosphine, triethylphosphine, tributylphosphine, triphenylphosphine, tributylmethylphosphonium halides, trioctylbutylphosphonium halides, triphenylmethylphosphonium halides and the like; zirconium compounds, such as zirconium halides, zirconocenes, zirconium acetylacetonate, zirconium alkoxides, zirconium acetate and the like; lead and lead-containing compounds, e.g., lead oxides, such as PbO, $PbO_2$, $Pb_3O_4$ and the like; lead sulfides, such as PbS, $Pb_2S_3$, $PbS_2$ and the like; lead hydroxides, such as $Pb(OH)_2$, $Pb_3O_2(OH)_2$, $Pb_2[PbO_2(OH)_2]$, $Pb_2O(OH)_2$ and the like; plumbites, such as $Na_2PbO_2$, $K_2PbO_2$, $NaHPbO_2$, $KHPbO_2$ and the like; plumbates, such as $Na_2PbO_3$, $Na_2H_2PbO_4$, $K_2PbO_3$, $K_2[Pb(OH)_6]$, $K_4PbO_4$, $Ca_2PbO_4$, $CaPbO_3$ and the like; lead carbonates and basic salts thereof, such as $PbCO_3$, $2PbCO_3 \cdot Pb(OH)_2$ and the like; alkoxylead compounds and aryloxylead compounds, such as $Pb(OCH_3)_2$, $(CH_3O)Pb(OPh)$, $Pb(OPh)_2$ and the like; lead salts of organic acids, and carbonates and basic salts thereof, such as $Pb(OCOCH_3)_2$, $Pb(OCOCH_3)_4$, $Pb(OCOCH_3)_2 \cdot PbO \cdot 3H_2O$, and the like; organolead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$, $Ph_2PbO$ and the like wherein Bu represents a butyl group and Ph represents a phenyl group; lead alloys, such as Pb—Na, Pb—Ca, Pb—Ba, Pb—Sn, Pb—Sb and the like; lead minerals, such as galena, zinc blende and the like; hydrates of these lead compounds; ion-exchangers, such as anion-exchange resins having tertiary amino groups, ion-exchange resins having amide groups, ion-exchange resins having at least one type of ion-exchange group selected from the group consisting of sulfonate, carboxylate and phosphate groups, strongly basic solid anion-exchangers having a quarternary ammonium groups as ion-exchange groups and the like; solid inorganic compounds, such as silica, silica-alumina, silica-magnesia, aluminosilicate, gallium silicate, various types of zeolites, various types of metal-exchanged zeolites, ammonium-exchanged zeolites; and the like.

Among the above-mentioned solid catalysts, strongly basic anion-exchangers having quaternary ammonium groups as anion-exchange groups are preferably used. Examples of such anion-exchangers include strongly basic anion-exchange resins having quaternary ammonium groups as anion-exchange groups, cellulose type strongly basic anion-exchangers having quaternary ammonium groups as anion-exchange groups, strongly basic anion-exchangers carried on an inorganic carrier which have quaternary ammonium groups as anion-exchange groups, and the like.

Of these strongly basic anion-exchange resins having quaternary ammonium groups as ion-exchange groups, styrene type strongly basic anion-exchange resins and the like are preferably used. A styrene type strongly basic anion-exchange resin is comprised of a styrene/divinylbenzene copolymer as a base resin, and quaternary ammonium groups (type I or type II) as anion-exchange groups, examples of which are diagrammatically represented by the following formulae (II).

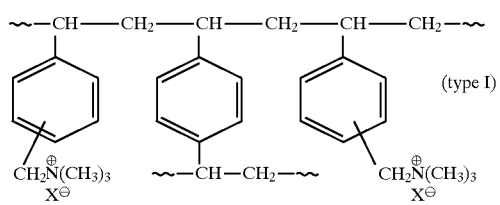

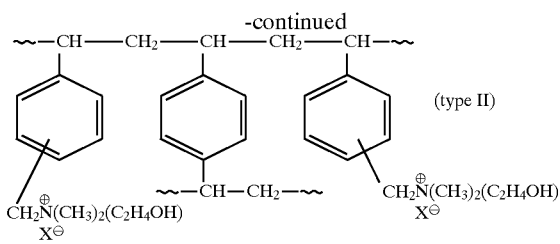

In above formula (II), X represents an anion. Generally, X is at least one type of an anion, selected from the group consisting of $F^-$, $Cl^-$, $Br^-$, $I^-$, $HCO_3^-$, $CO_3^{2-}$, $CH_3CO_2^-$, $HCO_2^-$, $IO_3^-$, $BrO_3^-$ and $ClO_3^-$. It is preferred that X be selected from the group consisting of $Cl^-$, $Br^-$, $HCO_3^-$ and $CO_3^{2-}$. With respect to the structure of the base resin of the anion-exchange resin, either a gel type or a macroreticular type (MR type) can be used. However, because of the high resistance to organic solvents, the MR type is preferred.

Examples of cellulose type strongly basic anion-exchangers having quaternary ammonium groups as ion-exchange groups include cellulose type strongly basic anion-exchangers having ion-exchange groups of the structure represented by the formula: —$OCH_2CH_2NR_3X$, which exchangers are obtained by trialkylaminoethylation of a part or all of the hydroxyl groups of cellulose. In the above formula, R represent an alkyl group, for example, a methyl group, an ethyl group, a propyl group, a butyl group or the like, preferably a methyl group or an ethyl group; and X is as defined above.

The inorganic carrier-carried strongly basic anion-exchanger usable in the present invention, which has quaternary ammonium groups as ion-exchange groups, is an anion-exchanger having quaternary ammonium groups represented by the formula —$O(CH_2)_nNR_3X$ wherein R and X are as defined above and n is usually an integer of from 1 to 6, preferably 2, which anion-exchanger can be prepared by the modification of a part or all of the hydroxyl groups on the surface of the inorganic carrier. Examples of inorganic carriers include silica, alumina, silica-alumina, titania, zeolite and the like. Of these, silica, alumina and silica-alumina are preferably used. Silica is most preferred. There is no limitation with respect to the method for the modification of hydroxyl groups on the surface of the inorganic carrier. For example, such a strongly basic anion-exchanger carried on an inorganic carrier can be obtained by subjecting an inorganic carrier and an aminoalcohol represented by the formula $HO(CH_2)_nNR_2$ to dehydration reaction between them in the presence of a basic catalyst to thereby effect aminoalkoxylation, followed by the reaction of the resultant aminoalkoxylated inorganic carrier with an alkyl halide represented by the formula RX', wherein X' represents a halogen atom, preferably Cl, Br or I, to thereby convert the aminoalkoxy group into a —$O(CH_2)_nNR_3X'$ group. The —$O(CH_2)_nNR_3X'$ group is further converted to a —$O(CH_2)_n NR_3X$ group having the desired anion X by an anion exchange reaction. When n is 2, an inorganic carrier is treated with N,N-dialkylaziridine so that the hydroxyl groups on the inorganic carrier are N,N-dialkylaminoethoxylated to obtain a —$OCH_2CH_2NR_2$ group, which is then converted to a —$OCH_2CH_2NR_3X$ group by the above-mentioned method.

Commercially available solid, strongly basic anion-exchangers having quaternary ammonium groups as ion-exchange groups can be used in the present invention. When a commercially available solid, strongly basic anion-exchanger is used, it can be treated for anion-exchange with a desired anion species before it is used as a transesterification catalyst.

A solid catalyst comprised of a macroreticular or gel type organic polymer or an inorganic carrier, each having bonded thereto a heterocyclic group containing at least one nitrogen atom, is preferably used as a transesterification catalyst. Further, the above-mentioned solid catalyst can be treated for quarternarizing a part or all of the nitrogen-containing heterocyclic groups before it is used.

The amount of the transesterification catalyst to be used in the present invention varies depending on the type thereof. The homogeneous catalyst, which is soluble in the reaction mixture under the reaction conditions, is fed continuously in an amount of from 0.0001 to 50% by weight, based on the total amount of the feedstock cyclic carbonate and the feedstock aliphatic monohydric alcohol. The solid catalyst is packed in an amount of from 10 to 95%, preferably from 50 to 90% by volume, based on the internal volume of the transesterification reactor. When the solid catalyst is packed in the continuous multi-stage distillation column, it is packed preferably in an amount of from 0.01 to 75% by volume, based on the internal volume of the empty distillation column.

In step (1) of the method of the present invention, a cyclic carbonate and an aliphatic monohydric alcohol containing a concomitant dialkyl carbonate in an amount of from 0 to 40% by weight, based on the total weight of the aliphatic monohydric alcohol and the concomitant dialkyl carbonate, are continuously fed to a continuous multi-stage distillation column. In reaction mode (a), there is no particular restriction with respect to the method for continuously feeding the feedstocks to the continuous multi-stage distillation column, and any feeding method can be used as long as the feedstocks can be contacted with the catalyst in a region of the distillation column which corresponds to at least one stage, preferably at least two stages. That is, the cyclic carbonate and the aliphatic monohydric alcohol can be continuously fed to at least one stage of the continuous multi-stage distillation column through a desired number of feeding pipes onto a desired stage as long as the above requirement is satisfied. The cyclic carbonate and the monohydric alcohol may be fed either to the same stage of the distillation column or to separate stages individually. The feedstocks are continuously fed in a liquid form, a gaseous form or a liquid-gas mixture form. In addition to the feeding of the feedstocks to the continuous multi-stage distillation column as described above, additional feedstocks can be fed in a gaseous form to the lower portion of the distillation column intermittently or continuously. Also preferred is a method wherein the cyclic carbonate is continuously fed in a liquid form or a liquid-gas mixture form to a stage at a level higher than the stage where the catalyst is present, while the aliphatic monohydric alcohol is continuously fed in a gaseous form to the lower portion of the distillation column. In this case, some of the aliphatic monohydric alcohol may be contained in the cyclic carbonate.

In reaction mode (b), the aliphatic monohydric alcohol and the cyclic carbonate may be fed directly to the continuous multi-stage distillation column. Alternatively, the aliphatic monohydric alcohol and the cyclic carbonate may be first introduced to a transesterification reactor to effect transesterification, and then the resultant transesterification reaction mixture may be fed to the continuous multi-stage distillation column.

The cyclic carbonate and the aliphatic monohydric alcohol may be fed, either individually or in mixture, through a desired number of feeding pipes to a desired stage of the distillation column, a desired portion of the transesterification reactor, or both a desired stage of the distillation column and a desired portion of the transesterification reactor. The feedstocks are continuously fed in a liquid form, a gaseous form, or a liquid-gas mixture form. In addition to the continuous feeding of the feedstocks to the continuous multi-stage distillation column and/or the transesterification reactor as described above, additional feedstocks can be fed in a gaseous form to the lower portion of the distillation column intermittently or continuously. Also a method may be employed wherein the cyclic carbonate is continuously fed in a liquid form or a liquid-gas mixture form to the uppermost transesterification reactor and/or to a stage of the continuous multistage distillation column positioned above the withdrawal port connected to the uppermost transesterification reactor, while continuously feeding the aliphatic monohydric alcohol in a liquid form, a gaseous form or a liquid-gas mixture form to the lowermost transesterification reactor. In this case, some of the aliphatic monohydric alcohol may be contained in the cyclic carbonate.

In the present invention, a small amount of a diol as a desired product may be contained in the feedstocks. The amount of a dialkyl carbonate in an aliphatic monohydric alcohol used in the present invention is in the range of from 0 to 40% by weight, preferably from 0.1 to 30% by weight, more preferably from 1 to 20% by weight, based on the total weight of the aliphatic monohydric alcohol and the dialkyl carbonate.

In step (1), the ratio of the aliphatic monohydric alcohol to the cyclic carbonate to be fed to the continuous multi-stage distillation column may vary depending on the type and quantity of the transesterification catalyst and the reaction conditions, but, in general, the molar ratio of the aliphatic monohydric alcohol to the cyclic carbonate may be in the range of from 0.01 to 1000. For increasing the conversion of the cyclic carbonate, it is preferred to feed the aliphatic monohydric alcohol in an excess amount which is 2 times or more by mole the mole of the cyclic carbonate. However, too high a concentration of the aliphatic monohydric alcohol is undesirable because the size of the reaction equipment has to be large. Therefore, it is especially preferred to use the aliphatic monohydric alcohol in an amount which is 2 to 10 times by mole the mole of the cyclic carbonate.

When carbon dioxide is present in a high concentration in the transesterification reaction system in step (1) of the method of the present invention, the reaction rate becomes low. Therefore, the $CO_2$ concentration of the reaction system is generally not higher than 500 ppm, preferably not higher than 200 ppm.

Also when water is present in a high concentration in the transesterification reaction system in step (1) of the method of the present invention, hydrolysis takes place simultaneously with the transesterification, resulting in a decrease in the selectivity for dialkyl carbonate in step (1). Therefore, the water concentration of the reaction system is generally not higher than 200 ppm, preferably not higher than 100 ppm.

In the present invention, when it is attempted to render the conversion of the cyclic carbonate in step (1) close to 100%, the reaction time has to be prolonged (and hence the size of the reaction equipment has to be increased), the aliphatic monohydric alcohol has to be used in large excess. On the other hand, when the conversion of the cyclic carbonate is too low, the size of the continuous hydrolysis reactor used in step (2) has to be large. Therefore, in step (1), the conversion of the cyclic carbonate is generally in the range of from 80 to 99%, preferably from 85 to 99%, more preferably from 90 to 98%.

The low boiling point mixture containing dialkyl carbonate produced in step (1) of the method of the present invention is continuously withdrawn from the upper portion of the continuous multi-stage distillation column in a gaseous form. The withdrawn gaseous mixture may be composed of a dialkyl carbonate alone or a mixture thereof with an aliphatic monohydric alcohol and a cyclic carbonate. Further, the withdrawn gaseous mixture may also contain a high boiling point product in a small amount.

A withdrawal port of the continuous multi-stage distillation column of step (1) for withdrawing the gaseous low boiling point mixture containing the dialkyl carbonate is preferably provided at a position between the position from which the feedstocks are fed and the top of the distillation column, or in the top of the distillation column. It is more preferred to provide the withdrawal port for the low boiling point mixture in the top of the distillation column. A part of the low boiling point mixture withdrawn from the withdrawal port may be returned to the upper portion of the distillation column to thereby effect the so-called reflux operation. When the reflux ratio is increased by conducting this reflux operation, the distillation efficiency of a low boiling product into a vapor phase is increased, thereby advantageously increasing the concentration of a low boiling point product in the withdrawn gaseous component. However, too much of an increase in the reflux ratio disadvantageously leads to an increase in the thermal energy required. Thus, the reflux ratio is generally chosen in the range of from 0 to 10, preferably from 0 to 5, more preferably from 0 to 3.

By continuously feeding the low boiling point mixture containing dialkyl carbonate withdrawn from the upper portion of the distillation column in step (1) to a dialkyl carbonate-separating apparatus and continuously recovering the dialkyl carbonate from the separating apparatus, the dialkyl carbonate can be obtained. Examples of such dialkyl carbonate-separating apparatuses include a distillation type separating apparatus, an extractive distillation type separating apparatus, a liquid-liquid extraction type separating apparatus, a crystallization type separating apparatus, an adsorption type separating apparatus and a membrane type separating apparatus. A combination of a plurality of different or identical separating apparatuses may be used. Among these separating apparatuses, a distillation type separating apparatus is especially preferred.

When the low boiling point mixture (containing the produced dialkyl carbonate and unreacted aliphatic monohydric alcohol) withdrawn from the upper portion of the multi-stage distillation column in step (1) is subjected to separation by means of a distillation type separating apparatus, the low boiling point mixture can be separated into various components, such as the produced dialkyl carbonate and unreacted aliphatic monohydric alcohol, in the form of one or more column top fractions containing a single component or a plurality of components and in the form of a column bottom liquid. As the above-mentioned column top fraction, an azeotropic mixture may be obtained depending on the types of feedstocks. After the components in the low boiling point mixture withdrawn from the upper portion of the multi-stage distillation column in step (1) are separated by means of a distillation type separating apparatus, one or more fractions containing the unreacted aliphatic monohydric alcohol and/or a column bottom liquid containing the unreacted aliphatic monohydric alcohol is then fed to the continuous multistage distillation column used in step (1).

As the distillation type separating apparatus, a single continuous multi-stage distillation column or a plurality of continuous multi-stage distillation columns can be used, wherein each continuous multi-stage distillation column may be of the same type as used in step (1). Explained hereinbelow is a mode of the method of the present invention in which an aliphatic monohydric alcohol and a dialkyl carbonate form a minimum boiling point azeotropic mixture, and wherein dimethyl carbonate is produced by using methanol as the aliphatic monohydric alcohol. A low boiling point mixture (containing methanol and dimethyl carbonate) withdrawn from the upper portion of the continuous multi-stage distillation column used in step (1) is continuously fed to a dimethyl carbonate-separating column. A low boiling point mixture containing a minimum boiling point azeotropic mixture of methanol and dimethyl carbonate is continuously withdrawn from an upper portion of the dimethyl carbonate-separating column, while continuously withdrawing dimethyl carbonate from a lower portion of the dimethyl carbonate-separating column, thereby obtaining dimethyl carbonate. As the dimethyl carbonate-separating column, a single continuous multi-stage distillation column or a plurality of continuous multi-stage distillation columns can be used, wherein each continuous multi-stage distillation column may be of the same type as used in step (1). The dimethyl carbonate-separating column is generally operated under reduced pressure or superatmospheric pressure in the range of from $0.5 \times 10^5$ to $50 \times 10^5$ Pa (0.51 to 51 kg/cm$^2$) in terms of the absolute pressure. The composition of methanol/dimethyl carbonate minimum boiling point azeotropic mixture may be varied depending on the operating pressure of the dimethyl carbonate-separating column. Therefore, the operating pressure of the dimethyl carbonate-separating column is chosen so that the dimethyl carbonate is obtained from the lower portion of the dimethyl carbonate-separating column. Specifically, an operating pressure higher than an operating pressure corresponding to the methanol/dimethyl carbonate ratio of the low boiling point mixture withdrawn from the upper portion of the column of step (1) is chosen for the dimethylcarbonate-separating column.

The low boiling point mixture (containing a minimum boiling point azeotropic mixture) withdrawn from the upper portion of the above-mentioned dimethyl carbonate-separating column may be fed to the continuous multi-stage distillation column used in step (1) as a feedstock usable in the present invention, i.e., methanol containing dimethyl carbonate.

A diol produced in step (1) of the method of the present invention is continuously withdrawn from a lower portion of the continuous multi-stage distillation column used in step (1) in a liquid form.

In the present invention, the upper potion of the continuous multi-stage distillation column means a portion between the top of the distillation column and a position at approximately half the height of the distillation column, and the upper portion includes the top of the column. The lower portion of the continuous multi-stage distillation column means a portion between the bottom of the distillation column and a position at approximately half the height of the distillation column, and the lower portion includes the bottom of the column.

Further, in the present invention, the liquid mixture withdrawn from the lower portion of the distillation column used in step (1) means a high boiling point mixture continuously withdrawn from the lower portion of the continuous multi-stage distillation column used in step (1), which high boiling point mixture contains a produced diol and an unreacted cyclic carbonate, and may also contain an aliphatic monohydric alcohol or both an aliphatic monohydric alcohol and a dialkyl carbonate.

When the cyclic carbonate/diol ratio of the liquid mixture withdrawn from the lower portion of the distillation column used in step (1) is too large, the size of the continuous hydrolysis reactor used in step (2) has to be disadvantageously large. However, for decreasing the cyclic carbonate/diol ratio of the liquid mixture withdrawn from the lower portion of the distillation column to an extremely low level, the conversion of cyclic carbonate has to close to 100%, which requires that the size of the reaction equipment and the amount of the aliphatic monohydric alcohol be increased. The cyclic carbonate/diol ratio of the liquid mixture withdrawn from the lower portion of the distillation column may be varied depending on the conversion of the cyclic carbonate and the amount of the diol in the feedstocks. However, the molar ratio of the cyclic carbonate to the diol contained in the liquid mixture withdrawn from the lower portion of the distillation column used in step (1) is generally in the range of from 0.01 to 0.25, preferably from 0.01 to 0.17, more preferably from 0.02 to 0.11.

The withdrawal port for withdrawing the liquid mixture from the continuous multi-stage distillation column used in step (1) is positioned at a lower portion of the distillation column, preferably at the bottom of the distillation column. A part of the withdrawn liquid mixture may be recycled to the lower portion of the continuous multi-stage distillation column in a gaseous form or a liquid-gas mixture form by heating by means of a reboiler.

The rate at which a liquid flows down inside the continuous multi-stage distillation column and the rate at which a vapor ascends inside the distillation column may be varied depending on the type of the distillation column, and on the type of the packing in the case of a packed column. However, the distillation column is generally operated so that no flooding or weeping occurs.

In step (1), when the reaction is performed in reaction mode (b), a part or all of a liquid flowing-down inside the multi-stage distillation column is continuously withdrawn through at least one withdrawal port provided in a side wall of the multi-stage distillation column at a position or positions thereof corresponding to a stage or stages selected from the group consisting of intermediate stages and a lowermost stage of the multi-stage distillation column, and the withdrawn liquid is continuously introduced to the transesterification reactor. The residence time in the transesterification reactor is generally in the range of from 0.001 to 100 hours, preferably from 0.003 to 50 hours, more preferably from 0.01 to 10 hours.

In step (1), when the reaction is performed in reaction mode (a), the reaction takes place within the continuous multi-stage distillation column. Further, when the reaction of step (1) is performed in reaction mode (b), the reaction can be advantageously conducted in both of the continuous multi-stage distillation column and the transesterification reactor. When the reaction takes place in the continuous multi-stage distillation column, the amount of dialkyl carbonate produced depends on the amount of hold-up liquid in the distillation column. That is, when the height and diameter of a distillation column are not changed, a greater hold-up capacity is preferred because the greater the hold-up capacity, the longer the residence time of the liquid phase, namely, the time during which the reaction is effected. However, when the amount of the hold-up liquid is too large, the residence time becomes too long, so that side reactions and flooding are likely to occur. Accordingly, in step (1) of the method of the present invention, the amount of the hold-up liquid of the continuous multi-stage distillation column varies depending on the distillation conditions and the type of the distillation column. Generally, however, the amount of the hold-up liquid is in the range of from 0.005 to 0.75 in terms of the volume ratio of the hold-up liquid to the empty continuous multi-stage distillation column.

In step (1) of the method of the present invention, the average residence time of the liquid phase in the continuous multi-stage distillation column depends on the reaction conditions, the type and inner structure (for example, the types of the plate and packing) of the continuous multi-stage distillation column, but is generally in the range of from 0.001 to 50 hours, preferably from 0.01 to 10 hours, more preferably from 0.05 to 5 hours.

When the reaction of step (1) is performed in reaction mode (a), the reaction temperature of the transesterification reaction means the temperature of the stage of the continuous multi-stage distillation column where the catalyst is present. When the reaction is performed in reaction mode (b), the reaction temperature means the temperature of the inside of the transesterification reactor and/or the temperature of the stage of the continuous multi-stage column where the catalyst is present. The reaction temperature varies depending on the types of the feedstocks, the reaction pressure, and whether the reaction takes place in the transesterification reactor or the continuous multi-stage distillation column, but is generally chosen in the range of from 0° to 350° C., preferably from 20° to 200° C. The reaction pressure can be selected from a reduced pressure, an atmospheric pressure and a superatmospheric pressure. The reaction pressure is generally in the range of from 1 Pa to $2 \times 10^6$ Pa (0.00001 to 20 kg/cm$^2$), preferably from $1 \times 10^3$ Pa to $1 \times 10^6$ Pa (0.01 to 10 kg/cm$^2$), more preferably from $1 \times 10^4$ Pa to $5 \times 10^5$ Pa (0.1 to 5 kg/cm$^2$), in terms of the absolute pressure.

In step (1), when the reaction is performed by reaction mode (b), that is, when the transesterification reaction is conducted in the transesterification reactor (b), there is an advantage such that, since the transesterification reactor is provided separately from the continuous multi-stage distillation column, reaction conditions (temperature and pressure) different from the distillation conditions can be employed in the transesterification reactor. Further, when two or more transesterification reactors are used, it is possible to employ different reaction conditions for different transesterification reactors, respectively.

In step (1), it is also possible to recycle a part of the high boiling point mixture withdrawn from the lower portion of the multi-stage distillation column to the multi-stage distillation column, so that a part of unreacted cyclic carbonate can be recycled to the multi-stage distillation column. When a part of the high boiling point mixture withdrawn from the lower portion of the multi-stage distillation column is recycled to the multi-stage distillation column, there is no particular limitation with respect to the position of an introduction port in the multi-stage distillation column, through which the part of the withdrawn high boiling point mixture is recycled to the multistage distillation column. However, it is preferred that this introduction port be positioned at an upper portion of the multi-stage distillation column.

With respect to step (2), the high boiling point mixture withdrawn from the lower portion of the multi-stage distillation column in step (1), as such, may be fed to a continuous hydrolysis reactor. Alternatively, using a separating apparatus, from the high boiling point mixture withdrawn from the lower portion of the multi-stage distillation column in step (1), a specific, single component can be separated or a plurality of components can be obtained individually or in mixture, and the component containing unreacted cyclic carbonate is then fed to a continuous hydrolysis reactor. As the separating apparatus for effecting the separation of the components in the high boiling point mixture withdrawn from the lower portion of the multi-stage distillation column in step (1), various separating apparatuses, such as a distillation type separating apparatus, an extractive distillation type separating apparatus, a liquid-liquid extraction type separating apparatus, a crystallization type separating apparatus, an adsorption type separating apparatus and a membrane type separating apparatus can be used. A combination of a plurality of different or identical separating apparatuses may be used. Among these separating apparatuses, a distillation type separating apparatus is especially preferred.

When the high boiling point mixture (containing the produced diol and unreacted cyclic carbonate) withdrawn from the lower portion of the multi-stage distillation column in step (1) is subjected to separation by means of a distillation type separating apparatus, the high boiling point mixture can be separated into various components, such as an unreacted cyclic carbonate and a diol, in the form of one or more column top fractions containing a single component or a plurality of components and in the form of a column bottom liquid. As the above-mentioned column top fraction, an azeotropic mixture may be obtained depending on the types of feedstocks compounds. After the components in the high boiling point mixture withdrawn from the lower portion of the multi-stage distillation column in step (1) are separated by means of a distillation type separating apparatus, one or more fractions containing the unreacted cyclic carbonate and a column bottom liquid are then fed to a continuous hydrolysis reactor. As the distillation type separating apparatus, a single continuous multi-stage distillation column or a plurality of continuous multi-stage distillation columns can be used, wherein each continuous multi-stage distillation column may be of the same type as used in step (1).

When a transesterification catalyst soluble in the liquid reaction system under reaction conditions is used, a fraction containing the transesterification catalyst and/or a column bottom liquid containing the transesterification catalyst is obtained. A part or all of the fraction containing the transesterification catalyst and/or the column bottom liquid containing the transesterification catalyst may be recycled to the continuous multi-stage distillation column used in step (1).

Specifically, as preferred examples of manners in which the high boiling point mixture withdrawn from the multi-stage distillation column in step (1) is first subjected to separation by means of a distillation type separating apparatus and then step (2) is conducted by using a continuous hydrolysis reactor, the following two modes of the method of the present invention can be mentioned.

1. A mode in which the high boiling point mixture withdrawn from a lower portion of the continuous multi-stage distillation in step (1) is continuously introduced, prior to the feeding thereof to the continuous hydrolysis reactor in step (2), to a low boiling point mixture-separating column which is comprised of a continuous multi-stage distillation column, and in which a low boiling point mixture containing the aliphatic monohydric alcohol and the dialkyl carbonate in a gaseous form is continuously withdrawn from an upper portion of the low boiling point mixture-separating column, while continuously withdrawing a high boiling point mixture containing the unreacted cyclic carbonate and the diol from a lower portion of the low boiling point mixture-separating column, wherein the low boiling point mixture withdrawn from the upper portion of the low boiling point mixture-separating column is continuously recycled to the multi-stage distillation column used in step (1), while continuously feeding the high boiling point mixture withdrawn from the low boiling point mixture-separating column to the continuous hydrolysis reactor used in step (2).

In continuously recycling the low boiling point mixture withdrawn from the upper portion of the low boiling point mixture-separating column to the continuous multi-stage distillation column used in step (1), the low boiling point mixture may be directly recycled to the multi-stage distillation column. Alternatively, before the recycling of the low boiling point mixture to the continuous multi-stage distillation column used in step (1), the low boiling point mixture may be first fed to the transesterification reactor to obtain a transesterification reaction mixture, which is then recycled to the continuous multi-stage distillation column used in step (1). As the low boiling point mixture-separating column, a continuous multi-stage distillation column can be used, and the continuous multi-stage distillation column may be of the same type as used in step (1).

2. A mode in which the cyclic carbonate is capable of forming a minimum boiling point azeotropic mixture with the diol, and in which the high boiling point mixture withdrawn from the lower portion of the low boiling point mixture-separating column is continuously introduced to an azeotropic mixture-separating column prior to the feeding of the high boiling point mixture to the continuous hydrolysis reactor, while continuously withdrawing the diol from a lower portion of the azeotropic mixture-separating column and continuously withdrawing a low boiling point mixture comprised of the minimum boiling point azeotropic mixture of the cyclic carbonate with the diol from an upper portion of the azeotropic mixture-separating column, and in which the low boiling point mixture withdrawn from the upper portion of the azeotropic mixture-separating column is introduced to the continuous hydrolysis reactor to effect a hydrolysis reaction and obtain a hydrolysis reaction mixture. As the azeotropic mixture-separating column, a continuous multi-stage distillation column can be used, and the continuous multi-stage distillation column may be of the same type as used in step (1).

In step (2) of the method of the present invention, water and the high boiling point mixture which has been withdrawn from the lower portion of the multi-stage distillation column in step (1) are continuously fed to a continuous hydrolysis reactor, to thereby effect a continuous hydrolysis of the unreacted cyclic carbonate and produce a diol and carbon dioxide, while continuously withdrawing the resultant hydrolysis reaction mixture containing the produced diol from the continuous hydrolysis reactor. When the high boiling point mixture withdrawn from the lower portion of the multi-stage distillation column in step (1) is first fed to a separating apparatus prior to the feeding thereof to the continuous hydrolysis reactor, a component obtained by the separation in the separating apparatus is fed to the continuous hydrolysis reactor.

With respect to the continuous hydrolysis reactor used in step (2), there is no particular limitation as long as it is a reaction apparatus which can be used for performing a continuous reaction between water and a cyclic carbonate. Examples of reactors usable as the continuous hydrolysis reactor include a tubular reactor; a vessel reactor; a column reactor, such as a distillation column reactor or a bubble column reactor; and a fluidized bed reactor. It is preferred to use a tubular reactor, a vessel reactor or a distillation column reactor.

When a distillation column reactor is used as the continuous hydrolysis reactor, the distillation column reactor may be a continuous multi-stage distillation column which is of the same type as used in step (1).

In step (2), a hydrolysis catalyst may be used. With respect to the hydrolysis catalyst used in step (2), there is no particular limitation as long as it is one which can be used for producing a diol by a reaction between a cyclic carbonate and water. Various conventional catalysts can be used. Examples of hydrolysis catalysts include mineral acids, such as nitric acid, hydrochloric acid and sulfuric acid; alkali metals and alkaline earth metals, such as lithium, sodium, potassium, rubidium, cesium, magnesium, calcium, strontium and barium; basic compounds, such as hydrides, alkoxides and aryloxides and amides of alkali metals and alkaline earth metals; alkali metal hydroxides, such as sodium hydroxide, potassium hydroxide, rubidium hydroxide and cesium hydroxide; alkaline earth metal hydroxides, such as magnesium hydroxide, calcium hydroxide and strontium hydroxide; alkali metal carbonates, such as sodium carbonate and potassium carbonate; alkali metal bicarbonates, such as sodium bicarbonate and potassium bicarbonate; organic acid salts of alkali metals and alkaline earth metals; inorganic acid salts, such as sodium molybdate, potassium molybdate, sodium tungstate and potassium tungstate; organic acid esters, such as carboxylic ester and sulfonic ester; a composite catalyst comprising a Lewis acid and a nitrogen-containing organic base; organoantimony compounds; a quaternary phosphonium salt; a quaternary ammonium salt; tertiary amines, such as triethyl amine, tributyl amine, trihexyl amine and benzyl diethyl amine; and solid catalysts, such as synthetic zeolite, hydrotalcite, an organic ion exchange resin, activated alumina, silica-alumina, alumina carrying a copper compound, silica-alumina carrying a copper compound, alumina carrying a zinc compound and silica-alumina carrying a zinc compound.

When the transesterification catalyst used in step (1) is soluble in the liquid reaction system under reaction conditions and also can serve as a hydrolysis catalyst, there are advantages:

that, when the high boiling point mixture which has been withdrawn from the lower portion of the multistage distillation column in step (1) is directly fed to the continuous hydrolysis reactor without being subjected to separation in a separating apparatus, the transesterification catalyst used in step (1), as such, can be used as a hydrolysis catalyst in step (2); and that, when the high boiling point mixture which has been withdrawn from the lower portion of the multistage distillation column in step (1) is first subjected to separation in a distillation column type separating apparatus prior to the feeding thereof to the continuous hydrolysis reactor, a part or all of a fraction containing the transesterification catalyst used in step (1) and/or a part or all of a column bottom liquid containing the transesterification catalyst used in step (1) (which fraction and/or column bottom liquid is obtained by the separation), as such, can be used as a hydrolysis catalyst in step (2).

The amount of the hydrolysis catalyst used in the present invention may be varied depending on the type of the hydrolysis catalyst. However, when the hydrolysis catalyst is continuously fed to the continuous hydrolysis reactor, the amount of the hydrolysis catalyst is generally 0.0001 to 50% by weight, based on the weight of the cyclic carbonate fed to the continuous hydrolysis reactor.

When the solid catalyst is used in a manner such that the solid catalyst is disposed in the continuous hydrolysis reactor, it is preferred that the amount of the solid catalyst be from 10 to 75% by volume, based on the internal volume of the continuous hydrolysis reactor.

With respect to the water used in step (2), there is no particular limitation, and any type of water can be used. Generally, deionized water, condensed water from steam, or the like is used.

The amount of water to be used can be reduced to a stoichiometrical amount. Depending on the reaction mode, the amount of water to be used can even be reduced to an amount smaller than a stoichiometrical amount. However, in general, from a practical viewpoint, water is used in an amount 1 to 100 times by mole the stoichiometrical amount. It is preferred that water be used in an amount 1.01 to 50 times by mole, more preferably 1.01 to 10 times by mole the stoichiometrical amount.

The reaction conditions for the hydrolysis reaction in the continuous hydrolysis reactor may be varied depending on the presence or absence of a hydrolysis catalyst. When a hydrolysis catalyst is used, the hydrolysis reaction conditions may be varied depending on the type and amount of the hydrolysis catalyst. However, in general, the reaction temperature is from 50° to 300° C., preferably from 80° to 250° C., more preferably from 100° to 200° C. The reaction time may be varied depending on the presence or absence of a hydrolysis catalyst. When a hydrolysis catalyst is used, the reaction time may be varied depending on the type and amount of the hydrolysis catalyst and the reaction temperature. However, in general, the reaction time is from 0.001 to 50 hours, preferably from 0.01 to 10 hours, more preferably from 0.02 to 5 hours, in terms of the average residence time. The reaction pressure may be varied depending on the reaction temperature. However, in general, the reaction pressure is from $1\times10^3$ to $2\times10^7$ Pa (0.01 to 200 kg/cm$^2$), preferably from $1\times10^4$ to $1\times10^7$ Pa (0.1 to 100 kg/cm$^2$), in terms of the absolute pressure.

In step (2), the resultant hydrolysis reaction mixture containing the produced diol is continuously withdrawn from the continuous hydrolysis reactor. By subjecting the hydrolysis reaction mixture to distillation, a high purity diol fraction and a fraction containing by-produced carbon dioxide can be separated from the hydrolysis reaction mixture. Further, when the hydrolysis reaction mixture contains an unreacted cyclic carbonate, an unreacted aliphatic monohydric alcohol and the produced dialkyl carbonate, the hydrolysis reaction mixture may be subjected to distillation to separate these components from the hydrolysis reaction mixture, and these separated components are then recycled to the continuous multi-stage distillation column used in step (1). These components may be directly recycled to the continuous multi-stage distillation column used in step (1). Alternatively, these components may be first fed to the transesterification reactor and the resultant transesterification reaction mixture may be recycled to the continuous multi-stage distillation column used in step (1).

Further, when the hydrolysis reaction mixture obtained in step (2), containing the produced diol, also contains unreacted water, the hydrolysis reaction mixture may be subjected to distillation to separate the water as a fraction, and the obtained water fraction may be recycled to the continuous hydrolysis reactor used in step (2).

In the above-mentioned reaction mode in which the cyclic carbonate is capable of forming a minimum boiling point azeotropic mixture with the diol, and in which use is made of an azeotropic mixture-separating column, and in which the low boiling point mixture (containing the minimum boiling point azeotropic mixture of the cyclic carbonate with the diol) continuously withdrawn from an upper portion of the azeotropic mixture-separating column is introduced to the continuous hydrolysis reactor to effect a hydrolysis reaction and obtain a hydrolysis reaction mixture, the obtained hydrolysis reaction mixture may be recycled to the azeotropic mixture-separating column.

When the continuous hydrolysis reactor used in step (2) is one selected from the group consisting of a tubular reactor and a vessel reactor, the produced hydrolysis reaction mixture containing the diol and the carbon dioxide may be continuously introduced to a diol-separating column which is comprised of a continuous multi-stage distillation column, and the diol may be continuously withdrawn from a lower portion of the diol-separating column, while continuously withdrawing a low boiling point mixture containing the carbon dioxide from an upper portion of the diol-separating column. With respect to the feeding of water to the continuous hydrolysis reactor used in step (2), from the viewpoint of reducing the water content of a diol to be obtained, it is preferred that the water be fed to the continuous hydrolysis reactor at a position above a withdrawal port provided in a side wall of the continuous hydrolysis reactor for withdrawing the diol. Further, with respect to the feeding of the high boiling point mixture withdrawn from a lower portion of the low boiling point mixture-separating column to the continuous hydrolysis reactor used in step (2), from the viewpoint of reducing the cyclic carbonate content of a diol to be obtained, it is preferred that the high boiling point mixture be fed to the continuous hydrolysis reactor at a position above a withdrawal port provided in a side wall of the continuous hydrolysis reactor for withdrawing the diol.

As the diol-separating column, a continuous multi-stage distillation column can be used, and the continuous multi-stage distillation column may be of the same type as used in step (1).

When the continuous hydrolysis reactor used in step (2) is a hydrolysis column comprised of a continuous multi-stage distillation column, a high boiling point mixture containing the diol may be withdrawn from a lower portion of the continuous hydrolysis column, while continuously withdrawing a low boiling point mixture containing the carbon dioxide from an upper portion of the continuous hydrolysis column. Further, when the high boiling point mixture withdrawn from a lower portion of the continuous multi-stage distillation column in step (1) contains the aliphatic monohydric alcohol and the dialkyl carbonate, wherein the continuous hydrolysis reactor is a continuous hydrolysis column comprised of a continuous multi-stage distillation column, a low boiling point mixture containing the aliphatic monohydric alcohol, the dialkyl carbonate, the carbon dioxide and optionally water may be continuously withdrawn from an upper portion of the continuous hydrolysis column and recycled to the continuous multi-stage distillation column used in step (1), while continuously withdrawing the diol from a lower portion of the continuous hydrolysis column. When carbon dioxide enters the reaction system in step (1), the transesterification reaction in step (1) is adversely affected and hence the reaction rate becomes low. Further, when water enters the reaction system in step (1), hydrolysis proceeds in step (1) and hence the selectivity for a dialkyl carbonate in step (1) becomes low. Therefore, with respect to the above-mentioned recycling of the low boiling point mixture withdrawn from the upper portion of the continuous hydrolysis column to the continuous multi-stage distillation column used in step (1), from the viewpoint of achieving a high reaction rate and a high selectivity for a dialkyl carbonate, it is preferred that the carbon dioxide or both the carbon dioxide and the water be removed from the low boiling point mixture withdrawn from the upper portion of the continuous hydrolysis column prior to the recycling of the low boiling point mixture to the continuous multi-stage distillation column used in step (1). With respect to the feeding of water to the continuous hydrolysis reactor used in step (2), it is preferred that the water be fed to the continuous hydrolysis reactor at a position above a withdrawal port provided in a side wall of the continuous hydrolysis reactor for withdrawing the diol. With respect to the feeding position at which the high boiling point mixture (containing unreacted cyclic carbonate) withdrawn from the lower portion of the continuous multi-stage distillation column used in step (1) is fed to the continuous hydrolysis reactor, there is no particular limitation. However, from the viewpoint of reducing the cyclic carbonate content of a diol to be obtained, it is preferred that the high boiling point mixture withdrawn from the lower portion of the continuous multi-stage distillation column used in step (1) be fed to the continuous hydrolysis reactor at a position above a withdrawal port provided in a side wall of the continuous hydrolysis reactor for withdrawing the diol.

In the present invention, it is not necessary to use a solvent. However, for the purposes of, e.g., (1) facilitating the reaction operation and (2) separating a dialkyl carbonate and a diol efficiently by performing azeotropic distillation or extractive distillation, an appropriate inert solvent may be used as a reaction solvent, an azeotrope-forming agent or an extracting agent. Examples of inert solvents include an ether, an aliphatic hydrocarbon, an aromatic hydrocarbon, a halogenated aliphatic hydrocarbon and a halogenated aromatic hydrocarbon.

An inert gas, such as nitrogen, helium, argon or the like, may be present in the reaction system. Further, for the purpose of promoting the distilling-off of a generated low boiling point reaction product, the above-mentioned inert gas or a gaseous form of an inert low boiling point organic compound may be introduced to the reaction system from a lower portion of a continuous multi-stage distillation column.

BEST MODE FOR CARRYING OUT THE INVENTION

The present invention will be described in greater detail with reference to the following Examples and Comparative Examples, which should not be construed as limiting the scope of the present invention.

In the following Examples and Comparative Examples, the yield (%) of ethylene glycol is determined, based on the amount of the charged ethylene carbonate; the selectivity (%) for ethylene glycol is determined, based on the amount of the consumed ethylene carbonate; the yield (%) of dimethyl carbonate is determined, based on the amount of the charged ethylene carbonate; and the selectivity (%) for dimethyl carbonate is determined, based on the amount of the consumed methanol.

EXAMPLE 1

Using a system as shown in FIG. 1, dimethyl carbonate (DMC) and ethylene glycol (EG) were continuously produced from ethylene carbonate (EC) and methanol (MeOH).

As a catalyst concurrently serving as a packing, an anion-exchange resin having a quaternary ammonium group as an ion-exchange group [which anion-exchange resin had been obtained by subjecting a Cl$^-$ type of Dowex (registered trademark) MSA-1 resin (manufactured and sold by Dow Chemical Co., U.S.A.) to ion-exchange with a 2N aqueous solution of $Na_2CO_3$ so that about 50% of the Cl$^-$ ions were converted to $CO_3{}^{2-}$ ions, and the resultant resin was washed repeatedly with purified water and then with dried methanol to effect dehydration and drying of the resin] was packed in continuous multi-stage distillation column 1 in a height of 60 cm, which distillation column was comprised of a column having an inner diameter of 2 cm and a packing height of 100 cm, and wherein stainless-steel Dixon packings (3 mm φ) were packed in distillation column 1 so that the above-mentioned anion-exchange resin was interposed between the Dixon packings each having a height of about 10 cm.

A mixture of EC and MeOH (weight ratio of EC/MeOH= 5/1) was continuously fed in a liquid form to upper portion 4 (above the uppermost stage) of continuous multi-stage distillation column 1 through conduit 2 and preheater 3 at a flow rate of 52.5 g/h while MeOH was also continuously fed in a gaseous form to lower portion 8 (below the lowermost stage) of continuous multi-stage distillation column 1 through conduit 5 and evaporator 6' at a flow rate of 162 g/h (the temperature of the gaseous MeOH was 90° C.), to thereby effect a transesterification reaction. Continuous multi-stage distillation column 1 was operated under atmospheric pressure, and the temperature of upper portion 4 of the distillation column was 76° C. A gaseous mixture distilled from the top of distillation column 1 was condensed by means of condenser 7, and the resultant condensate (containing MeOH and DMC in concentrations of 75.7% by weight and 24.3% by weight, respectively) was recovered from the system at a flow rate of 166.5 g/h. A reaction mixture (containing MeOH, DMC, EG and EC in concentrations of 31.3% by weight, 2.7% by weight, 59.8% by weight and 6.2% by weight, respectively) was withdrawn from the bottom of distillation column 1 at a flow rate of 48 g/h and fed to continuous hydrolysis reactor 37 having an inner diameter of 7.5 mm and a length of 30 cm through conduit 9 [which continuous hydrolysis reactor had been packed with activated alumina beads, and the temperature and internal pressure of which was maintained at 170° C. and $2.5 \times 10^6$ Pa (25 kg/cm$^2$-G), respectively], together with water which was introduced via conduit 35 at a flow rate of 1.5 g/h, to thereby effect a continuous hydrolysis of EC in the reaction mixture. The resultant hydrolysis reaction mixture was recovered through conduit 38 at a flow rate of 49.5 g/h. As a result of the analysis, it was found that the hydrolysis reaction mixture contained MeOH, DMC and EG in concentrations of 30.3% by weight, 2.6% by weight and 62.2% by weight, respectively. It was also found that the hydrolysis reaction mixture contained no ethylene carbonate (EC) and also no diethylene glycol (DEG).

From the above data, it can be seen that the conversion of EC was 100%, the yield of DMC was 93% (DMC was produced at a production rate of 41.7 g/h), the selectivity for DMC was not lower than 99%, the yield of EG was not lower than 99%, and the selectivity for EG was not lower than 99%. As apparent from the above, EC did not remain in the hydrolysis reaction mixture. Also, the volume (V) of the reaction zone in continuous multi-stage distillation column 1 was calculated as follows: $V = \pi \times 1^2 \times 60/1{,}000 = 0.188$ liter. Therefore, the productivity of DMC in terms of the space time yield was: $41.7/0.188 = 221.8$ g/liter.h.

If desired, as a transesterification catalyst, a homogeneous catalyst can be used instead of or in addition to the solid catalyst. In such a case, the homogeneous catalyst is supplied to distillation column 1 through conduit 2' shown in FIG. 1.

EXAMPLE 2

Figure 2:
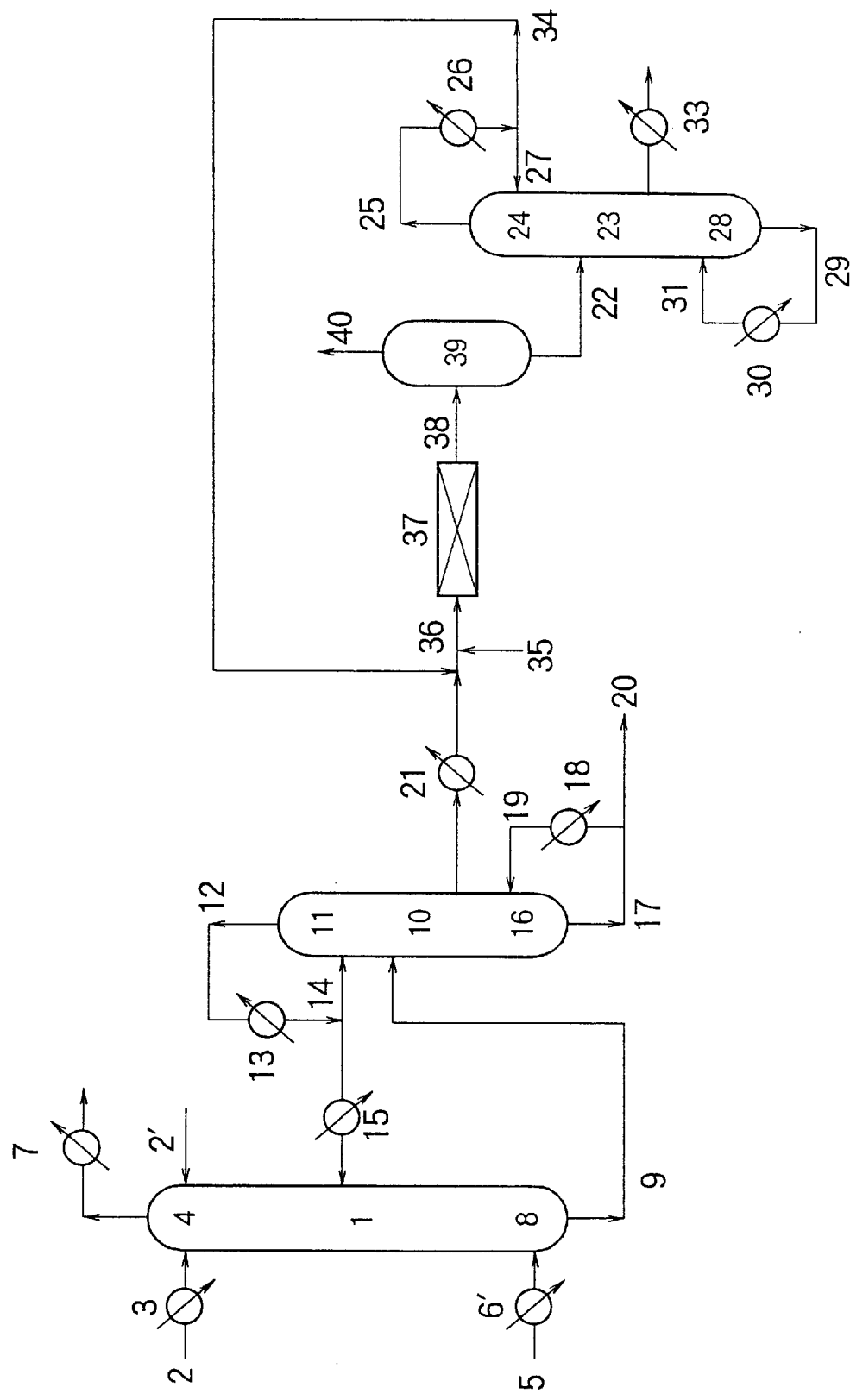
FIG. 2 is a diagram showing the system which was used for practicing Example 2 of the present application.

Using a system as shown in FIG. 2, dimethyl carbonate (DMC) and ethylene glycol (EG) were continuously produced from ethylene carbonate (EC) and methanol (MeOH).

Stainless-steel Dixon packings (3 mm φ) were packed in continuous multi-stage distillation column 1, which was comprised of a column having an inner diameter of 2 cm and a packing height of 200 cm. EC was continuously fed in a liquid form to upper portion 4 (above the uppermost stage) of distillation column 1 through conduit 2 and preheater 3 at a flow rate of 120 g/h, and a 3% by weight solution of sodium hydroxide (as a catalyst) in ethylene glycol was also continuously fed in a liquid form to upper portion 4 of distillation column 1 through conduit 2' at a flow rate of 9 g/h, while continuously feeding a mixture of MeOH and DMC (MeOH/DMC weight ratio=95/5) in a gaseous form to lower portion 8 (below the lowermost portion) of distillation column 1 through conduit 5 and evaporator 6' at a flow rate of 330 g/h (the temperature of the gaseous MeOH/DMC mixture was 94° C.), to thereby effect a transesterification reaction. Continuous multi-stage distillation column 1 was operated under atmospheric pressure, and the temperature of upper portion 4 of the distillation column was 77° C.

A gaseous mixture distilled from the top of distillation column 1 was condensed by condenser 7, and the resultant condensate (containing MeOH and DMC in concentrations of 63.7% by weight and 36.3% by weight, respectively) was recovered from the system at a flow rate of 363 g/h. A liquid reaction mixture [containing a low boiling point mixture (comprised of MeOH and DMC), EG and EC, in concentrations of 29% by weight, 65.5% by weight, and 5.3% by weight, respectively] was withdrawn from the bottom of the distillation column at a flow rate of 135 g/h and fed to low boiling point mixture-separating column 10 at a position 40 cm below the top of column 10 through conduit 9, which column 10 was comprised of a column having an inner diameter of 2.5 cm and a packing height of 120 cm, and had been packed with stainless-steel Dixon packings (3 mm φ).

Low boiling point mixture-separating column 10 was operated under conditions such that the pressure of upper portion 11 (above the uppermost stage) thereof was 1.3×10³ Pa (10 torr) and the temperature of lower portion 16 (below the lowermost stage) thereof was 102° C. A gaseous mixture (containing EG and EC each in a concentration lower than 0.1% by weight) withdrawn from the top of column 10 was condensed by condenser 13. A part of the resultant condensate was refluxed to upper portion 11 of column 10 through conduit 14 (reflux ratio: 2) while returning, through evaporator 15, the remainder of the condensate in a gaseous form to continuous multi-stage distillation column 1 at a position 120 cm below the top of distillation column 1 at a flow rate of 39 g/h. On the other hand, a part of a liquid (containing EG and NaOH in concentrations of 97% by weight and 3% by weight, respectively) withdrawn from the bottom of column 10 was recovered from the system through conduit 20 at a flow rate of 9 g/h, while the remainder of the withdrawn liquid was heated by reboiler 18 and returned to column 10 through conduit 19. A gaseous fraction containing EG and EC was withdrawn from column 10 through a withdrawal port provided in a side wall of column 10 at a position 90 cm below the top of column 10 at a flow rate of 87 g/h, and condensed by condenser 21 to obtain a condensate (containing EG and EC in concentrations of 91.7% by weight and 8.3% by weight, respectively).

The condensate obtained in condenser 21 was introduced to continuous hydrolysis reactor 37 [which was of the same type as used in Example 1, and the internal temperature and pressure of which was maintained at 180° C. and 2.5×10⁶ Pa (25 kg/cm²-G), respectively], together with a liquid withdrawn from the top of diol (EG)-separating column 23 (described below) through conduit 34, and water fed from conduit 35 at a flow rate of 1.5 g/h, to thereby effect a continuous hydrolysis reaction of EC in the condensate. The weight ratio of water to EC at the inlet of continuous hydrolysis reactor 37 was 0.5. The hydrolysis reaction mixture withdrawn from the hydrolysis reactor was introduced to gas-liquid separator 39 through conduit 38, from which carbon dioxide was discharged through conduit 40 and a mixture of EG and water was withdrawn through conduit 22. The withdrawn EG/water mixture was fed to diol-separating column 23, which had been packed with Dixon packings (3 mm φ) and was comprised of a column having a diameter of 2.5 cm and a packing height of 120 cm, at a position 40 cm below the top of column 23.

Diol-separating column 23 was operated under conditions such that the pressure of upper portion 24 (above the uppermost portion) thereof was 2.7×10³ Pa (20 torr), and the temperature of lower portion 28 (below the lowermost portion) thereof was 111° C. A gaseous mixture was withdrawn from the top of column 23 through conduit 25 and condensed by condenser 26 to obtain a condensate, and a part of the obtained condensate was refluxed to column 23 through conduit 27 (reflux ratio: 2), while the remainder of the condensate was returned to continuous hydrolysis reactor 37 through conduit 34 at a flow rate of 2.1 g/h. The liquid withdrawn from the bottom of column 23 was heated by reboiler 30 and returned to column 23. Also, a gaseous mixture was withdrawn from the withdrawal port provided in the side wall of column 23 at a position 90 cm below the top of column 23 at a flow rate of 85 g/h, and condensed by condenser 33, to thereby obtain EG [EG content: not lower than 99.999% by weight; and the total content of EC and diethylene glycol (DEG): not higher than 0.1 ppb by weight].

From the above data, it can be seen that the conversion of EC was 100%, the yield of DMC was 94% (DMC was produced at a production rate of 115.3 g/h), the selectivity for DMC was not lower than 99%, the yield of EG having high purity was not lower than 99% (EG was produced at a production rate of 85 g/h), and the selectivity for EG was not lower than 99%. As apparent from the above, EC did not remain in the hydrolysis reaction mixture. Also, the volume (V) of the reaction zone in continuous multi-stage distillation column 1 was calculated as follows: V=π×1²× 200/1,000=0.628 liter. Therefore, the productivity of DMC in terms of the space time yield was: 115.3/0.628=183.6 g/liter.h.

Comparative Example 1

(Run 1)

Substantially the same procedure as in Example 2 was repeated using substantially the same system as shown in FIG. 2, except that the operation was conducted so as to end at condenser 21, and continuous hydrolysis reactor 37 and the lines and columns following reactor 37 were omitted, and that low boiling point mixture-separating column 10 was operated in a manner such that a gaseous mixture withdrawn from the top of column 10, containing not only the low boiling point mixture but also EC and EG was recycled to distillation column 1 through condenser 13 and evaporator 15, wherein the amount of EC contained in the gaseous mixture withdrawn for a predetermined period of time was substantially equivalent to the amount of unreacted EC in distillation column 1. The flow rate of the gaseous mixture (containing EG and EC in concentrations of 48.9% by weight and 8.0% by weight, respectively, and the balance of MeOH and DMC), which was recycled from low boiling point mixture-separating column 10 to distillation column 1, was 90.4 g/h.

A gaseous mixture (containing MeOH and DMC in concentrations of 74.4% by weight and 25.6% by weight, respectively) was withdrawn from the top of distillation column 1 and fed to condenser 7 to obtain a condensate, and the obtained condensate was recovered at a flow rate of 350.6 g/h. A liquid mixture (containing EC and EG in concentrations of 27.9% by weight and 52.3% by weight, respectively) was withdrawn from the bottom of distillation column 1 and fed to low boiling point mixture-separating column 10 at a flow rate of 198 g/h. A liquid mixture (containing NaOH and EC in concentrations of 3% by weight and 72.4% by weight, respectively, and the balance of high boiling point diols, such as diethlene glycol) was recovered from the bottom of column 10 through conduit 20 at a flow rate of 9 g/h. From the withdrawal port provided in a side wall of column 10, 98.9 g of a mixture (containing EG and EC in concentrations of 59.7% by weight and 40.3% by weight, respectively) was recovered through condenser 21.

From the above data, it can be seen that the conversion of EC was 60%, the yield of DMC was 59.6% (DMC was produced at a production rate of 73.1 g/h), the selectivity for DMC was 99%, the yield of EG was 58.3% (EG was produced at a production rate of 49.3 g/h), and the selectivity for EG was 97% [these values were calculated on the assumption that the mixture withdrawn from the withdrawn port of column 10 contained EG derived from the catalyst solution (i.e., a solution of NaOH in EG) fed through conduit 2'].

(Run 2)

Substantially the same procedure as in Run 1 above was repeated, except that the flow rate of EC fed to distillation column 1 through conduit 2 was reduced to 70 g/h. The flow rate of a gaseous mixture (containing EG and EC in concentrations of 36.3% by weight and 5.9% by weight, respectively, and the balance of MeOH and DMC), which was recycled from low boiling point mixture-separating column 10 to distillation column 1, was 71.4 g/h. A gaseous mixture (containing MeOH and DMC in concentrations of 75.6% by weight and 24.4% by weight, respectively) was withdrawn from the top of distillation column 1 and fed to condenser 7 to obtain a condensate, and the obtained condensate was recovered at a flow rate of 349.3 g/h. A reaction mixture (containing EC and EG in concentrations of 4.9% by weight and 63.2% by weight, respectively) was withdrawn from the bottom of distillation column 1 and fed to low boiling point mixture-separating column 10 at a flow rate of 129.5 g/h. A liquid mixture (containing NaOH and EG in concentrations of 3.0% by weight and 97% by weight, respectively) was recovered at a flow rate of 9 g/h from the bottom of low boiling point mixture-separating column 10 through conduit 20. From the withdrawal port provided in a side wall of low boiling point mixture-separating column 10, 49.5 g of a mixture (containing EG and EC in concentrations of 95.8% by weight and 4.2% by weight, respectively) was recovered through condenser 21.

From the above data, it can be seen that the conversion of EC was 97%, the yield of DMC was 96% (DMC was produced at a production rate of 68.7 g/h), the selectivity for DMC was 99%, the yield of EG was 96% (EG was produced at a production rate of 47.4 g/h), and the selectivity for EG was 99%. Also, the productivity of DMC in terms of the space time yield was: 68.7/0.628=109.4 g/liter.h.

As is apparent from the above, when the conversion of EC is increased by recycling unreacted EC to distillation column 1, a large amount of an aliphatic alcohol (methanol) is required. Further, it can be seen that the productivity of EC can be increased when the hydrolysis reaction of unreacted EC is conducted as in Example 2, instead of increasing the conversion of EC as in the instant Comparative Example 1 [for example, (productivity of DMC in Example 2)÷ (productivity of DMC in Run 2 of Comparative Example 1)=183.6 g/liter.h÷109.4 g/liter.h)=1.7 (times)]. In Example 2, EG having high purity is obtained in a substantially theoretical quantity according to the chemical reaction formula.

Comparative Example 2

Figure 3:
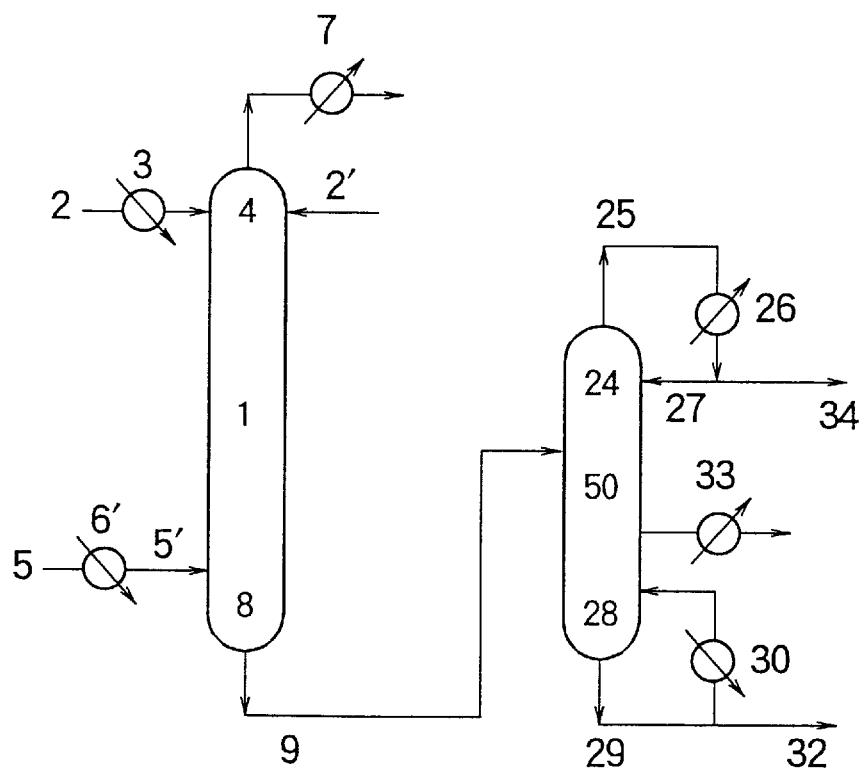
FIG. 3 is a diagram showing the system which was used for practicing Comparative Example 2 of the present application.

Raschig Rings (6 mm φ) were packed in continuous multi-stage distillation column 1 as shown in FIG. 3, which was comprised of a column having an inner diameter of 2.5 cm and a packing height of 250 cm, wherein the interior of the column was isothermally maintained at a temperature of 80° C. EC was continuously fed in a liquid form to distillation column 1 at a position 10 cm below the top of the distillation column through conduit 2 and preheater 3 at a flow rate of 120 g/h, and the same catalyst solution as used in Example 2 was continuously fed in a liquid form to upper portion 4 (above the uppermost stage) of distillation column 1 through conduit 2' at a flow rate of 9 g/h, while continuously feeding the same gaseous mixture of MeOH and DMC as used in Example 2 to distillation column 1 at a position 30 cm above the bottom of the distillation column through evaporator 6' and conduit 5' at a flow rate of 330 g/h, to thereby effect a transesterification reaction. Continuous multi-stage distillation column 1 was operated under atmospheric pressure, and the temperature of upper portion 4 of the distillation column was 78° C.

A gaseous mixture distilled from the top of distillation column 1 was condensed by condenser 7, and the resultant condensate (containing MeOH and DMC in concentrations of 63.3% by weight and 36.7% by weight, respectively) was recovered from the system at a flow rate of 306 g/h. A reaction mixture (containing MeOH, DMC, EG and EC in concentrations of 27.8% by weight, 5.1% by weight, 53.9% by weight and 13.0% by weight, respectively) was withdrawn from the bottom of the distillation column at a flow rate of 148 g/h and fed to distillation column 50 at a position 40 cm below the top of column 50 through conduit 9, which column 50 was comprised of a column having an inner diameter of 2.5 cm and a packing height of 120 cm, and had been packed with stainless-steel Dixon packings (3 mm φ).

Distillation column 50 was operated under conditions such that the pressure of upper portion 24 (above the uppermost stage) was $1.3 \times 10^3$ Pa (10 torr), and the temperature of lower portion 28 (below the lowermost stage) was 138° C. A gaseous mixture of MeOH and DMC distilled from the top of distillation column 50 was condensed by condenser 26, and a part of the resultant condensate was refluxed to upper portion 24 of column 50 through conduit 27, while the remainder of the condensate was recovered from the system at a flow rate of 49 g/h. The recovered condensate was analyzed and, as a result, it was found that the resultant condensate contained MeOH and DMC in concentrations of 84.6% by weight and 15.4% by weight, respectively. A liquid was withdrawn from the bottom of column 50, and a part of the withdrawn liquid was recovered from the system through conduit 32 at a flow rate of 24.5 g/h, while the remainder of the withdrawn liquid was heated by reboiler 30 and returned to lower portion 28 of distillation column 50. The recovered liquid withdrawn from the bottom of column 50 was analyzed and, as a result, it was found that the liquid contained diethylene glycol and triethylene glycol in a concentration of 63% by weight in total. A gaseous fraction was withdrawn from column 50 through withdrawal port provided in a side wall of column 50 at a position 90 cm below the top of column 50 at a flow rate of 75 g/h, and condensed by condenser 33, and the resultant condensate (containing EG and EC in concentrations of 86.5% by weight and 13.5% by weight, respectively) was recovered from the system.

From the above data, it can be seen that the conversion of EC was 92%, the yield of DMC was 84% (DMC was produced at a production rate of 103 g/h), the selectivity for DMC was 94%, the yield of EG was 76% (EG was produced at a production rate of 64.3 g/h), and the selectivity for EG was 83%. It can also be seen that when EG is separated from a transesterification reaction mixture by distillation in the presence of a large amount of unreacted EC, the resultant distilled mixture as an EG fraction inevitably contains not only EG but also EC so that EG having high purity cannot be obtained, and diols having a high boiling point is inevitably by-produced. The volume (V) of the reaction zone in continuous multi-stage distillation column 1 was calculated as follows:

$$V = \pi \times 1.25^2 \times 250/1,000 = 1.23 \text{ liters}.$$

Therefore, the productivity of DMC in terms of space time yield was:

$$103/1.23 = 83.7 \text{ g/liter.h}.$$

EXAMPLE 3

Figure 4:
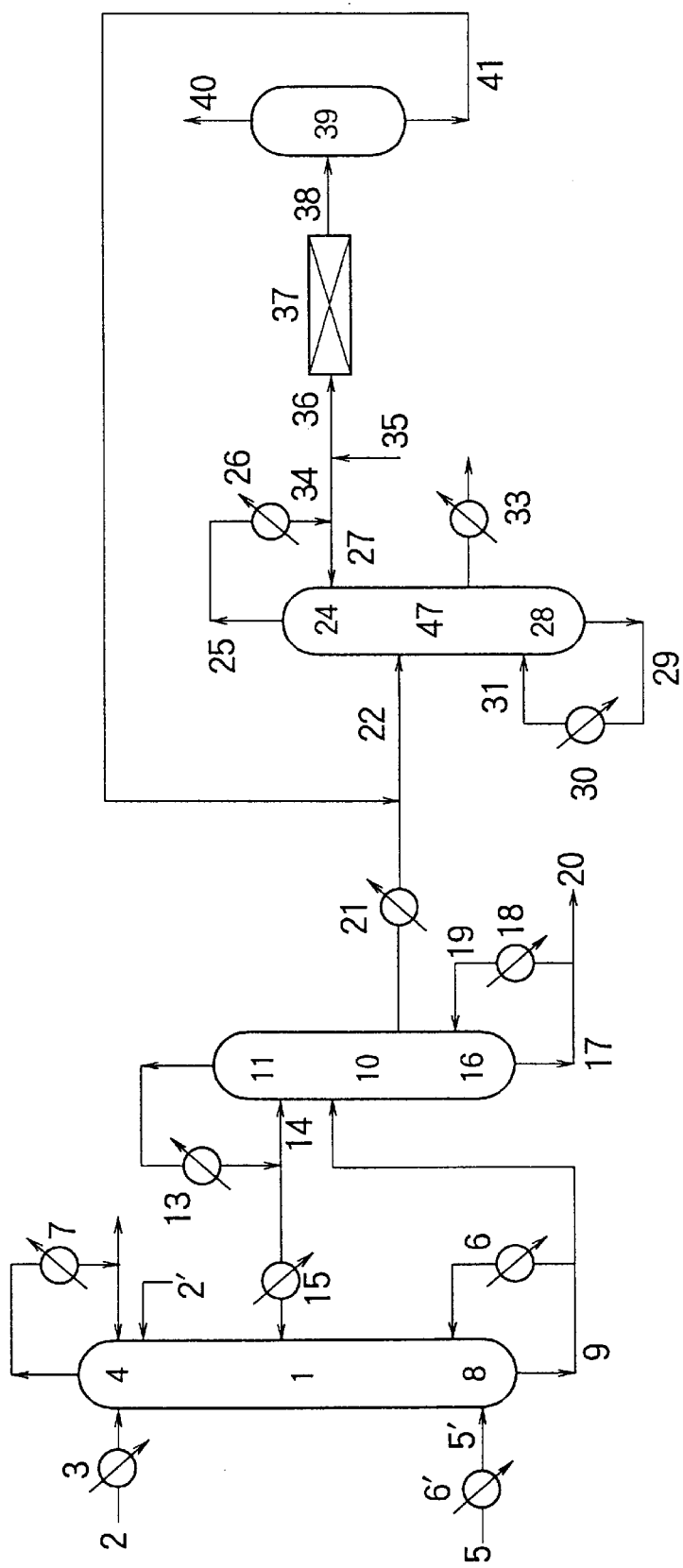
FIG. 4 is a diagram showing the system which was used for practicing Example 3 of the present application.

Using a system as shown in FIG. 4, dimethyl carbonate (DMC) and ethylene glycol (EG) were continuously produced from ethylene carbonate (EC) and methanol (MeOH).

A transesterification reaction was carried out in substantially the same manner as in Example 2, except that the flow rate of EC fed from conduit 2 was 160 g/h; the flow rate of the 3% by weight solution of sodium hydroxide in ethylene glycohol fed from conduit 2' was 11 g/h; the weight ratio of MeOH/DMC in the mixture of MeOH and DMC fed from conduit 5 was 85/15; the MeOH/DMC mixture was fed at a flow rate of 462 g/h to distillation column 1 at a position 100 cm above the bottom of the distillation column through evaporator 6' and conduit 5'; and distillation column 1 was equipped with a reboiler.

Continuous multi-stage distillation column 1 was operated under atmospheric pressure, and the temperature of upper portion 4 (above the uppermost portion) of distillation column 1 was 76° C. A gaseous mixture (containing MeOH and DMC in concentrations of 55.1% by weight and 44.9% by weight, respectively) distilled from the top of distillation column 1 was condensed by means of condenser 7. A part of the resultant condensate was returned to distillation column 1, and the remainder of the condensate was recovered from the system at a flow rate of 508 g/h.

A liquid reaction mixture (containing MeOH, DMC, EG and EC in concentrations of 23.3% by weight, 2.9% by weight, 70.6% by weight and 2.8% by weight, respectively) was withdrawn from the bottom of distillation column 1. A part of the liquid reaction mixture was fed to low boiling point mixture-separating column 10 which was of the same type as used in Example 2 at a position 40 cm below the top of column 10 at a flow rate of 170 g/h. The remainder of the liquid reaction mixture was heated by reboiler 6 and returned to lower portion 8 of distillation column 1 so that the MeOH/DMC weight ratio of the withdrawn liquid reaction mixture became 8.0. Low boiling point mixture-separating column 10 was operated under conditions such that the temperature of lower portion 16 (below the lowermost stage) and the pressure of upper portion 11 (above the uppermost stage) were 103° C. and $1.3 \times 10^3$ Pa (10 torr), respectively. A gaseous mixture containing MeOH and DMC was withdrawn from the top of column 10, and a part of the withdrawn liquid mixture was condensed by condenser 13 to obtain a condensate, and the obtained condensate was recycled in a gaseous form to distillation column 1 at the same position as described in Example 2 through evaporator 15 at a flow rate of 44.5 g/h. The remainder of the condensate was returned to upper portion 11 of column 10 through conduit 14. A liquid mixture (containing NaOH and EG in concentrations of 3% by weight and 97% by weight, respectively) was withdrawn from the bottom of column 10, and a part of the withdrawn liquid mixture was recovered through conduit 20 at a flow rate of 11 g/h, while the remainder of the withdrawn liquid mixture was returned to lower portion 16 of column 10. A gaseous mixture (containing EG and EC in concentrations of 95.8% by weight and 4.2% by weight, respectively) was withdrawn from column 10 through a withdrawal port provided in a side wall of column 10 at a flow rate of 114 g/h, and condensed by condenser 21 to obtain a condensate.

The condensate obtained in condenser 21 was mixed with a liquid mixture fed from conduit 41, which was withdrawn as a liquid phase from gas-liquid separator 39 (which was of the same type as used in Example 2), and the resultant mixture was fed to azeotoropic mixture-separating column 47 at a position 40 cm below the top of column 47. Azeotoropic mixture-separating column 47 was of substantially the same type as diol-separating column 23, and was operated in substantially the same manner as in the operation of diol-separating column 23. The temperature of lower portion (below the lowermost stage) 28 thereof and the pressure of upper portion 24 (above the uppermost stage) were 112° C. and $2.7 \times 10^3$ Pa (20 torr), respectively. A gaseous mixture withdrawn from the top of column 47 was condensed by condenser 26 to obtain a condensate, and a part of the obtained condensate was introduced to continuous hydrolysis reactor 37 (which was of the same type as used in Example 1) which was heated at 180° C., through conduit 34 at a flow rate of 55.2 g/h, together with water introduced through conduit 35 at a flow rate of 1.0 g/h. The weight ratio of water to EC in the water/EC mixture introduced to continuous hydrolysis reactor 37 was 0.6. The remainder of the condensate was returned to upper portion 24 of azeotropic mixture-separating column 47 through conduit 27. The inner pressure of continuous hydrolysis reactor 37 was maintained at $2.6 \times 10^6$ Pa (26 kg/cm$^2$-G). A hydrolysis reaction mixture was withdrawn from continuous hydrolysis reactor 37, and introduced to gas-liquid separator 39 through conduit 38, from which carbon dioxide was discharged through conduit 40, and a mixture of EG and water was withdrawn through conduit 41. From a withdrawal port provided in a side wall of azeotropic mixture-separating column 47, EG (EG content: not lower than 99.999% by weight; and the total content of EC and DEG: not higher than 0.1 ppb by weight) was recovered at a flow rate of 113 g/h.

From the above data, it can be seen that the conversion of EC was 100%, the yield of DMC was 97% (DMC was produced at a production rate of 158.8 g/h), the selectivity for DMC was not lower than 99%, the yield of EG having high purity was not lower than 99%, and the selectivity for EG was not lower than 99%. As apparent from the above, EC did not remain in the hydrolysis reaction mixture. The productivity of DMC in terms of the space time yield was 252.9 g/liter-h (158.8/0.628=252.9).

EXAMPLE 4

Figure 5:
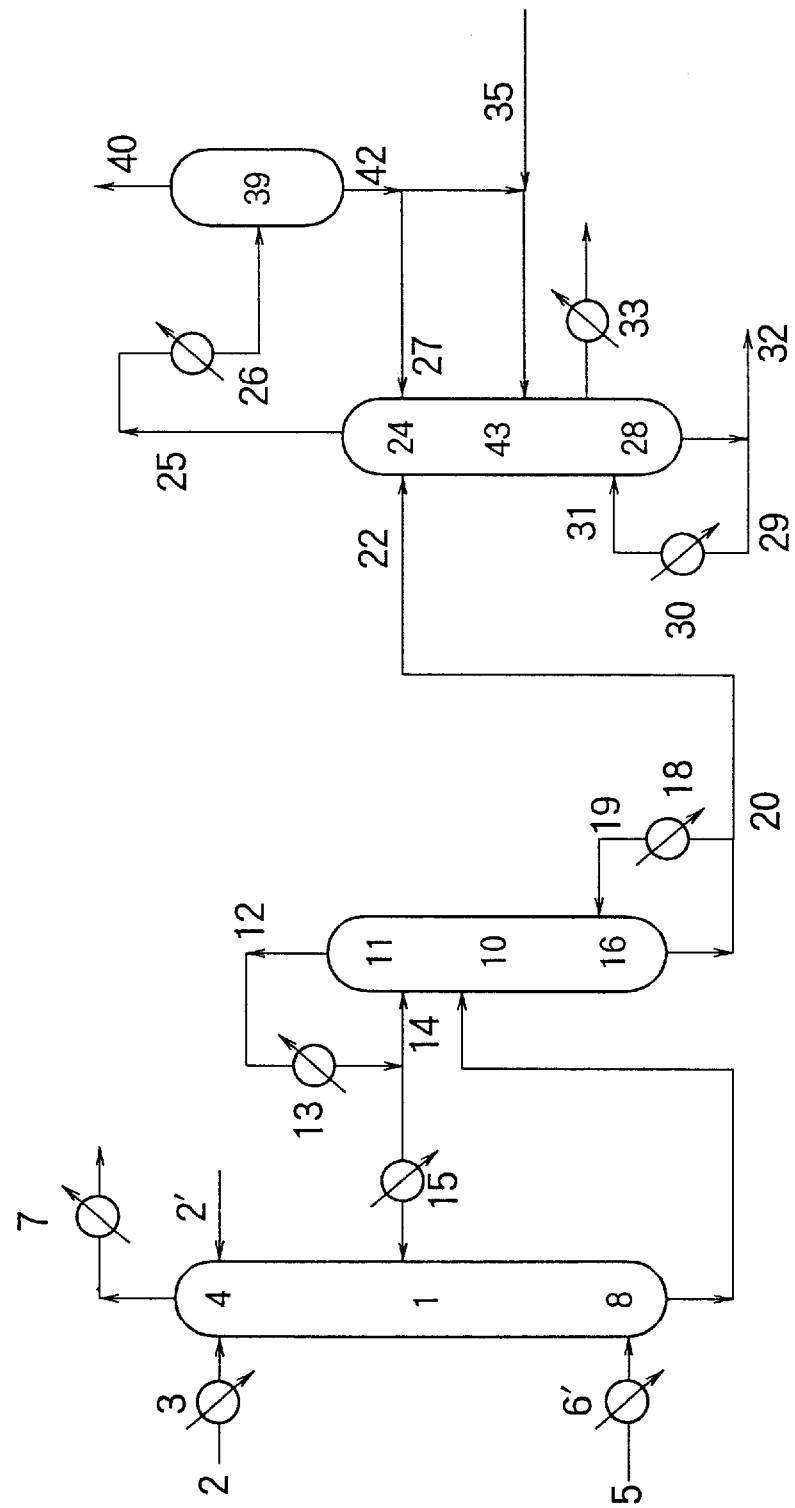
FIG. 5 is a diagram showing the system which was used for practicing Example 4 of the present application.

Using a system as shown in FIG. 5, dimethyl carbonate (DMC) and ethylene glycol (EG) were continuously produced from ethylene carbonate (EC) and methanol (MeOH).

Continuous multi-stage distillation column 1 was operated in substantially the same manner as in Example 2, except that the flow rate of EC fed through conduit 2 was 120 g/h, and the flow rate of a mixture of MeOH and DMC (weight ratio of MeOH/DMC=85/15) fed through conduit 5 was 330 g/h, to thereby effect a transesterification reaction. The temperature of upper portion (above the uppermost stage) 4 of distillation column 1 was 77° C.

A gaseous mixture distilled from the top of distillation column 1 was condensed by means of condenser 7, and the resultant condensate (containing MeOH and DMC in concentrations of 55.3% by weight and 44.7% by weight, respectively) was recovered from the system at a flow rate of 363 g/h. A liquid reaction mixture [containing a low boiling point mixture (comprised of MeOH and DMC), EG and EC in concentrations of 31.8% by weight, 61.2% by weight and 6.8% by weight, respectively] was withdrawn from the bottom of distillation column 1 at a flow rate of 141 g/h and fed to low boiling point mixture-separating column 10 (which was of the same type as used in Example 2) at a position 40 cm below the top of column 10.

Low boiling point mixture-separating column 10 was operated under conditions such that the pressure of upper portion 11 (above the uppermost stage) was $1.3 \times 10^3$ Pa (10 torr) and the temperature of lower portion 16 (below the lowermost stage) was 105° C. A gaseous mixture containing MeOH and DMC, withdrawn from the top of column 10 was condensed by means of condenser 13. A part of the resultant condensate was refluxed to upper portion 11 of column 10 through conduit 14 (reflux ratio: 2) while returning, through evaporator 15, the remainder of the condensate in a gaseous form to continuous multi-stage distillation column 1 at a position 120 cm below the top of distillation column 1 at a flow rate of 45 g/h. On the other hand, a part of a liquid (containing EG and EC in concentrations of 80.7% by weight and 10.0% by weight, respectively) was withdrawn from the bottom of column 10 through conduit 20 at a flow rate of 96.5 g/h, while the remainder of the withdrawn liquid was heated by reboiler 18 and returned to lower portion 16 of column 10. The liquid withdrawn from the bottom of low boiling point mixture-separating column 10 was fed to upper portion 24 of continuous hydrolysis reaction column 43 through conduit 22, which column 43 had been packed with Dixon packings (6 mm φ) and was comprised of a column having an inner diameter of 5 cm and a packing height of 150 cm. Continuous hydrolysis reaction column 43 was operated under conditions such that the pressure of upper portion (above the uppermost stage) 24 thereof was $2.5 \times 10^4$ Pa (190 torr) and the temperature of lower portion (below the lowermost stage) 28 thereof was 156° C. A gaseous mixture distilled from the top of column 43 was condensed by means of condenser 26 and introduced to gas-liquid separator 39, from which carbon dioxide was discharged through conduit 40 and a mixture of EG and water was withdrawn through conduit 42 at a flow rate of 30.8 g/h. A half of the withdrawn mixture was refluxed to upper portion 24 of column 43 through conduit 27 while returning the remainder of the withdrawn mixture to continuous hydrolysis reaction column 43 at a position 100 cm below the top of column 43, together with water which was introduced through conduit 35 at a flow rate of 2.0 g/h. The weight ratio of EC to water in the EC/water mixture introduced to continuous hydrolysis reaction column 43 was 0.5. A gaseous fraction was withdrawn from column 43 through a withdrawal port provided in a side wall of column 43 at a position 130 cm below the top of column 43 at a flow rate of 84.5 g/h, and condensed by means of condenser 33, to thereby obtain EG (EG content: not lower than 99.999% by weight; and the total content of EC and DEG: not higher than 0.1 ppb by weight). On the other hand, a liquid (containing EG in a concentration of 97% by weight) was withdrawn from the bottom of column 43, and a part of the withdrawn liquid was recovered through conduit 32 at a flow rate of 9 g/h, while the remainder of the withdrawn liquid was heated by reboiler 30 and returned to lower portion 28 column 43.

From the above data, it can be seen that the conversion of EC was 100%, the yield of DMC was 92% (DMC was produced at a production rate of 112.9 g/h), the selectivity for DMC was not lower than 99%, the yield of EG having high purity was not lower than 99%, and the selectivity for EG was not lower than 99%. As apparent from the above, EC did not remain in the hydrolysis reaction mixture. Also, the productivity of DMC in terms of the space time yield was: 112.9/0.628=179.8 g/liter.h.

EXAMPLE 5

Figure 6:
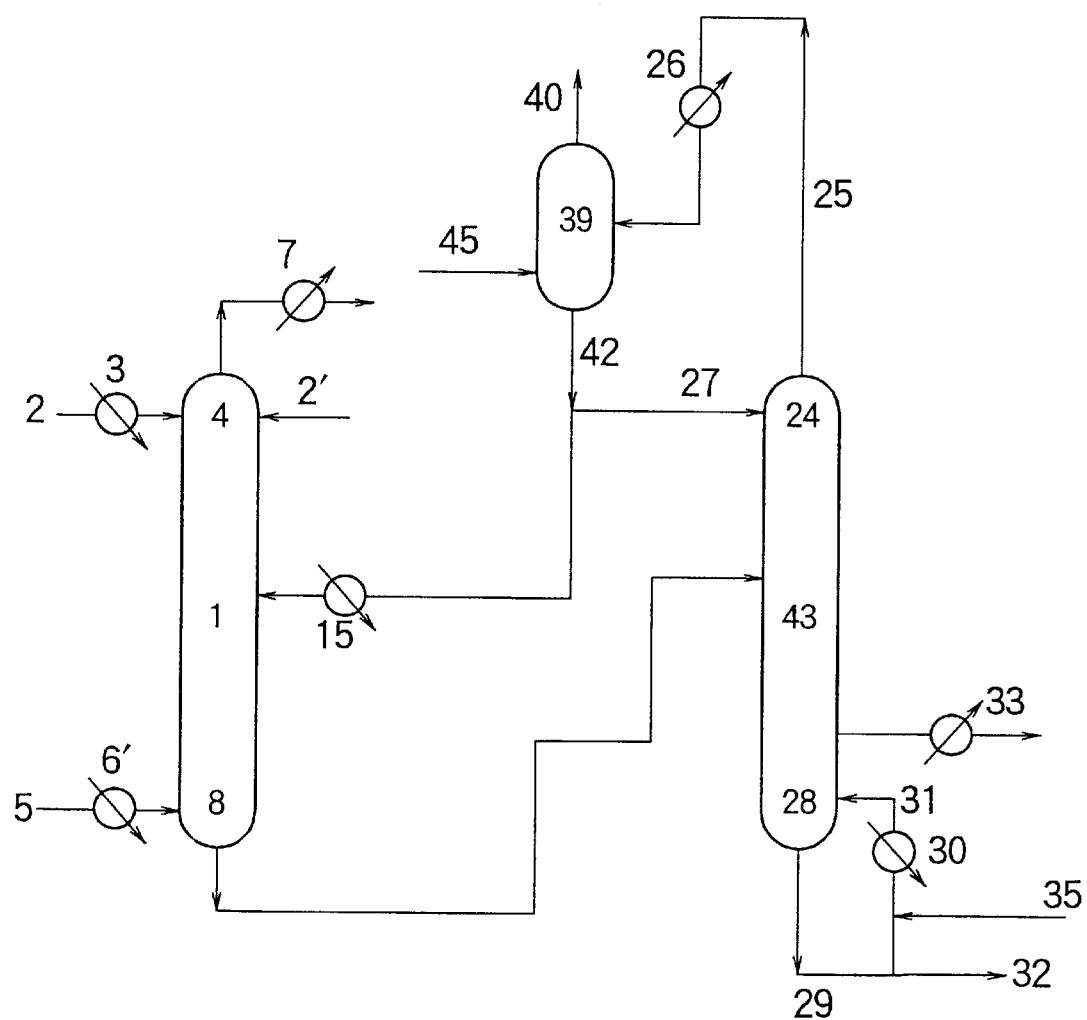
FIG. 6 is a diagram showing the system which was used for practicing Example 5 of the present application.

Using a system as shown in FIG. 6, dimethyl carbonate (DMC) and ethylene glycol (EG) were continuously produced from ethylene carbonate (EC) and methanol (MeOH).

Using the same continuous multi-stage distillation column 1 as in Example 2, a transesterification reaction was performed in substantially the same manner as in Example 2, except that the flow rate of EC fed from conduit 2 was 120 g/h, and the flow rate of the low boiling point mixture of MeOH and DMC (weight ratio of MeOH/DMC=85/15) fed from conduit 5 was 305 g/h. The temperature of upper portion 4 (above the uppermost stage) of continuous multi-stage distillation column 1 was 78° C. A gaseous mixture distilled from the top of distillation column 1 was condensed by means of condenser 7, and the resultant condensate (containing MeOH and DMC in concentrations of 53.1% by weight and 46.9% by weight, respectively) was recovered from the system at a flow rate of 337 g/h. A liquid reaction mixture [containing a low boiling point mixture (comprised of MeOH and DMC), EG and EC in concentrations of 33.8% by weight, 59.0% by weight and 7.1% by weight, respectively] withdrawn from the bottom of distillation column 1 at a flow rate of 146 g/h was fed to continuous hydrolysis reaction column 43 at a position 90 cm below the top of column 43, which was comprised of a column having in an inner diameter of 5 cm and a packing height of 250 cm, and had been packed with Dixon packings (6 mm φ). Continuous hydrolysis reaction column 43 was operated under conditions such that the pressure of upper portion (above the uppermost stage) 24 thereof was $2.7 \times 10^4$ Pa (200 torr) and the temperature of lower portion (below the lowermost stage) 28 thereof was 161° C. A gaseous mixture distilled from the top of continuous hydrolysis reaction column 43 was condensed by means of condenser 26, and the resultant condensate was introduced to gas-liquid separator 39, from which carbon dioxide was discharged through conduit 40 and a mixture of MeOH and DMC in a liquid form was withdrawn from the bottom of gas-liquid separator 39 through conduit 42 at a flow rate of 171.5 g/h. During the gas-liquid separation, nitrogen gas was introduced to gas-liquid separator 39 through conduit 45 provided on the lower portion of separator 39 in order to separate carbon dioxide from the liquid mixture of MeOH and DMC. A part of the MeOH/DMC mixture was refluxed to upper portion 24 of continuous hydrolysis reaction column 43 through conduit 27 while returning, through evaporator 15, the remainder of the mixture in a gaseous form to continuous multi-stage distillation column 1 at a position 120 cm below the top of distillation column 1 at a flow rate of 49 g/h.

A part of a liquid (containing EG in a concentration of 97% by weight) was withdrawn from the bottom of continuous hydrolysis reaction column 43 at a flow rate of 9 g/h through conduit 32, and the remainder of the liquid was heated by reboiler 30 and returned to lower portion 28 of continuous hydrolysis reaction column 43 through conduit 31, together with water which was introduced to the inlet of reboiler 30 at a flow rate of 2.1 g/h so that the concentration of water in the above-mentioned condensate derived from the gaseous mixture distilled from the top of column 43 was maintained at a concentration not higher than 50 ppm. The weight ratio of water to EC introduced to continuous hydrolysis reaction column 43 was 0.3. A mixture of EG and a small amount of water was recovered from a withdrawal port provided in the side wall of continuous hydrolysis reaction column 43 at a position 230 cm below the top of column 43 through condenser 33. The recovered mixture was analyzed and, as a result, it was found that the recovered liquid mixture contained only EG and water. The flow rate of the mixture, after removal of the water, was 85 g/h. The EG content of the mixture was not lower than 99.999% by weight.

From the above data, it can be seen that the conversion of EC was 100%, the yield of DMC was 91% (DMC was produced at a production rate of 111.7 g/h), the selectivity for DMC was not lower than 99%, the yield of EG having high purity was not lower than 99%, and the selectivity for EG was not lower than 99%. As apparent from the above, EC did not remain in the hydrolysis reaction mixture. Also, the productivity of DMC in terms of the space time yield was: 111.7/0.628=177.9 g/liter.h.

EXAMPLE 6

Figure 7:
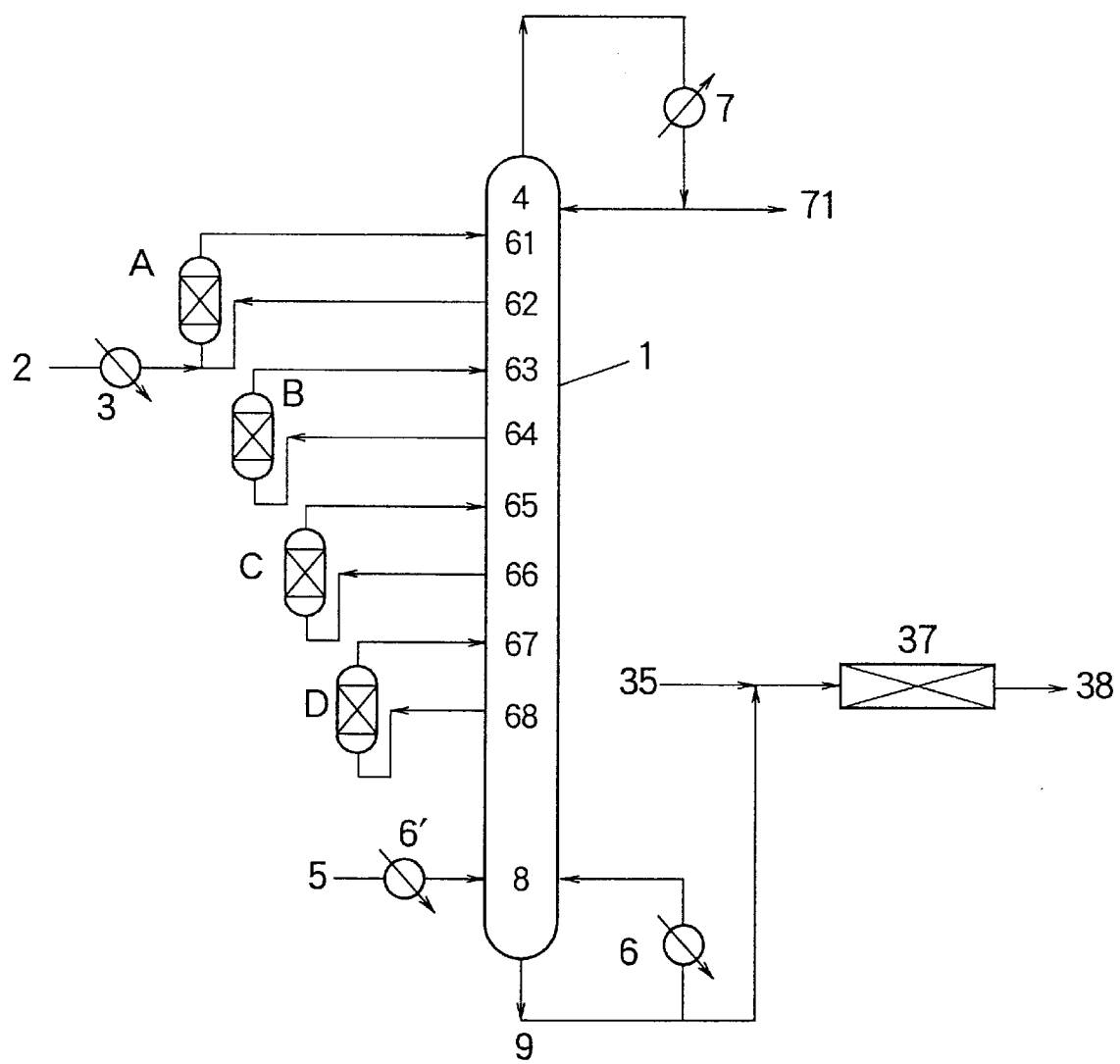
FIG. 7 is a diagram showing the system which was used for practicing Example 6 of the present application.

Using a system as shown in FIG. 7, dimethyl carbonate (DMC) and ethylene glycol (EG) were continuously produced from ethylene carbonate (EC) and methanol (MeOH).

Stainless-steel Dixon packings (6 mm $\phi$) were packed in continuous multi-stage distillation column 1, which was comprised of a column having an inner diameter of 2 cm and a packing height of 200 cm. Between a position 10 cm below the top of distillation column 1 and a position 50 cm above the bottom of the distillation column 1, respective inlets 61, 63, 65 and 67 and respective withdrawal ports 62, 64, 66 and 68 for transesterification reactors A, B, C and D were provided in a side wall of distillation column 1 as shown in FIG. 7. Each of transesterification reactors A, B, C and D fluid-tightly communicates with distillation column 1. The internal volumes of transesterification reactors A, B, C and D were 200 ml, 100 ml, 100 ml and 100 ml, respectively. Each of the transesterification reactors was packed with an anion-exchange resin (a catalyst for transesterification reaction) having a quaternary ammonium group as an ion-exchange group [which anion-exchange resin had been obtained by subjecting a Cl⁻ type of Dowex (registered trademark) MSA-1 resin (manufactured and sold by Dow Chemical Co., U.S.A.) to ion-exchange with a 2N aqueous solution of $Na_2CO_3$ so that about 50% of the Cl⁻ ions were converted to $CO_3^{2-}$ ions, and the resultant resin was washed repeatedly with purified water and then with dried methanol to effect dehydration and drying of the resin].

EC was continuously fed to transesterification reactor A through conduit 2 and preheater 3 (by which EC was preheated to 70° C.) at a flow rate of 135 g/h, and MeOH was continuously fed to lower portion 8 (below the lowermost stage) of distillation column 1 in a gaseous form through conduit 5 and evaporator 6' at a flow rate of 327 g/h, to thereby effect a transesterification reaction. Continuous multi-stage distillation column 1 was operated under atmospheric pressure, and the temperature of upper portion 4 (above the uppermost stage) of distillation column 1 was 64° C. The liquid flowing-down inside continuous multi-stage distillation column 1 was withdrawn from each of the withdrawal ports provided in the side wall of distillation column 1, and the withdrawn liquid was introduced to the respective transesterification reactor corresponding to each withdrawal port. The flow rate of the liquid introduced to each transesterification reactor was set at 0.5 liter/h, and the temperature and pressure of each transesterification reactor were set at 70° C. and about $4.9 \times 10^5$ Pa (5 kg/cm²-G), respectively. A transesterification reaction mixture, obtained by the transesterification reaction performed in each transesterification reactor, containing dimethyl carbonate (DMC) and ethylene glycol (EG) in increased concentrations, was returned to distillation column 1. As a result of the contact of the liquid flowing-down inside distillation column 1 with a vapor ascending from the bottom toward the top of distillation column 1, the respective concentrations of DMC (product) and EC (starting material) in the flowing-down liquid decreased.

A gaseous mixture distilled from the top of distillation column 1 was condensed by means of condenser 7 to obtain a condensate (containing MeOH and DMC in concentrations of 63.7% by weight and 36.3% by weight, respectively), and a part of the resultant condensate was refluxed to upper portion 4 of distillation column 1 (reflux ratio: 2) while the remainder of the condensate was withdrawn from the system through conduit 71 at a flow rate of 365 g/h. On the other hand, a liquid reaction mixture (containing MeOH, DMC, EG and EC in concentrations of 26.1% by weight, 1.9% by weight, 68.0% by weight and 4.0% by weight, respectively) was withdrawn from the bottom of distillation column 1, and a part of the withdrawn reaction mixture was heated by reboiler 6 and returned to lower portion 8 of distillation column 1. The remainder of the reaction mixture was withdrawn at a flow rate of 134 g/h, and introduced to continuous hydrolysis reactor 37 [which was of the same type as used in Example 1, and the internal temperature and pressure of which was maintained at 170° C. and $2.5 \times 10^6$ Pa (25 kg/cm²-G), respectively], together with water which was introduced via conduit 35 at a flow rate of 5.3 g/h, to thereby effect a continuous hydrolysis of EC in the reaction mixture. The resultant hydrolysis reaction mixture was recovered through conduit 38 at a flow rate of 140 g/h. The recovered hydrolysis reaction mixture was analyzed and, as a result, it was found that the hydrolysis reaction mixture contained MeOH, DMC and EG in concentrations of 25.1% by weight, 1.9% by weight and 68.1% by weight, respectively.

From the above data, it can be seen that the conversion of EC was 100%, the yield of DMC was 96% (DMC was produced at a production rate of 132.6 g/h), the selectivity for DMC was not lower than 99%, the yield of EG having high purity (which contained no EC) was not lower than 99%, and the selectivity for EG was not lower than 99%. As apparent from the above, EC did not remain in the hydrolysis reaction mixture. Also, the total volume (V) of the reaction zones in transesterification reactors A, B, C and D was calculated as follows: V=0.2+0.1+0.1+0.1=0.5 liter.

Therefore, the productivity of DMC in terms of the space time yield was: 132.6/0.5=265.2 g/liter.h.

EXAMPLE 7

Figure 8:
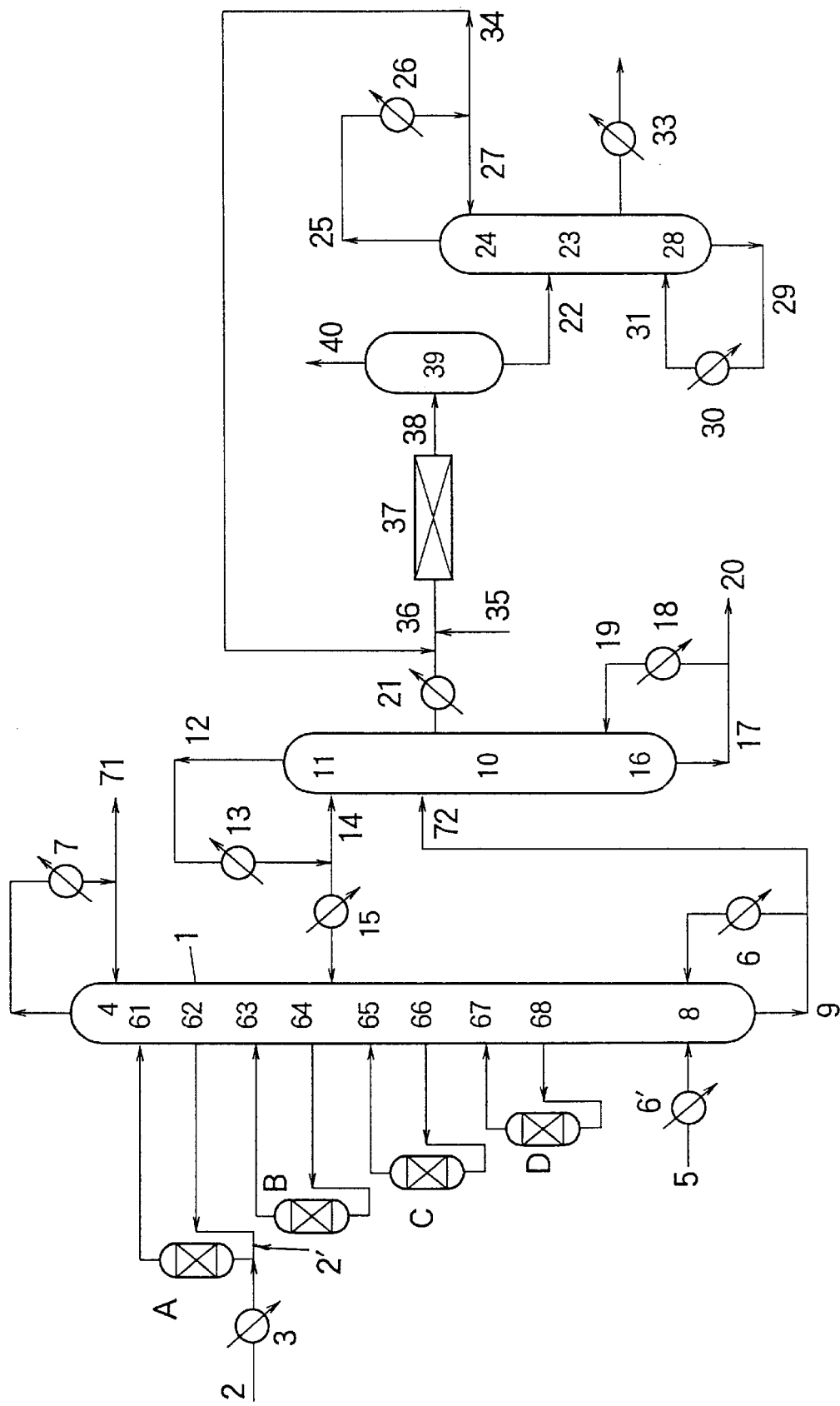
FIG. 8 is a diagram showing the system which was used for practicing Example 7 of the present application.

Using a system as shown in FIG. 8, dimethyl carbonate (DMC) and ethylene glycol (EG) were continuously produced from ethylene carbonate (EC) and methanol (MeOH).

Continuous multi-stage distillation column 1 was operated in substantially the same manner as in Example 6, except that stainless-steel Dixon packings (6 mm φ) were packed in each of the transesterification reactors instead of the anion-exchange resin used in Example 6, that EC was fed to the transesterification reactor through conduit 2 at a flow rate of 240 g/h, that a 3% by weight solution of sodium hydroxide (as a catalyst) in ethylene glycol was also continuously fed to transesterification reactor A through conduit 2' at a flow rate of 22 g/h, and that a mixture of MeOH and DMC (weight ratio of MeOH/DMC=95/5) was fed to lower portion 8 (below the lowermost stage) of continuous multistage distillation column 1 through conduit 5 at a flow rate of 628 g/h, to thereby effect a transesterification reaction. Continuous multi-stage distillation column 1 was operated under atmospheric pressure, and the temperature of upper portion 4 (above the uppermost stage) of distillation column 1 was 64° C. A gaseous mixture (containing MeOH and DMC in concentrations of 62.6% by weight and 37.4% by weight, respectively) was distilled from the top of continuous multistage distillation column 1 was condensed by condenser 7 to obtain a condensate. A part of the obtained condensate was recovered from the system at a flow rate of 694 g/h. The remainder of the condensate was recycled to upper portion 4 of distillation column 1. A liquid reaction mixture [containing a low boiling point mixture (comprised of MeOH and DMC), EG and EC in concentrations of 29% by weight, 65.1% by weight and 6.1% by weight, respectively] was withdrawn from the bottom of distillation column 1. A part of the withdrawn reaction mixture was fed to low boiling point mixture-separating column 10 at a position 40 cm below the top of column 10 at a flow rate of 274 g/h, which column 10 was comprised of a column having an inner diameter of 2.5 cm and a packing height of 120 cm, and had been packed with Dixon packings (3 mm φ). The remainder of the withdrawn reaction mixture was heated by reboiler 6 and returned to lower portion 8 of distillation column 1. Low boiling point mixture-separating column 10 was operated under conditions such that the pressure of upper portion 11 (above the uppermost stage) was $1.3 \times 10^3$ Pa (10 torr) and the temperature of lower portion 16 (below the lowermost stage) was 101° C. A gaseous mixture containing MeOH and DMC, distilled from the top of low boiling point mixture-separating column 10, was condensed by means of condenser 13. A part of the resultant condensate was refluxed through conduit 14 (reflux ratio: 2) while the remainder of the condensate was recycled in a gaseous form to continuous multi-stage distillation column 1 at a position 100 cm below the top of distillation column 1 at a flow rate of 78 g/h. On the other hand, a liquid (containing EG and NaOH in concentrations of 97% by weight and 3% by weight, respectively) was withdrawn from the bottom of column 10, and a part of the withdrawn liquid was recovered from the system through conduit 20 at a flow rate of 22 g/h, while the remainder of the withdrawn liquid was heated by reboiler 18 and returned to lower portion 16 of low boiling point mixture-separating column 10. A gaseous mixture containing EG and EC was withdrawn from a withdrawal port provided in a side wall of column 10 at a position 90 cm below the top of column 10 at a flow rate of 174 g/h, and condensed by means of condenser 21 to obtain a condensate (containing EG and EC in concentrations of 90.3% by weight and 9.7% by weight, respectively).

The condensate obtained by condenser 21 was introduced to continuous hydrolysis reactor 37 [which was of the same type as used in Example 1, and the internal temperature and pressure of which were maintained at 180° C. and $2.5 \times 10^6$ Pa (25 kg/cm²-G), respectively], together with a liquid obtained by condensing a gaseous mixture withdrawn from the top of diol-separating column 23 through conduit 34, and water which was introduced via conduit 35 at a flow rate of 3.4 g/h, to thereby effect a continuous hydrolysis reaction of the condensate obtained by condenser 21. The weight ratio of water to EC in the mixture introduced to continuous hydrolysis reactor 37 was 0.5. A hydrolysis reaction mixture was withdrawn and introduced to gas-liquid separator 39 through conduit 38, from which carbon dioxide was discharged through conduit 40 and a mixture of EG and water was withdrawn through conduit 22.

The withdrawn mixture of EG and water was fed to diol-separating column 23 at a position 40 cm below the top thereof, which column 23 was comprised of a column having an inner diameter of 2.5 cm and a packing height of 120 cm, and had been packed with Dixon packings (3 mm φ).

Diol-separating column 23 was operated under a pressure of $2.7 \times 10^3$ Pa (20 torr) as measured at upper portion 24 (above the uppermost stage). A gaseous mixture distilled from the top of diol-separating column 23 was condensed by means of condenser 26, and a part of the resultant condensate was refluxed to the upper portion of column 23 through conduit 27 (reflux ratio: 2) while the remainder of the condensate was returned to continuous hydrolysis reactor 37 through conduit 34 at a flow rate of 5.0 g/h. A liquid withdrawn from the bottom of diol-separating column 23 was heated by reboiler 30 and returned to column 23. The temperature of lower portion 28 (below the lowermost stage) of diol-separating column 23 was 110° C. Also, a gaseous fraction was recovered from a withdrawal port provided in a side wall of column 23 at a position 90 cm below the top of column 23 at a flow rate of 169 g/h, and condensed by means of condenser 33, to thereby obtain EG (EG content: not lower than 99.999% by weight; and the total content of EC and DEG: not higher than 0.1 ppb by weight).

From the above data, it can be seen that the conversion of EC was 100%, the yield of DMC was 93% (DMC was produced at a production rate of 228.3 g/h), the selectivity for DMC was not lower than 99%, the yield of EG having high purity was not lower than 99%, and the selectivity for EG was not lower than 99%. As apparent from the above, EC did not remain in the hydrolysis reaction mixture. Also, the volume (V) of the reaction zone was calculated as follows: V=(total volume of the transesterification reactors) +(volume of the continuous multi-stage distillation column) =(0.2+0.1+0.1+0.1)+0.628=1.13 liters. Therefore, the productivity of DMC in terms of the space time yield was: 228.3/1.13=202.4 g/liter.h.

EXAMPLE 8

Figure 9:
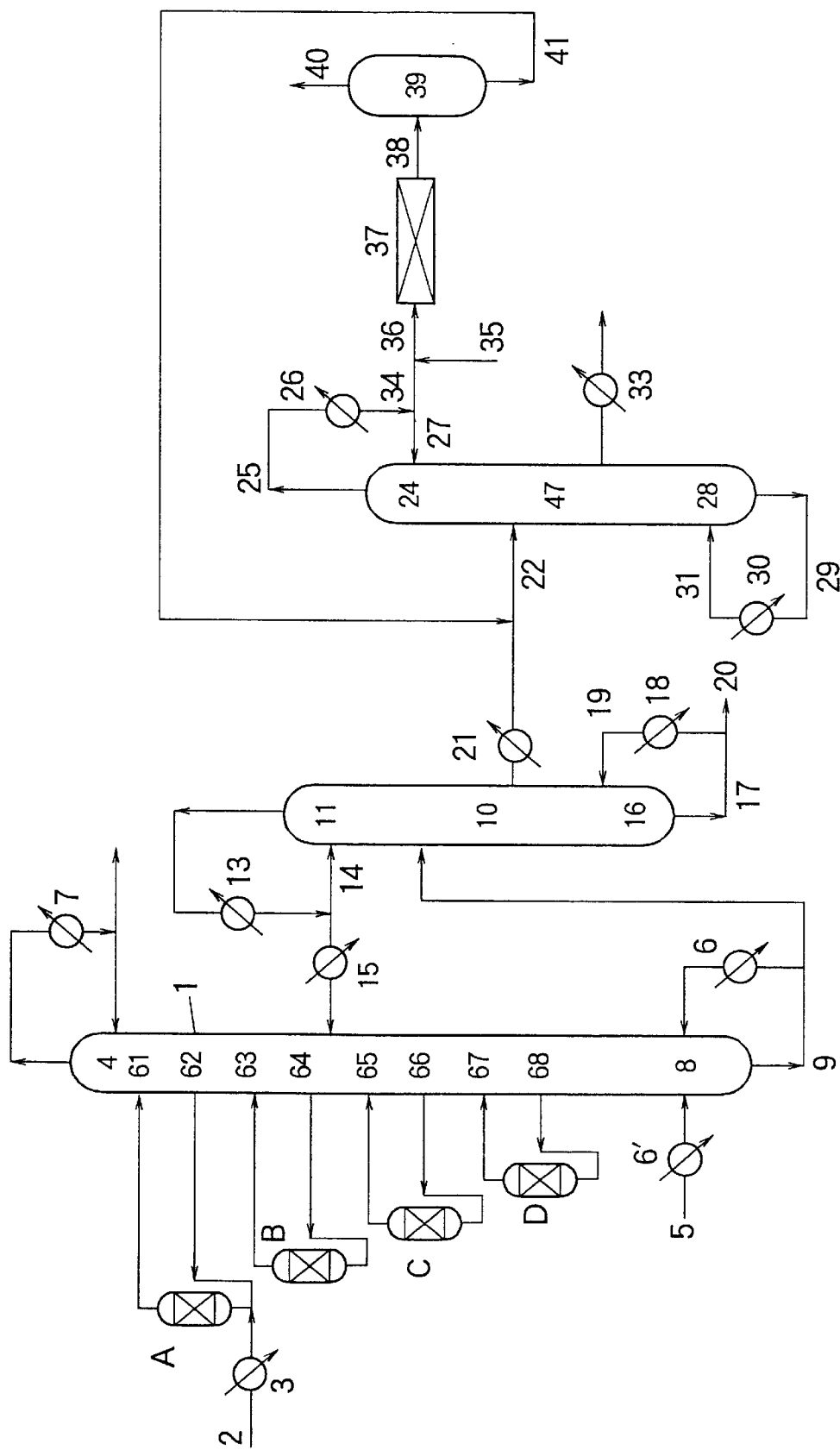
FIG. 9 is a diagram showing the system which was used for practicing Example 8 of the present application.

Using a system as shown in FIG. 9, dimethyl carbonate (DMC) and ethylene glycol (EG) were continuously produced from ethylene carbonate (EC) and methanol (MeOH).

An anion-exchange resin was packed in each of transesterification reactors A, B, C and D. Continuous multi-stage distillation column 1 was operated in substantially the same manner as in Example 6, except that the flow rate of EC fed through conduit 2 was 132 g/h, and a mixture of MeOH and DMC (weight ratio of MeOH/DMC=85/15) was fed through conduit 5 at a flow rate of 381 g/h, to thereby effect a transesterification reaction. Continuous multi-stage distillation column 1 was operated under atmospheric pressure, and the temperature of upper portion 4 (above the uppermost stage) of distillation column 1 was 64° C. A gaseous mixture (containing MeOH and DMC of 55.1% by weight and 44.9% by weight, respectively) distilled from the top of continuous multi-stage distillation column 1 was condensed by condenser 7 to obtain a condensate. A part of the obtained condensate was recovered from the system at a flow rate of 419 g/h. The remainder of the condensate was returned to upper portion 4 of distillation column 1. A liquid reaction mixture [containing a low boiling point mixture (comprised of MeOH and DMC), EG and EC in concentrations of 29% by weight, 68.0% by weight and 3.0% by weight, respectively] was withdrawn from the bottom of distillation column 1. A part of the withdrawn reaction mixture was fed, at a flow rate of 133 g/h, to low boiling point mixture-separating column 10 (which was of the same type as used in Example 7) at a position 40 cm below the top of column 10. The remainder of the withdrawn reaction mixture was heated by reboiler 6 and returned to lower portion 8 (below the lowermost stage) of distillation column 1.

Low boiling point mixture-separating column 10 was operated in substantially the same manner as in Example 7, except that a liquid was not withdrawn from the bottom of low boiling point mixture-separating column 10 through conduit 20. The temperature of lower portion 16 (below the lowermost stage) and pressure of upper portion 11 (above the uppermost stage) of low boiling point mixture-separating column 10 were 102° C. and $1.3 \times 10^3$ Pa (10 torr), respectively. A gaseous mixture containing MeOH and DMC distilled from the top of low boiling point mixture-separating column 10 was condensed by condenser 13 to obtain a condensate. A part of the obtained condensate was returned to upper portion 11 of column 10 through conduit 14, and the remainder of the condensate was recycled in a gaseous form to continuous multi-stage distillation column 1 at a position 100 cm below the top of column 1 through evaporator 15 at a flow rate of 38.5 g/h. A gaseous mixture (containing EG and EC in concentrations of 95.8% by weight and 4.2% by weight, respectively) was withdrawn from a withdrawal port provided in a side wall of low boiling point mixture-separating column 10 at a flow rate of 94 g/h, and condensed by means of condenser 21 to thereby obtain a condensate. The obtained condensate was fed to azeotropic mixture-separating column 47 at a position 40 cm below the top of column 47, together with a liquid phase introduced through conduit 41, withdrawn from gas-liquid separator 39 (which was of the same type as used in Example 2).

As azeotropic mixture-separating column 47, the same type of column as the diol-separating column 23 used in Example 7 was employed. Azeotropic mixture-separating column 47 was operated under conditions such that the pressure of upper portion 24 (above the uppermost stage) was $2.7 \times 10^3$ Pa (20 torr), and the temperature of lower portion 28 (below the lowermost stage) was 112° C. A gaseous mixture distilled from the top of azeotropic mixture-separating column 47 was condensed by condenser 26 to obtain a condensate. A part of the obtained condensate was fed to continuous hydrolysis reactor 37 [which was of the same type as used in Example 7, and the temperature and internal pressure of which were maintained at 180° C. and $2.6 \times 10^6$ Pa (26 kg/cm²-G), respectively] through conduit 34 at a flow rate of 45.6 g/h, together with water which was introduced via conduit 35 at a flow rate of 0.8 g/h, to thereby effect a continuous hydrolysis reaction of EC in the condensate (the weight ratio of water to EC introduced to reactor 37 was 0.6). The remainder of the condensate was refluxed to the upper portion of azeotropic mixture-separating column 47 (reflux ratio: 2). A hydrolysis reaction mixture withdrawn from hydrolysis reactor 37 was fed to gas-liquid separator 39 through conduit 38, from which carbon dioxide was discharged through conduit 40 and a mixture of EG and water was withdrawn through conduit 41. From a withdrawal port provided in a side wall of azeotropic mixture-separating column 47, EG (EG content: not lower than 99.999% by weight; and the total content of EC and DEG: not higher than 0.1 ppb) was recovered at a flow rate of 93 g/h.

From the above data, it can be seen that the conversion of EC was 100%, the yield of DMC was 97% (DMC was produced at a production rate of 131 g/h), the selectivity for DMC was not lower than 99%, the yield of high purity EG was not lower than 99%, and the selectivity for EG was not lower than 99%. As apparent from the above, EC did not remain in the hydrolysis reaction mixture. Also, the productivity of DMC in terms of the space time yield was: 131/0.5=262 g/liter.h.

EXAMPLE 9

Figure 10:
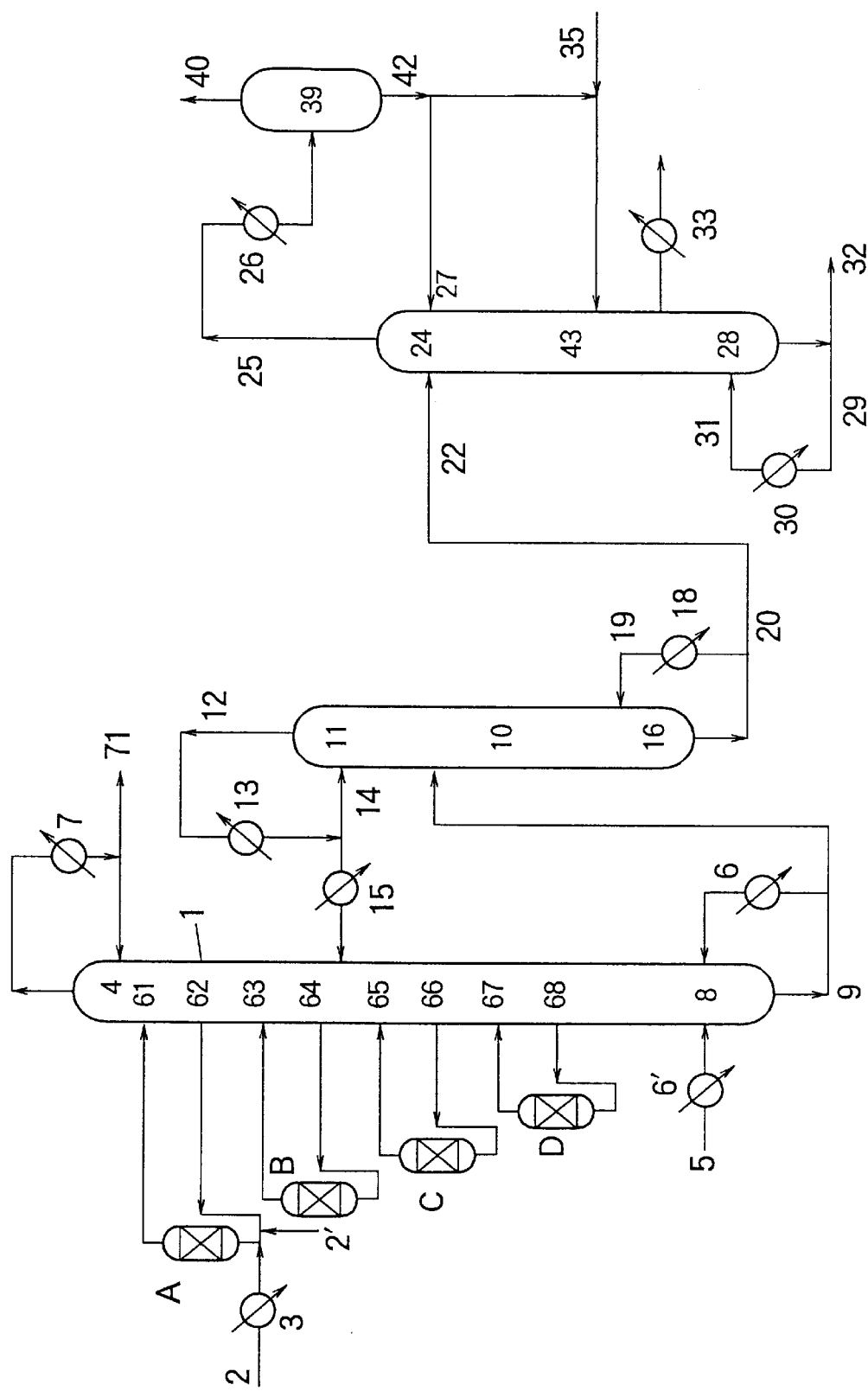
FIG. 10 is a diagram showing the system which was used for practicing Example 9 of the present application.

Using a system as shown in FIG. 10, dimethyl carbonate (DMC) and ethylene glycol (EG) were continuously produced from ethylene carbonate (EC) and methanol (MeOH).

Continuous multi-stage distillation column 1 was operated in substantially the same manner as in Example 7. That is, the respective flow rates of EC (fed through conduit 2), a mixture of MeOH and DMC (fed through conduit 5), and a solution of sodium hydroxide (as a catalyst) in ethylene glycol (fed through conduit 2') were the same as in Example 7, and the respective compositions of the MeOH/DMC mixture and the catalyst solution were the same as in Example 7. Continuous multi-stage distillation column 1 was operated under atmospheric pressure, and the temperature of upper portion 4 (above the uppermost stage) of the distillation column was 64° C.

A gaseous mixture distilled from the top of distillation column 1 was condensed by condenser 7. A part of the resultant condensate (containing MeOH and DMC in concentrations of 62.6% by weight and 37.4% by weight, respectively) was recovered from the system through conduit 71 at a flow rate of 694 g/h, and the remainder of the condensate was returned to upper portion 4 of distillation column 1. A liquid reaction mixture [containing low boiling point mixture (comprised of MeOH and DMC), EG and EC in concentrations of 28.5% by weight, 65.1% by weight and 6.1% by weight, respectively] was withdrawn from the bottom of distillation column 1. A part of the withdrawn reaction mixture was fed, at a flow rate of 274 g/h, to low boiling point mixture-separating column 10 [which was of the same type as used in Example 7] at a position 40 cm below the top of column 10 through conduit 9. The remainder of the withdrawn reaction mixture was heated by reboiler 6 and returned to lower portion 8 (below the lowermost stage) of distillation column 1.

Low boiling point mixture-separating column 10 was operated under conditions such that the pressure of upper portion 11 (above the uppermost stage) was $1.3 \times 10^3$ Pa (10 torr) and the temperature of lower portion 16 (below the lowermost stage) was 103° C. A gaseous mixture (containing MeOH and DMC) withdrawn from the top of column 10 was condensed by condenser 13 to obtain a condensate. A part of the obtained condensate was refluxed to upper portion 11 of column 10 through conduit 14 (reflux ratio: 2) while returning, through evaporator 15, the remainder of the condensate in a gaseous form to continuous multi-stage distillation column 1 at a position 120 cm below the top of distillation column 1 at a flow rate of 78 g/h. A liquid mixture (containing EG and EC in concentrations of 91.1% by weight and 8.6% by weight, respectively) was withdrawn from the bottom of column 10, and a part of the withdrawn liquid mixture was heated by reboiler 18 and returned to lower portion 16 of column 10, while the remainder of the withdrawn mixture was fed to upper portion 24 (above the uppermost stage) of continuous hydrolysis reaction column 43 having an inner diameter of 5 cm and a packing height of 150 cm, and having been packed with stainless-steel Dixon packings (6 mm $\phi$), through conduit 22 at a flow rate of 196 g/h.

Continuous hydrolysis reaction column 43 was operated under conditions such that the pressure of upper portion 24 of the reactor was $2.5 \times 10^4$ Pa (190 torr) and the temperature of lower portion 28 (below the lowermost stage) was 156° C. A gaseous mixture distilled from the top of continuous hydrolysis reaction column 43 was condensed by condenser 26, and the resultant condensate was introduced to gas-liquid separator 39, from which carbon dioxide was discharged through conduit 40 and a mixture of EG and water was withdrawn through conduit 42 at a flow rate of 58 g/h. A half of the withdrawn EG/water mixture was returned to upper portion 24 of continuous hydrolysis reaction column 43 through conduit 27, while returning the remainder of the mixture to continuous hydrolysis reaction column 43 at a position 100 cm below the top of column 43, together with water which was introduced via conduit 35. The weight ratio of water/EG in the mixture introduced to column 43 was 0.5. A gaseous fraction was withdrawn, at a flow rate of 169 g/h, from a withdrawal port provided in the side wall of column 43 at a position 130 cm below the top of column 43, and condensed by condenser 33, to thereby obtain EG [EG content: not lower than 99.999% by weight; and the total content of EC and DEG: not higher than 0.1 ppb by weight]. A hydrolysis reaction mixture (containing EG in a concentration of 97% by weight) was withdrawn from the bottom of column 43, and a part of the withdrawn mixture was recovered from the system through conduit 32 at a flow rate of 22 g/h, while the remainder of the withdrawn mixture was heated by reboiler 30 and returned to lower portion 28 of column 43.

From the above data, it can be seen that the conversion of EC was 100%, the yield of DMC was 93% (DMC was produced at a production rate of 228.3 g/h), the selectivity for DMC was not lower than 99%, the yield of high purity EG was not lower than 99%, and the selectivity for EG was not lower than 99%. As apparent from the above, EC did not remain in the hydrolysis reaction mixture. The productivity of DMC in terms of the space time yields was: 228.3/1.13= 202.4 g/liter.h.

EXAMPLE 10

Figure 11:
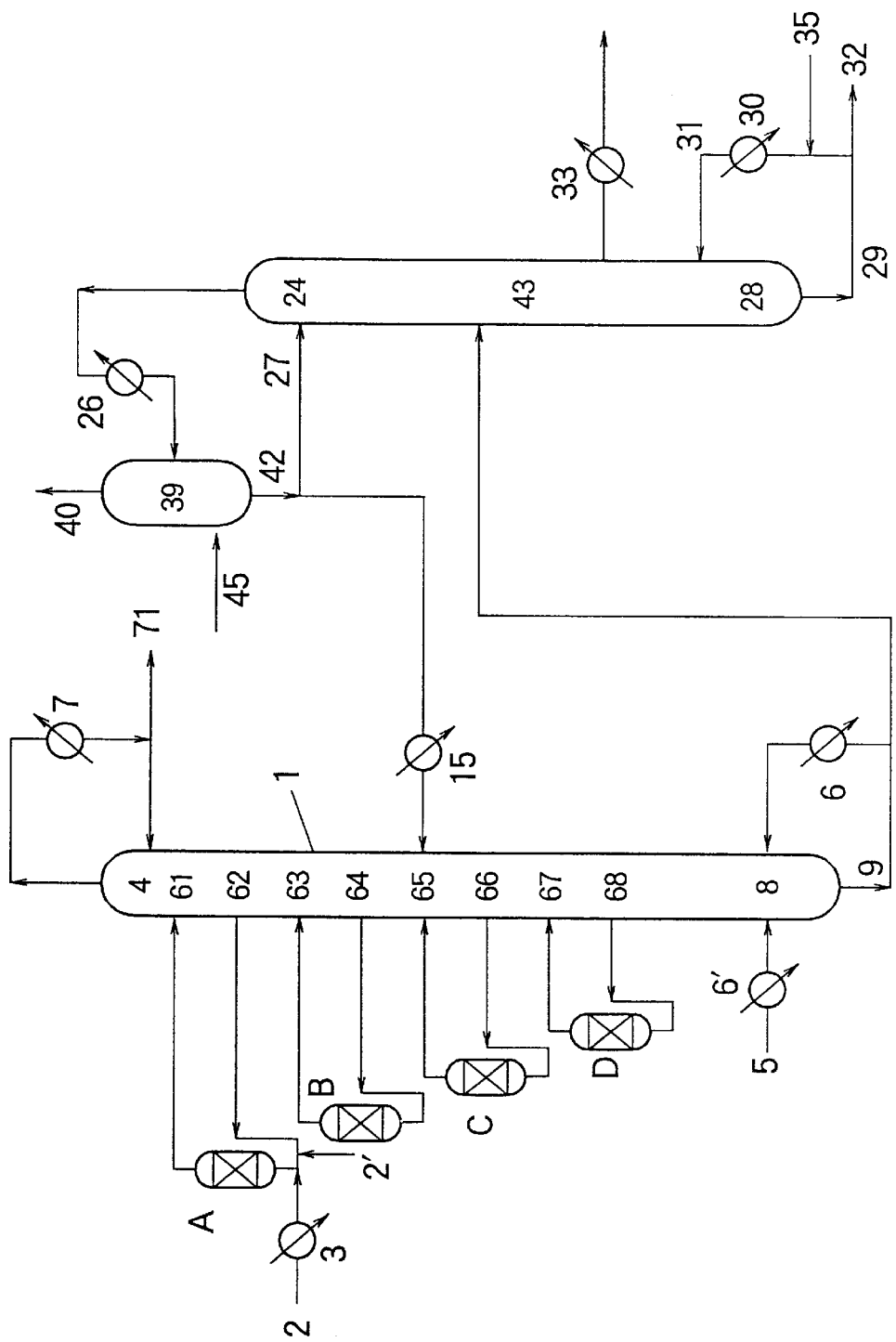
FIG. 11 is a diagram showing the system which was used for practicing Example 10 of the present application.

Using a system as shown in FIG. 11, dimethyl carbonate (DMC) and ethylene glycol (EG) were continuously produced from ethylene carbonate (EC) and methanol (MeOH).

Continuous multi-stage distillation column 1 (which was of the same type as used in Example 7) was operated in substantially the same manner as in Example 7, except that the mixture of MeOH and DMC (MeOH/DMC weight ratio=85/15) was continuously fed to continuous multi-stage distillation column 1 at a flow rate of 614 g/h. Continuous multi-stage distillation column 1 was operated under atmospheric pressure, and the temperature of upper portion 4 (above the uppermost stage) of the distillation column was 64° C.

A gaseous mixture distilled from the top of distillation column 1 was condensed by condenser 7 to obtain a condensate. A part of the obtained condensate (containing MeOH and DMC in concentrations of 53.2% by weight and 46.8% by weight, respectively) was recovered from the system through conduit 71 at a flow rate of 680 g/h. The remainder of the condensate was returned to upper portion 4 of distillation column 1. A liquid reaction mixture [containing low-boiling point mixture (comprised of MeOH and DMC), EG and EC in concentrations of 27.6% by weight, 65.2% by weight and 7.1% by weight, respectively] was withdrawn from the bottom of distillation column 1, and a part of the withdrawn reaction mixture was fed, at a flow rate of 272 g/h, to continuous hydrolysis reaction column 43 having an inner diameter of 2.5 cm and a packing height of 250 cm at a position 90 cm below the top of column 43 [which continuous hydrolysis reaction column 43 had been packed with stainless-steel Dixon packings (6 mm $\phi$), and the pressure of upper portion 24 (above the uppermost stage) was $2.7 \times 10^4$ Pa (200 torr) and the temperature of lower portion 28 (below the lowermost stage) was 161° C.]. A gaseous mixture withdrawn from the top of continuous hydrolysis reaction column 43 was condensed by condenser 26, and the resultant condensate was introduced to gas-liquid separator 39, from which carbon dioxide was discharged through conduit 40, and a mixture of MeOH and DMC was withdrawn from the bottom of gas-liquid separator 39 through conduit 42 at a flow rate of 75 g/h. During the gas-liquid separation, nitrogen gas was fed to the lower portion of gas-liquid separator 39 through conduit 45, in order to separate carbon dioxide from the liquid mixture of MeOH and DMC. A part of the withdrawn MeOH/DMC mixture was returned to continuous multi-stage distillation column 1 through evaporator 15 at a position 120 cm below the top of the distillation column at a flow rate of 75 g/h, while returning, through conduit 27, the remainder of the mixture to upper portion 24 of continuous hydrolysis reaction column 43.

A liquid hydrolysis reaction mixture (containing EG in a concentration of 97% by weight) was withdrawn from the bottom of continuous hydrolysis reaction column 43, and a part of the withdrawn mixture was recovered through conduit 32 at a flow rate of 22 g/h. The remainder of the withdrawn mixture was heated by reboiler 30 and returned to lower portion 28 of column 43, together with water which was introduced to the inlet of reboiler 30 at a flow rate of 3.9 g/h so that the concentration of water in above-mentioned condensate derived from the gaseous mixture withdrawn from the top of column 43 was maintained at a concentration not more than 50 ppm. The weight ratio of water to EC in the mixture fed to continuous hydrolysis reactor 43 was 0.33. From a withdrawal port provided in a side wall of column 43 at a position 230 cm below the top of column 43, a mixture of EG and a small amount of water was recovered through condenser 33. The recovered mixture was analyzed and, as a result, it was found that the recovered mixture contained only EG and water. The flow rate of the mixture, after removal of the waters was 169 g/h. The EG content of the mixture was not lower than 99.999% by weight.

From the above data, it can be seen that the conversion of EC was 100%, the yield of DMC was 92% (DMC was produced at a production rate of 225.9 g/h), the selectivity for DMC was not lower than 99%, the yield of high purity EG was not lower than 99% and the selectivity for EG was not lower than 99%. As apparent from the above, EC did not remain in the hydrolysis reaction mixture. The productivity of DMC in terms of the space time yield was: 225.9/1.13= 200.3 g/liter.h.

INDUSTRIAL APPLICABILITY

By the method of the present invention, it becomes possible that a dialkyl carbonate and a high purity diol is continuously produced from a cyclic carbonate and an aliphatic monohydric alcohol, with high productivity, without using a large reactor or a complicated separating system, irrespective of whether the feedstock aliphatic monohydric alcohol does not contain or contains a concomitant dialkyl carbonate in an amount up to 40% by weight.

We claim:

1. A method for continuously producing a dialkyl carbonate and a diol from a cyclic carbonate and an aliphatic monohydric alcohol, comprising:

(1) continuously feeding a cyclic carbonate represented by the following formula (A):

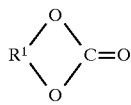 (A)

wherein $R^1$ is a divalent group represented by the formula —$(CH_2)_m$—, wherein m is an integer of from 2 to 6, which is unsubstituted or substituted with at least one substituent selected from the group consisting of a $C_1$–$C_{10}$ alkyl group and a $C_6$–$C_{10}$ aryl group, and an aliphatic monohydric alcohol represented by the following formula (B):

$R^2OH$ (B)

wherein $R^2$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group, to a continuous multi-stage distillation column, wherein said aliphatic monohydric alcohol contains a concomitant dialkyl carbonate in an amount of from 0 to 40% by weight, based on the total weight of said aliphatic monohydric alcohol and said concomitant dialkyl carbonate, and continuously effecting a transesterification between said cyclic carbonate and said aliphatic monohydric alcohol in the presence of a transesterification catalyst in at least one reaction zone selected from the group consisting of (a) said multi-stage distillation column, and (b) at least one transesterification reactor which is disposed outside of said multi-stage distillation column and which has an inlet and an outlet, each fluid-tightly communicating with said multi-stage distillation column, thereby continuously producing a dialkyl carbonate and a diol, while continuously withdrawing a low boiling point mixture containing the produced dialkyl carbonate in a gaseous form from an upper portion of said multi-stage distillation column and continuously withdrawing a high boiling point mixture containing the produced diol and unreacted cyclic carbonate in a liquid form from a lower portion of said multi-stage distillation column, wherein when said transesterification is conducted in said transesterification reactor, a liquid flowing-down inside said multi-stage distillation column is continuously withdrawn through at least one withdrawal port provided in a side wall of the multi-stage distillation column at a position or positions thereof corresponding to a stage or stages selected from the group consisting of intermediate stages and a lowermost stage of said multi-stage distillation column, and said withdrawn liquid is continuously introduced to said transesterification reactor through said inlet thereof to thereby contact the cyclic carbonate and aliphatic monohydric alcohol contained in said withdrawn liquid with said transesterification catalyst and effect a transesterification between said cyclic carbonate and said aliphatic monohydric alcohol, whereupon the resultant reaction mixture is continuously withdrawn from said at least one transesterification reactor through said outlet thereof and recycled to said multi-stage distillation column through an introduction port provided in the side wall of the multi-stage distillation column at a position above the or each withdrawal port; and (2) continuously feeding water and said high boiling point mixture withdrawn from the lower portion of said multi-stage distillation column in step (1) to a continuous hydrolysis reactor, to thereby effect a continuous hydrolysis of said unreacted cyclic carbonate and produce a diol and carbon dioxide, while continuously withdrawing the resultant hydrolysis reaction mixture containing the produced diol from said continuous hydrolysis reactor.

2. The method according to claim 1, wherein the conversion of said cyclic carbonate in step (1) is from 80 to 99%.

3. The method according to claim 1 or 2, wherein, in step (1), said cyclic carbonate in a liquid form is continuously fed to an upper portion of said continuous multi-stage distillation column, and said aliphatic monohydric alcohol in a gaseous form is continuously fed to a lower portion of said continuous multi-stage distillation column.

4. The method according to claim 1 or 2, wherein, in step (2), said continuous hydrolysis of said unreacted cyclic carbonate is conducted in the presence of at least one hydrolysis catalyst selected from the group consisting of a solid catalyst and a homogeneous catalyst.

5. The method according to claim 1 or 2, wherein said high boiling point mixture withdrawn from a lower portion of said continuous multi-stage distillation column in step (1) contains said aliphatic monohydric alcohol and said dialkyl carbonate, and wherein said high boiling point mixture is continuously introduced, prior to the feeding thereof to said continuous hydrolysis reactor in step (2), to a low boiling point mixture-separating column which is comprised of a continuous multi-stage distillation column, and wherein a low boiling point mixture containing said aliphatic monohydric alcohol and said dialkyl carbonate which are contained in said high boiling point mixture is continuously withdrawn from an upper portion of said low boiling point mixture-separating column, while continuously withdrawing a high boiling point mixture containing said unreacted cyclic carbonate and said diol from a lower portion of said low boiling point mixture-separating column, wherein said low boiling point mixture withdrawn from the upper portion of said low boiling point mixture-separating column is continuously recycled to said multi-stage distillation column used in step (1), while continuously feeding said high boiling point mixture withdrawn from said low boiling point mixture-separating column to said continuous hydrolysis reactor used in step (2).

6. The method according to claim 1 or 2, wherein said continuous hydrolysis reactor is selected from the group consisting of a tube reactor and a vessel reactor, and wherein the produced hydrolysis reaction mixture containing said diol and said carbon dioxide is continuously introduced to a diol-separating column which is comprised of a continuous multi-stage distillation column and wherein said diol is continuously withdrawn from a lower portion of said diol-separating column, while continuously withdrawing a low boiling point mixture containing said carbon dioxide from an upper portion of said diol-separating column.

7. The method according to claim 5, wherein said continuous hydrolysis reactor is a hydrolysis column comprised of a continuous multi-stage distillation column, and wherein a high boiling point mixture containing said diol is withdrawn from a lower portion of said continuous hydrolysis column, while continuously withdrawing a low boiling point mixture containing said carbon dioxide from an upper portion of said continuous hydrolysis column.

8. The method according to claim 7, wherein said high boiling point mixture withdrawn from the lower portion of said low boiling point mixture-separating column is continuously introduced to said continuous hydrolysis column through an introduction port provided in a side wall of said hydrolysis column at a position above a withdrawal port provided in a side wall of said continuous hydrolysis column for withdrawing said diol.

9. The method according to claim 7, wherein said water is continuously introduced to said continuous hydrolysis column at a position above said withdrawal port for withdrawing said diol.

10. The method according to claim 5, wherein said cyclic carbonate is capable of forming a minimum boiling point azeotropic mixture with said diol, and wherein said high boiling point mixture withdrawn from the lower portion of said low boiling point mixture-separating column is continuously introduced to an azeotropic mixture-separating column prior to the feeding of said high boiling point mixture to said continuous hydrolysis reactor, while continuously withdrawing said diol from a lower portion of said azeotropic mixture-separating column and continuously withdrawing a low boiling point mixture containing the minimum boiling point azeotropic mixture of said cyclic carbonate with said diol from an upper portion of said azeotropic mixture-separating column, and wherein said low boiling point mixture withdrawn from the upper portion of said azeotropic mixture-separating column is introduced to said continuous hydrolysis reactor to effect a hydrolysis reaction and obtain a hydrolysis reaction mixture.

11. The method according to claim 10, wherein said hydrolysis reaction mixture is recycled to said azeotropic mixture-separating column.

12. The method according to claim 1 or 2, wherein said high boiling point mixture withdrawn from a lower portion of said continuous multi-stage distillation column in step (1) contains said aliphatic monohydric alcohol and said dialkyl carbonate, wherein said continuous hydrolysis reactor is a continuous hydrolysis column comprised of a continuous multi-stage distillation column, and wherein a low boiling point mixture containing said monohydric alcohol, said dialkyl carbonate and said carbon dioxide is continuously withdrawn from an upper portion of said continuous hydrolysis column and recycled to said continuous multi-stage distillation column used in step (1), while continuously withdrawing said diol from a lower portion of said continuous hydrolysis column.

13. The method according to claim 12, wherein said carbon dioxide or both of said carbon dioxide and said water are removed from said low boiling point mixture withdrawn from the upper portion of said continuous hydrolysis column prior to the recycling of said low boiling point mixture to said continuous multi-stage distillation column used in step (1).

14. The method according to claim 12, wherein said high boiling point mixture withdrawn from the lower portion of said continuous multi-stage distillation column used in step (1) is fed to said continuous hydrolysis column at a position above a withdrawal port provided in a side wall of said continuous hydrolysis column for withdrawing said diol.

15. The method according to claim 1 or 2, wherein said cyclic carbonate is ethylene carbonate and said aliphatic monohydric alcohol is selected from the group consisting of methanol, ethanol, n-propanol, iso-propanol, n-butanol, iso-butanol, sec-butanol and tert-butanol.

16. The method according to claim 15, wherein said cyclic carbonate is ethylene carbonate and said aliphatic monohydric alcohol is methanol.

* * * * *